(12) United States Patent
Leung et al.

(10) Patent No.: US 8,870,863 B2
(45) Date of Patent: *Oct. 28, 2014

(54) CATHETER APPARATUSES, SYSTEMS, AND METHODS FOR RENAL NEUROMODULATION

(75) Inventors: Mark S. Leung, Palo Alto, CA (US); Benjamin J. Clark, Redwood City, CA (US); Kenneth J. Michlitsch, Livermore, CA (US); Erik Thai, San Jose, CA (US); Andrew Wu, Foster City, CA (US); Denise Zarins, Saratoga, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 12/790,639

(22) Filed: May 28, 2010

(65) Prior Publication Data

US 2011/0264075 A1    Oct. 27, 2011

Related U.S. Application Data

(60) Provisional application No. 61/328,105, filed on Apr. 26, 2010.

(51) Int. Cl.
*A61B 18/14* (2006.01)
*A61B 18/18* (2006.01)
*A61B 18/02* (2006.01)
*A61B 18/08* (2006.01)
*A61B 18/20* (2006.01)
*A61B 18/00* (2006.01)

(52) U.S. Cl.
CPC ......... *A61B 18/1492* (2013.01); *A61B 18/0206* (2013.01); *A61B 18/082* (2013.01); *A61B 18/1815* (2013.01); *A61B 18/20* (2013.01); *A61B 2018/00434* (2013.01); *A61B 2018/00511* (2013.01); *A61B 2018/00577* (2013.01); *A61B 2018/00714* (2013.01); *A61B 2018/00815* (2013.01); *A61B 2018/00821* (2013.01); *A61B 2018/00875* (2013.01); *A61B 2018/00404* (2013.01)
USPC ............................................... 606/41; 606/33

(58) Field of Classification Search
USPC .............................. 606/27–31, 33, 34, 41–47
See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| CN | 102551874 | 7/2012 |
| CN | 102551878 | 7/2012 |

(Continued)

OTHER PUBLICATIONS

U.S. Appl. No. 12/790,639, Wu et al.

(Continued)

*Primary Examiner* — Michael Peffley
*Assistant Examiner* — Khadijeh Vahdat

(57) ABSTRACT

Catheter apparatuses, systems, and methods for achieving renal neuromodulation by intravascular access are disclosed herein. One aspect of the present application, for example, is directed to apparatuses, systems, and methods that incorporate a catheter treatment device comprising an elongated shaft. The elongated shaft is sized and configured to deliver an energy delivery element to a renal artery via an intravascular path. Thermal or electrical renal neuromodulation may be achieved via direct and/or via indirect application of thermal and/or electrical energy to heat or cool, or otherwise electrically modulate, neural fibers that contribute to renal function, or of vascular structures that feed or perfuse the neural fibers.

43 Claims, 37 Drawing Sheets

(56) References Cited

U.S. PATENT DOCUMENTS

| | | | |
|---|---|---|---|
| 4,709,698 A | 12/1987 | Johnston et al. | |
| 4,764,504 A | 8/1988 | Johnson et al. | |
| 4,966,597 A | 10/1990 | Cosman | |
| 4,976,711 A | 12/1990 | Parins et al. | |
| 5,170,803 A | 12/1992 | Hewson | |
| 5,203,772 A | 4/1993 | Hammerslag | |
| 5,300,068 A | 4/1994 | Rosar et al. | |
| 5,322,064 A * | 6/1994 | Lundquist | 600/381 |
| 5,327,905 A | 7/1994 | Avitall | |
| 5,329,923 A | 7/1994 | Lundquist | |
| 5,354,297 A | 10/1994 | Avitall | |
| 5,358,514 A | 10/1994 | Schulman et al. | |
| 5,368,591 A | 11/1994 | Lennox et al. | |
| 5,399,164 A | 3/1995 | Snoke et al. | |
| 5,415,633 A | 5/1995 | Lazarus | |
| 5,421,349 A | 6/1995 | Rodriguez et al. | |
| 5,423,744 A | 6/1995 | Gencheff et al. | |
| 5,425,364 A | 6/1995 | Imran | |
| 5,437,288 A * | 8/1995 | Schwartz et al. | 600/585 |
| 5,441,483 A | 8/1995 | Avitall | |
| 5,458,585 A | 10/1995 | Salmon et al. | |
| 5,477,856 A | 12/1995 | Lundquist | |
| 5,484,400 A | 1/1996 | Edwards et al. | |
| 5,487,757 A | 1/1996 | Truckai | |
| 5,545,200 A | 8/1996 | West et al. | |
| 5,558,643 A | 9/1996 | Samson et al. | |
| 5,571,147 A | 11/1996 | Sluijter et al. | |
| 5,599,345 A | 2/1997 | Edwards et al. | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,766,167 A * | 6/1998 | Eggers et al. | 606/46 |
| 5,772,590 A | 6/1998 | Webster, Jr. | |
| 5,807,249 A | 9/1998 | Qin et al. | |
| 5,810,802 A | 9/1998 | Panescu et al. | |
| 5,823,955 A | 10/1998 | Kuck et al. | |
| 5,865,787 A | 2/1999 | Shapland | |
| 5,871,444 A | 2/1999 | Ouchi et al. | |
| 5,893,885 A | 4/1999 | Webster | |
| 5,899,898 A | 5/1999 | Arless et al. | |
| 5,916,178 A | 6/1999 | Noone et al. | |
| 5,916,214 A | 6/1999 | Cosio et al. | |
| 5,935,102 A | 8/1999 | Bowden et al. | |
| 5,944,710 A | 8/1999 | Dev et al. | |
| 5,954,719 A | 9/1999 | Chen et al. | |
| 5,983,141 A | 11/1999 | Sluijter et al. | |
| 5,984,907 A | 11/1999 | McGee et al. | |
| 6,004,269 A | 12/1999 | Crowley et al. | |
| 6,009,877 A | 1/2000 | Edwards | |
| 6,042,580 A | 3/2000 | Simpson | |
| 6,049,737 A | 4/2000 | Simpson et al. | |
| 6,064,902 A | 5/2000 | Haissaguerre et al. | |
| 6,066,134 A | 5/2000 | Eggers et al. | |
| 6,099,524 A | 8/2000 | Lipson et al. | |
| 6,106,518 A | 8/2000 | Wittenberger et al. | |
| 6,117,101 A | 9/2000 | Diederich et al. | |
| 6,135,999 A | 10/2000 | Fanton et al. | |
| 6,149,620 A | 11/2000 | Baker et al. | |
| 6,161,048 A | 12/2000 | Sluijter et al. | |
| 6,197,021 B1 | 3/2001 | Panescu et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,246,914 B1 | 6/2001 | De la Rama et al. | |
| 6,273,886 B1 | 8/2001 | Edwards et al. | |
| 6,283,951 B1 | 9/2001 | Flaherty et al. | |
| 6,283,960 B1 | 9/2001 | Ashley | |
| 6,287,306 B1 | 9/2001 | Kroll et al. | |
| 6,292,695 B1 | 9/2001 | Webster et al. | |
| 6,312,425 B1 | 11/2001 | Simpson et al. | |
| 6,314,325 B1 | 11/2001 | Fitz | |
| 6,319,250 B1 | 11/2001 | Falwell et al. | |
| 6,322,558 B1 | 11/2001 | Taylor et al. | |
| 6,322,559 B1 | 11/2001 | Daulton et al. | |
| 6,405,067 B1 | 6/2002 | Mest et al. | |
| 6,405,732 B1 | 6/2002 | Edwards et al. | |
| 6,413,255 B1 | 7/2002 | Stern | |
| 6,488,679 B1 | 12/2002 | Swanson et al. | |
| 6,500,172 B1 | 12/2002 | Panescu et al. | |
| 6,506,189 B1 | 1/2003 | Rittman, III et al. | |
| 6,514,226 B1 | 2/2003 | Levin et al. | |
| 6,522,926 B1 | 2/2003 | Kieval et al. | |
| 6,562,034 B2 | 5/2003 | Edwards et al. | |
| 6,605,087 B2 | 8/2003 | Swartz et al. | |
| 6,611,720 B2 | 8/2003 | De la Rama et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,638,278 B2 | 10/2003 | Falwell et al. | |
| 6,685,648 B2 | 2/2004 | Flaherty et al. | |
| 6,716,207 B2 | 4/2004 | Farnholtz | |
| 6,736,835 B2 | 5/2004 | Pellegrino et al. | |
| 6,780,181 B2 | 8/2004 | Kroll et al. | |
| 6,845,267 B2 | 1/2005 | Harrison et al. | |
| 6,850,801 B2 | 2/2005 | Kieval et al. | |
| 6,885,888 B2 | 4/2005 | Rezai | |
| 6,893,436 B2 | 5/2005 | Woodard et al. | |
| 6,926,669 B1 | 8/2005 | Stewart et al. | |
| 6,939,346 B2 | 9/2005 | Kannenberg et al. | |
| 6,978,174 B2 | 12/2005 | Gelfand et al. | |
| 7,149,574 B2 | 12/2006 | Yun et al. | |
| 7,162,303 B2 | 1/2007 | Levin et al. | |
| 7,171,275 B2 | 1/2007 | Hata et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,575,566 B2 | 8/2009 | Scheib | |
| 7,591,813 B2 | 9/2009 | Levine et al. | |
| 7,615,067 B2 | 11/2009 | Lee et al. | |
| 7,617,005 B2 | 11/2009 | Demarais et al. | |
| 7,620,451 B2 | 11/2009 | Demarais et al. | |
| 7,637,903 B2 | 12/2009 | Lentz et al. | |
| 7,647,115 B2 | 1/2010 | Levin et al. | |
| 7,653,438 B2 | 1/2010 | Deem et al. | |
| 7,655,006 B2 | 2/2010 | Sauvageau et al. | |
| 7,662,151 B2 | 2/2010 | Crompton, Jr. et al. | |
| 7,674,411 B2 | 3/2010 | Berg et al. | |
| 7,676,910 B2 | 3/2010 | Kiepen et al. | |
| 7,682,319 B2 | 3/2010 | Martin et al. | |
| 7,686,802 B2 | 3/2010 | Stevens-Wright | |
| 7,695,451 B2 | 4/2010 | Bencini et al. | |
| 7,699,843 B2 | 4/2010 | Sutter et al. | |
| 7,702,397 B2 | 4/2010 | Fredricks et al. | |
| 7,708,704 B2 | 5/2010 | Mitelberg et al. | |
| 7,715,903 B2 * | 5/2010 | Hartley et al. | 600/433 |
| 7,717,948 B2 | 5/2010 | Demarais et al. | |
| 7,727,187 B2 | 6/2010 | Lentz | |
| 7,731,681 B2 | 6/2010 | Schaer et al. | |
| 7,731,682 B2 | 6/2010 | Bencini et al. | |
| 7,744,586 B2 | 6/2010 | Larson et al. | |
| 7,756,583 B2 | 7/2010 | Demarais et al. | |
| 7,758,564 B2 | 7/2010 | Long et al. | |
| 7,766,868 B2 | 8/2010 | Goode et al. | |
| 7,770,584 B2 | 8/2010 | Danek et al. | |
| 7,771,410 B2 | 8/2010 | Venturelli | |
| 7,778,703 B2 | 8/2010 | Gross et al. | |
| 7,780,646 B2 | 8/2010 | Farnholtz | |
| 7,792,589 B2 | 9/2010 | Levy, Jr. et al. | |
| 7,806,872 B2 | 10/2010 | Ponzi | |
| 7,815,637 B2 | 10/2010 | Ormsby et al. | |
| 7,824,399 B2 | 11/2010 | Francischelli et al. | |
| 7,833,191 B2 | 11/2010 | Flach et al. | |
| 7,850,675 B2 | 12/2010 | Bell et al. | |
| 7,854,740 B2 | 12/2010 | Carney | |
| 7,875,018 B2 | 1/2011 | Tockman et al. | |
| 7,892,233 B2 | 2/2011 | Hall et al. | |
| 7,896,872 B2 | 3/2011 | Finch et al. | |
| 7,905,828 B2 | 3/2011 | Brock et al. | |
| 7,914,467 B2 | 3/2011 | Layman et al. | |
| 7,938,828 B2 | 5/2011 | Koblish | |
| 7,947,016 B2 | 5/2011 | Lentz | |
| 7,955,298 B2 | 6/2011 | Carroll et al. | |

(56) References Cited

U.S. PATENT DOCUMENTS

| | | |
|---|---|---|
| 7,955,326 B2 | 6/2011 | Paul et al. |
| 7,959,626 B2 | 6/2011 | Hong et al. |
| 7,976,539 B2 | 7/2011 | Hlavka et al. |
| 7,985,215 B2 | 7/2011 | Guo et al. |
| 7,998,112 B2 | 8/2011 | Chow et al. |
| 8,034,050 B2 | 10/2011 | Sharareh et al. |
| 8,043,279 B2 | 10/2011 | Hisamatsu et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0065542 A1 | 5/2002 | Lax |
| 2002/0128662 A1 | 9/2002 | Brock et al. |
| 2002/0165532 A1 | 11/2002 | Hill et al. |
| 2002/0183682 A1 | 12/2002 | Darvish |
| 2003/0050681 A1 | 3/2003 | Pianca et al. |
| 2003/0055422 A1* | 3/2003 | Lesh ................. 606/41 |
| 2003/0060858 A1 | 3/2003 | Kieval et al. |
| 2003/0109778 A1 | 6/2003 | Rashidi |
| 2003/0125720 A1* | 7/2003 | Woodard et al. ............... 606/15 |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2004/0010289 A1 | 1/2004 | Biggs et al. |
| 2004/0193149 A1 | 9/2004 | Koblish |
| 2004/0215186 A1 | 10/2004 | Cornelius et al. |
| 2004/0243102 A1 | 12/2004 | Berg et al. |
| 2005/0004644 A1* | 1/2005 | Kelsch et al. ............... 607/131 |
| 2005/0080409 A1 | 4/2005 | Young et al. |
| 2005/0187455 A1 | 8/2005 | Rashidi |
| 2005/0187579 A1 | 8/2005 | Danek et al. |
| 2005/0228460 A1 | 10/2005 | Levin et al. |
| 2005/0234523 A1 | 10/2005 | Levin et al. |
| 2006/0004346 A1 | 1/2006 | Begg |
| 2006/0025821 A1 | 2/2006 | Gelfand et al. |
| 2006/0041277 A1 | 2/2006 | Deem et al. |
| 2006/0095029 A1 | 5/2006 | Young et al. |
| 2006/0095030 A1 | 5/2006 | Avitall et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0235474 A1 | 10/2006 | Demarais |
| 2006/0253115 A1 | 11/2006 | Avitall et al. |
| 2006/0253116 A1 | 11/2006 | Avitall et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0173899 A1 | 7/2007 | Levin et al. |
| 2007/0265687 A1 | 11/2007 | Deem et al. |
| 2008/0213331 A1 | 9/2008 | Gelfand et al. |
| 2008/0249525 A1 | 10/2008 | Lee et al. |
| 2008/0255642 A1* | 10/2008 | Zarins et al. ............... 607/99 |
| 2008/0319513 A1 | 12/2008 | Pu et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0204060 A1 | 8/2009 | Desinger et al. |
| 2009/0209943 A1 | 8/2009 | Marsman |
| 2009/0306651 A1 | 12/2009 | Schneider |
| 2009/0312606 A1 | 12/2009 | Dayton et al. |
| 2010/0004632 A1 | 1/2010 | Wu et al. |
| 2010/0010567 A1 | 1/2010 | Deem et al. |
| 2010/0022989 A1 | 1/2010 | Parasmo et al. |
| 2010/0057037 A1 | 3/2010 | Webler et al. |
| 2010/0057150 A1 | 3/2010 | Demarais et al. |
| 2010/0069882 A1 | 3/2010 | Jennings et al. |
| 2010/0094281 A1 | 4/2010 | Hauck et al. |
| 2010/0099952 A1 | 4/2010 | Adams |
| 2010/0100073 A1 | 4/2010 | Lentz et al. |
| 2010/0137860 A1 | 6/2010 | Demarais et al. |
| 2010/0137952 A1 | 6/2010 | Demarais et al. |
| 2010/0168666 A1 | 7/2010 | Tegg |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0217184 A1 | 8/2010 | Koblish et al. |
| 2010/0217261 A1 | 8/2010 | Watson |
| 2010/0222851 A1 | 9/2010 | Deem et al. |
| 2010/0222854 A1 | 9/2010 | Demarais et al. |
| 2010/0228112 A1 | 9/2010 | Von Malmborg |
| 2010/0228152 A1 | 9/2010 | Fisher et al. |
| 2010/0249773 A1 | 9/2010 | Clark et al. |
| 2010/0268307 A1 | 10/2010 | Demarais et al. |
| 2010/0280316 A1 | 11/2010 | Dietz et al. |
| 2010/0318081 A1 | 12/2010 | Sato et al. |
| 2010/0324482 A1 | 12/2010 | Farnholtz |
| 2010/0331776 A1 | 12/2010 | Salahieh et al. |
| 2011/0034989 A1 | 2/2011 | Al-Marashi et al. |
| 2011/0040238 A1 | 2/2011 | Wulfman et al. |
| 2011/0046607 A1 | 2/2011 | Halevy |
| 2011/0054464 A1 | 3/2011 | Werneth et al. |
| 2011/0060314 A1 | 3/2011 | Wallace et al. |
| 2011/0066105 A1 | 3/2011 | Hart et al. |
| 2011/0118582 A1 | 5/2011 | De la Rama et al. |
| 2011/0178505 A1 | 7/2011 | Odland et al. |
| 2011/0245808 A1 | 10/2011 | Voeller et al. |
| 2011/0264011 A1 | 10/2011 | Wu et al. |
| 2011/0276034 A1 | 11/2011 | Tomarelli et al. |
| 2012/0029505 A1 | 2/2012 | Jenson |
| 2012/0029510 A1 | 2/2012 | Haverkost |
| 2012/0123258 A1 | 5/2012 | Willard |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130368 A1 | 5/2012 | Jenson |
| 2012/0136350 A1 | 5/2012 | Goshgarian et al. |
| 2012/0143097 A1 | 6/2012 | Pike, Jr. |
| 2012/0157992 A1 | 6/2012 | Smith et al. |
| 2012/0172837 A1 | 7/2012 | Demarais et al. |
| 2012/0184952 A1 | 7/2012 | Jenson et al. |
| 2012/0265198 A1 | 10/2012 | Crow et al. |
| 2013/0035681 A1 | 2/2013 | Subramaniam et al. |
| 2013/0090647 A1 | 4/2013 | Smith |
| 2013/0090649 A1 | 4/2013 | Smith et al. |
| 2013/0096553 A1 | 4/2013 | Hill et al. |
| 2013/0131667 A1 | 5/2013 | Jenson et al. |
| 2013/0172880 A1 | 7/2013 | Willard |

FOREIGN PATENT DOCUMENTS

| | | |
|---|---|---|
| CN | 103096826 | 5/2013 |
| EP | 0348136 B1 | 8/1993 |
| EP | 0737487 | 10/1996 |
| EP | 0737487 A2 | 10/1996 |
| EP | 0521595 B1 | 5/1999 |
| EP | 0937481 A1 | 8/1999 |
| EP | 0951244 B1 | 3/2004 |
| EP | 1634541 | 3/2006 |
| EP | 2106821 | 10/2009 |
| EP | 1982741 B1 | 6/2010 |
| EP | 2332607 | 6/2011 |
| EP | 2563255 | 3/2013 |
| WO | WO-94/21165 | 9/1994 |
| WO | WO-9525472 | 9/1995 |
| WO | WO-96/00033 | 1/1996 |
| WO | WO-9736548 A1 | 10/1997 |
| WO | WO-99/00060 | 1/1999 |
| WO | WO-9911313 | 3/1999 |
| WO | WO-9911313 A1 | 3/1999 |

(56) References Cited

FOREIGN PATENT DOCUMENTS

| WO | WO-0122897 A1 | 4/2001 |
|---|---|---|
| WO | WO-0170114 A1 | 9/2001 |
| WO | WO-2005/041748 A2 | 5/2005 |
| WO | WO-2005110528 A1 | 11/2005 |
| WO | WO-2006022790 A1 | 3/2006 |
| WO | WO-2006041847 | 4/2006 |
| WO | WO-2006041881 | 4/2006 |
| WO | WO-2006041881 A2 | 4/2006 |
| WO | WO-2007008954 A2 | 1/2007 |
| WO | WO-2007035537 | 3/2007 |
| WO | WO-2007078997 A2 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008061150 | 5/2008 |
| WO | WO-2008061152 | 5/2008 |
| WO | WO-2008070413 | 6/2008 |
| WO | WO-2009086007 | 7/2009 |
| WO | WO-2009108997 A1 | 9/2009 |
| WO | WO-2009125575 A1 | 10/2009 |
| WO | WO-2010078175 A1 | 7/2010 |
| WO | WO-2012054906 | 4/2012 |
| WO | WO-2013056672 | 1/2013 |
| WO | WO-2013055537 | 4/2013 |
| WO | WO-2013058962 | 4/2013 |

OTHER PUBLICATIONS

U.S. Appl. No. 12/871,457, Wu et al.
U.S. Appl. No. 12/940,922, Gelfand et al.
U.S. Appl. No. 12/996,987, Demarais.
U.S. Appl. No. 13/007,370, Gelfand et al.
U.S. Appl. No. 13/009,748, Beetel et al.
U.S. Appl. No. 12/910,631, Wu et al.
International Search Report and Written Opinion for PCT/US2009/069334; Applicant: Ardian, Inc.; Mailing Date: Mar. 1, 2010, 10 pages.
International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report, PCT/US04/38498, Mailed Feb. 18, 2005, Applicant: G & L Consulting, LLC, 4 pages.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant: Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Search Report; European Patent Application No. 09156661.2; Applicant: Ardian, Inc.; Date of Mailing: Jul. 23, 2009, 6 pages.
European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
European Search Report; European Patent Application No. 07868755.5; Applicant: Ardian, Inc.; Date of Mailing: Jul. 28, 2010, 7 pages.
Ardian Medtronic LLC, International Search Report and Written Opinion dated Nov. 22, 2011, International Application No. PCT/US2011/033491, 16 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency cateheter ablation of accessory pathways in infants." Heart, 78:160-162 (1997).
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Han, Y.-M, et al., "Renal artery ebolization with diluted hot contrast medium: An experimental study." J Vasc Interv Radiol, 12: 862-868 (2001).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustrgarten, D.L.,et al., "Cryothermal ablation: Mechanism of tissue injury and current experience in the treatment of tachyarrhythmias." Progr Cardiovasc Dis, 41:481-498 (1999).
Oliverira, V., et al., "Renal denervation normalizes pressure and baroreceptor reflex in high renin hypertension in conscious rats." Hypertension, 19:II-17-II-21 (1992).
Peet, M., "Hypertension and its Surgical Treatment by bilateral supradiaphragmatic splanchnicectomy" Am J Surgery (1948) pp. 48-68.
Schauerte, P., et al. "Catheter ablation of cardiac autonomic nerves for prevention of vagal atrial fibrillation." Circulation, 102:2774-2780 (2000).

(56) References Cited

OTHER PUBLICATIONS

Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Weinstock, M., et al., "Renal denervation prevents sodium rentention and hypertension in salt sensitive rabbits with genetic baroreflex impairment." Clinical Science, 90:287-293 (1996).
Avitall et al., "The Creation of Linear Contiguous Lesions in the Atria with an Expandable Loop Catheter"; Journal of the American College of Cardiology, 1999; vol. 33, No. 4; pp. 972-984, located online at: http://content/onlinejacc.org/cgi/content/full/33/4/972.
Excerpt of Operator's Manual, 110V; Boston Scientific's EPT-1000 XP Cardiac Ablation Controller & Accessories, Version of Apr. 2003, (6 pages).
Excerpt of Operator's Manual, 150; Boston Scientific, "Maestro 3000 Cardiac Ablation System", Version of Oct. 17, 2005, Ref. Catalog No. 21020, (4 pages).
Opposition to European Patent No. EP2092957, Granted Jan. 5, 2011, Date of Opposition Oct. 5, 2011 (26 pages).
Opposition to European Patent No. EP2037840, Granted Dec. 7, 2011, Date of Opposition Sep. 7, 2012 (25 pages).
Opposition to European Patent No. EP1802370, Granted Jan. 5, 2011, Date of Opposition Oct. 5, 2011 (20 pages).
Wittkampf et al., "Control of Radiofrequency Lesion Size by Power Regulation"; Circulation: Journal of the American Heart Association; 1989, vol. 80: pp. 962-968, located online at: http://circ.ahajournals.org/content/80/4/962.
Zheng et al., "Comparison of the temperature profile and pathological effect at unipolar, bipolar and phased radiofrequency current configurations," Journal of Interventional Cardian Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
Tsao, Hsuan-Ming, Evaluation of Pulmonary Vein Stenosis after Catheter Ablation of Atrial Fibrillation, Cardiac Electrophysiology Review, 6, 2002, 4 pages.
International Search Report and Written Opinion for International App. No. PCT/US2011/057402, Applicant Medtronic Ardian Luxembourg S.A.R.L., Mail Date: Apr. 23, 2012, 19 pgs.
Non Final Office Action for U.S. Appl. No. 12/871,457, Mail Date: Nov. 7, 2013, 25 pages.
European Search Report for EP App. No. 13158996, Date Mailed: Nov. 14, 2013, 5 pages.
European Search Report for EP App. No. 13158998, Date Mailed: Nov. 15, 2013, 4 pages.
European Search Report for EP App. No. 13158999, Date Mailed, Nov. 19, 2013, 6 pages.
European Search Report for European Application No. 13159256, Date Mailed: Oct. 17, 2013, 6 pages.

(56) References Cited

OTHER PUBLICATIONS

Final Office Action for U.S. Appl. No. 12/871,457, Mail Date: Jul. 30, 2012, 48 pages.

Hall, W. H., et al. "Combined embolization and percutaneous radiofrequency ablation of a solid renal tumor." Am. J. Roentgenol,174: 1592-1594 (2000).

Hanson, J. M., et al. "The transplanted human kidney does not achieve functional reinnervation." Clin. Sci, 87: 13-19 (1994).

Hendee, W. R. et al. "Use of Animals in Biomedical Research: The Challenge and Response." *American Medical Association White Paper* (1988).

International Search Report and Written Opinion for International App. No. PCT/US2011/03349, Applicant Medtronic Ardian LLC, Mail Date: Nov. 22, 2011, 17 pgs.

Medical-Dictionary.com, Definition of "Animal Model," http://medical-dictionary.com (search "Animal Model"), 2005.

Medtronic, Inc., Annual Report (Form 10-K) (Jun. 28, 2011).

Non Final Office Action for U.S. Appl. No. 12/871,457, Mail Date: Feb. 3, 2012, 50 pages.

Ong, K. L., et al. "Prevalence, Awareness, Treatment, and Control of Hypertension Among United States Adults 1999-2004." Hypertension, 49: 69-75 (2007) (originally published online Dec. 11, 2006).

Renal Denervation (RDN), Symplicity RDN System Common Q&A (2011), http://www.medtronic.com/rdn/mediakit/RDN%20FAQ.pdf.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Blessing, Erwin et al., Cardiac Ablation and Renal Denervation Systems Have Distinct Purposes and Different Technical Requirements, JACC Cardiovascular Interventions, vol. 6, No. 3, 2013.

ClinicalTrials.gov, Renal Denervation in Patients with uncontrolled Hypertension in Chinese (2011), www.clinicaltrials.gov/ct2/show/NCT01390831.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, http://clinicaltrials.gov/ct2/show/NCT01628198.

Prochnau, Dirk et al., Catheter-based renal denervation for drug-resistant hypertension by using a standard electrophysiology catheter; Euro Intervention 2012, vol. 7, pp. 1077-1080.

Schneider, Peter A.., "Endovascular Skills—Guidewires, Catheters, Arteriography, Balloon Angioplasty, Stents", pp. 70-71, 101 and 188-190 (1998).

ThermoCool Irrigated Catheter and Integrated Ablation System, Biosense Webster (2006).

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison AwardsTM" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Final Office Action; U.S. Appl. No. 12/827,700; Mailed on Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hering, Dagmara et al., "Chronic kidney disease: role of sympathetic nervous system activation and potential benefits of renal denervation." EuroIntervention, vol. 9, 2013, 9 pages.

(56) References Cited

OTHER PUBLICATIONS

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Linz, Dominik et al., "Renal denervation suppresses ventricular arrhythmias during acute ventricular ischemia in pigs." Heart Rhythm, vol. 0, No. 0, 2013, 6 pages.

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Millard, F. C., et al, "Renal Embolization for ablation of function in renal failure and hypertension." Postgraduate Medical Journal, 65, 729-734, (1989).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Stouffer, G. A. et al., Journal of Molecular and Cellular Cardiology, vol. 62, 2013, 6 pages.

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Curtis, John J. et al., "Surgical Therapy for Persistent Hypertension After Renal Transplantation" Transplantation, 31:125-128 (1981).

Gelfand, M., et al., "Treatment of renal failure and hypertension." U.S. Appl. No. 60/442,970, filed Jan. 29, 2003, 23 pages.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

\* cited by examiner

*Arterial Vasculature*

*Venous Vasculature*

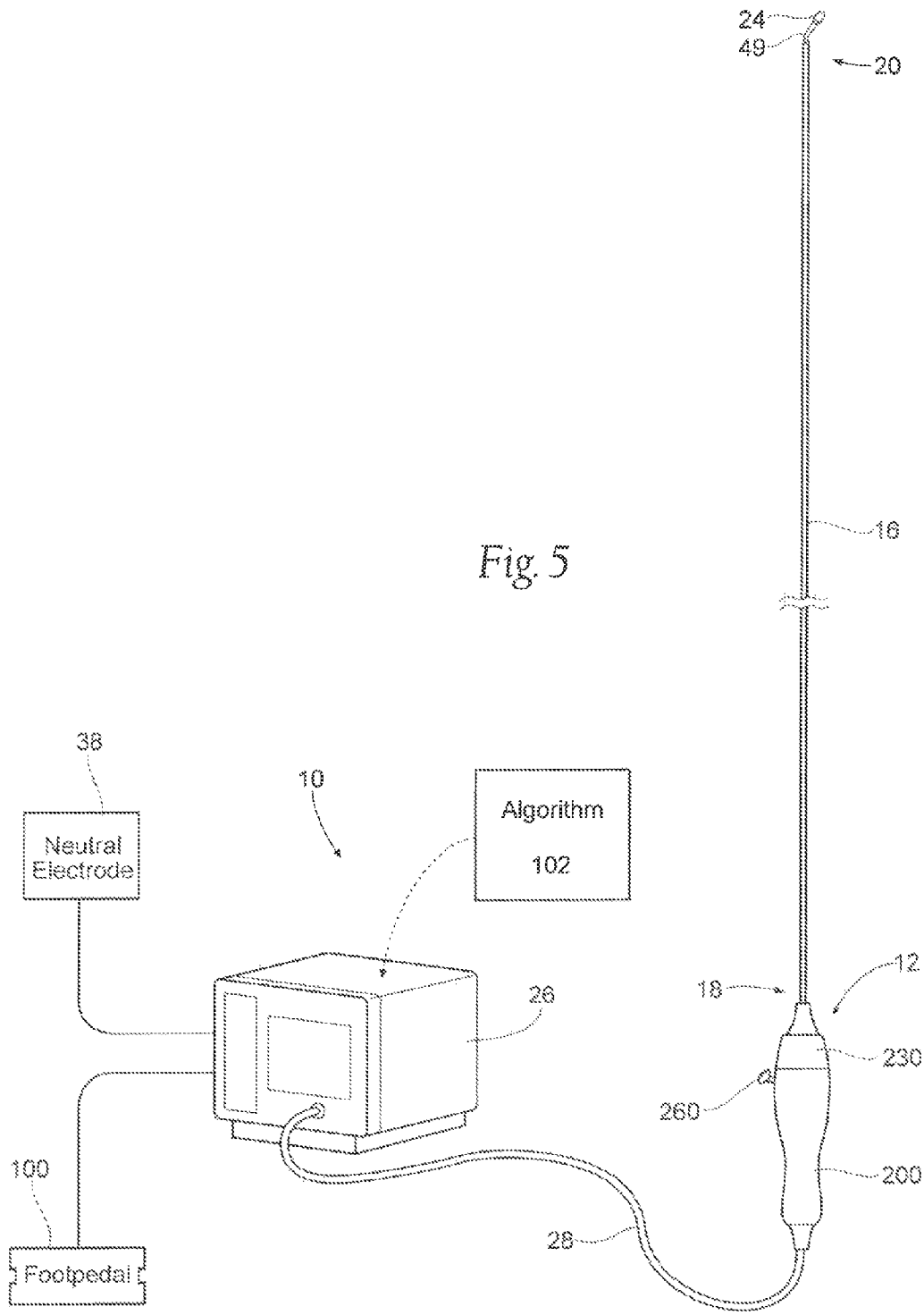

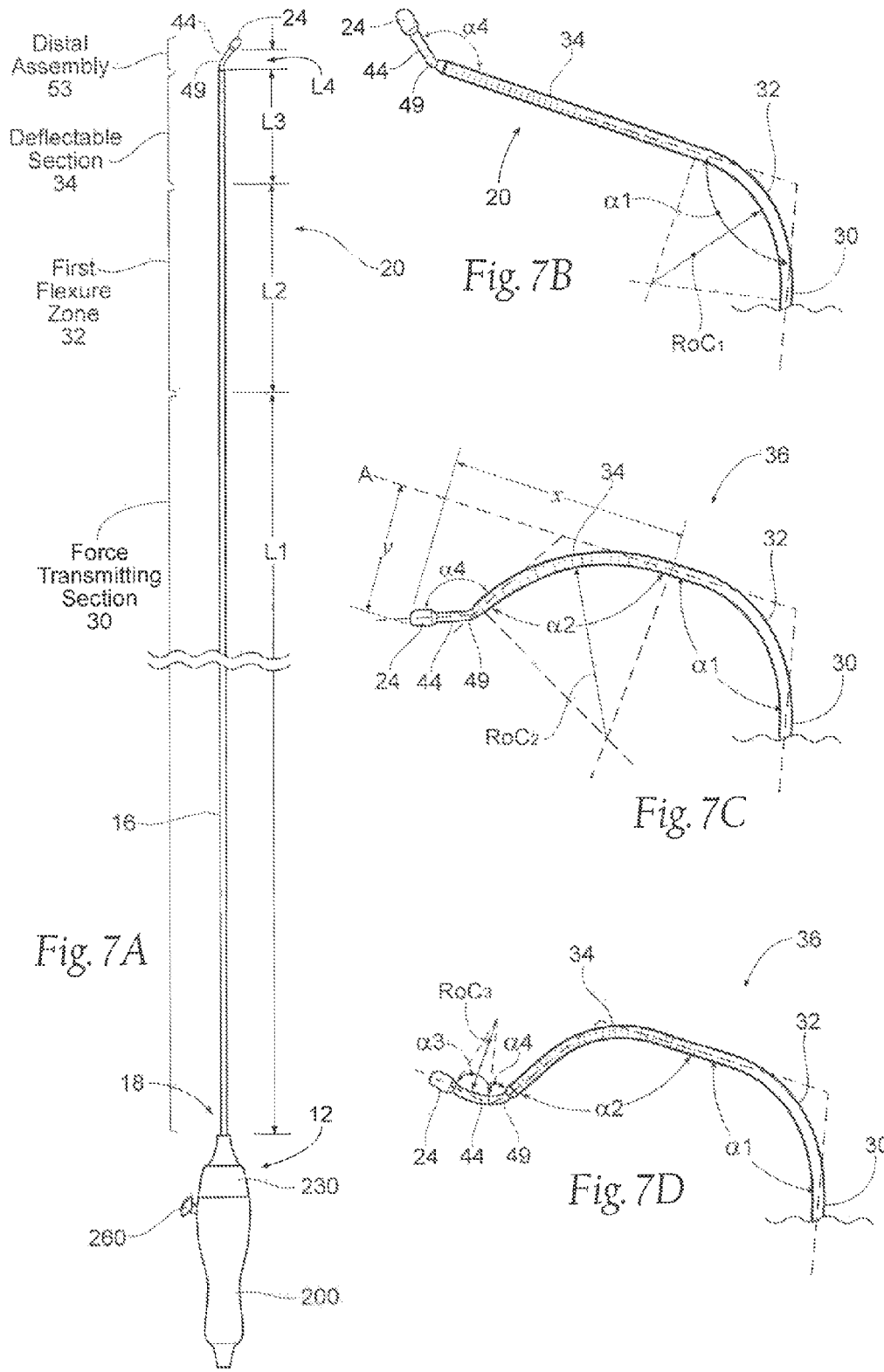

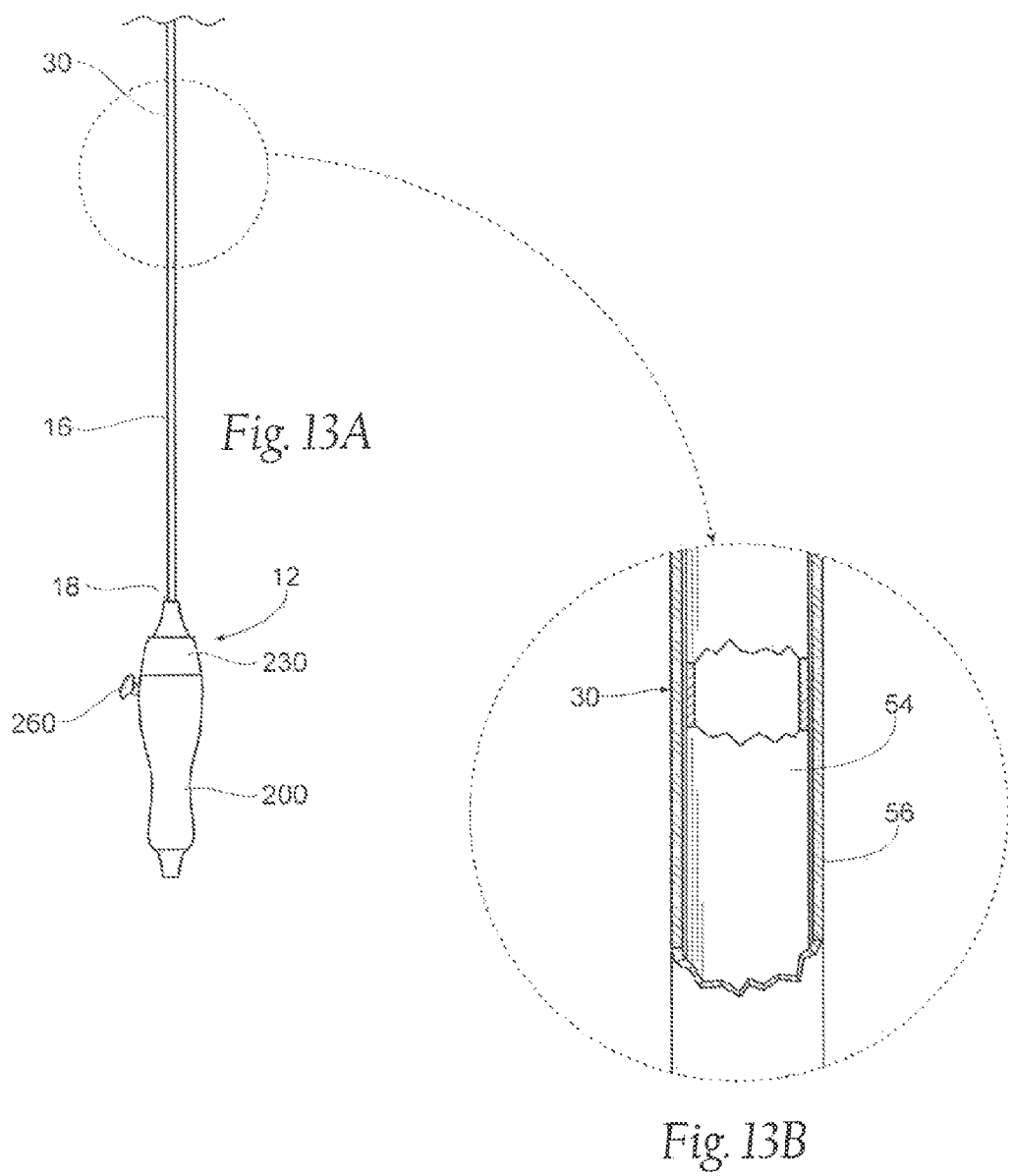

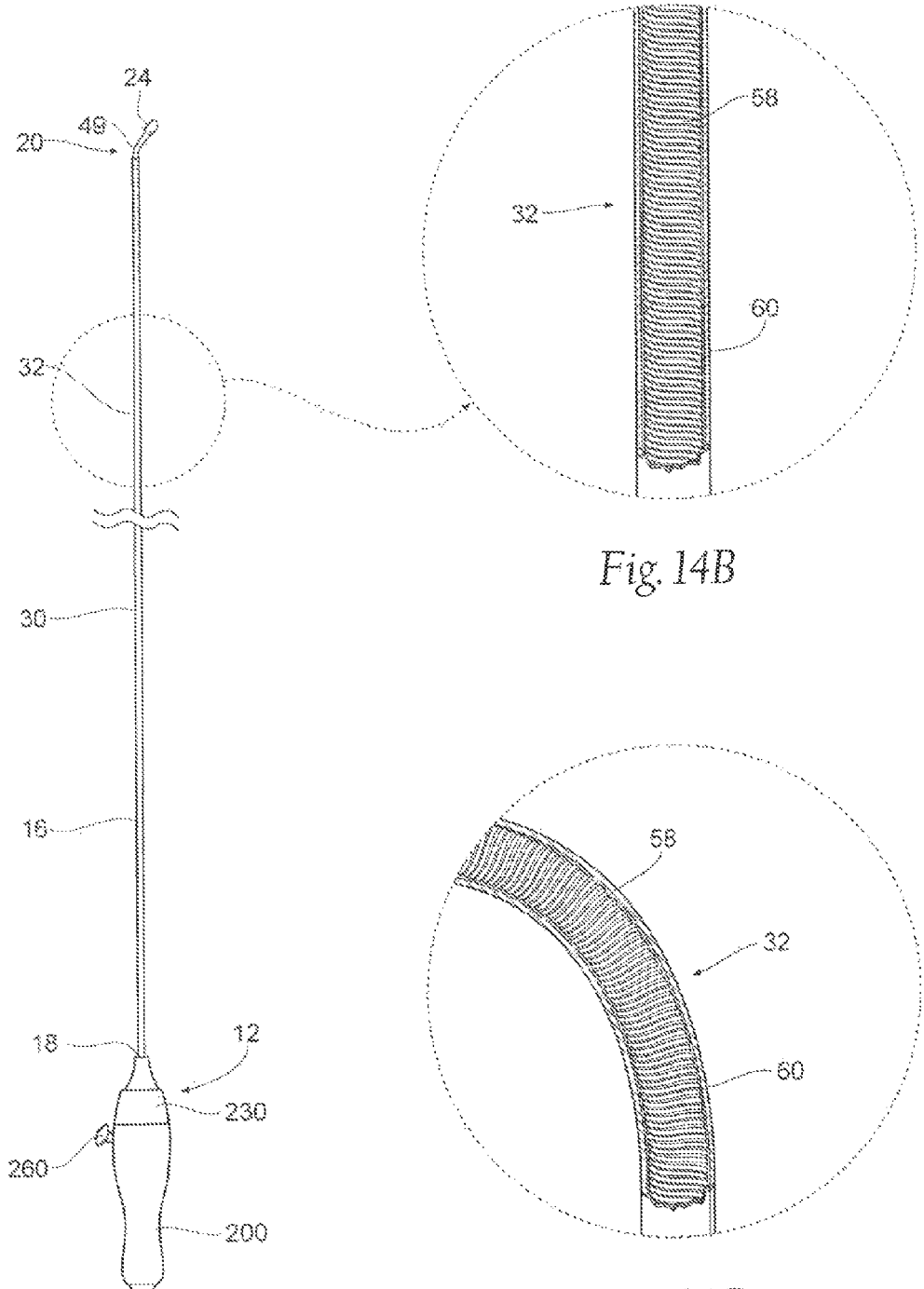

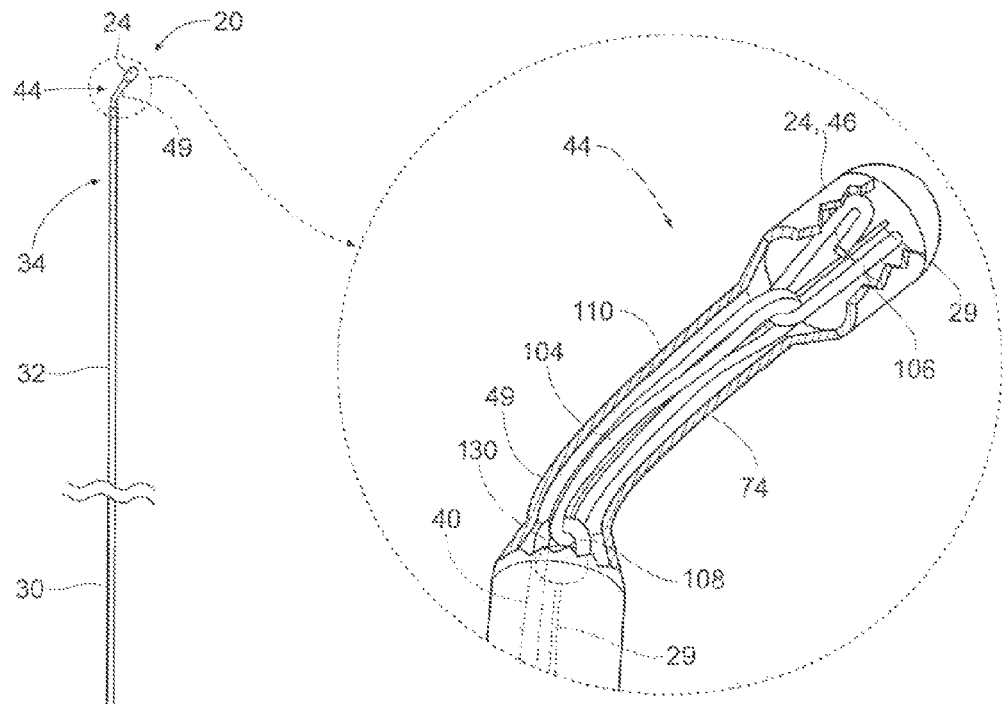
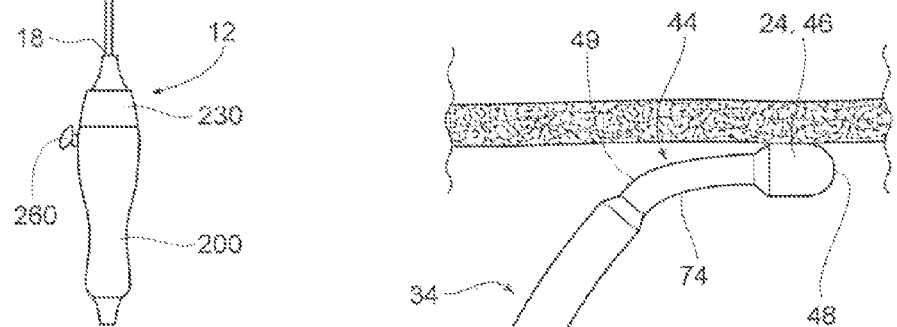
Fig. 16A
Fig. 16B
Fig. 16C

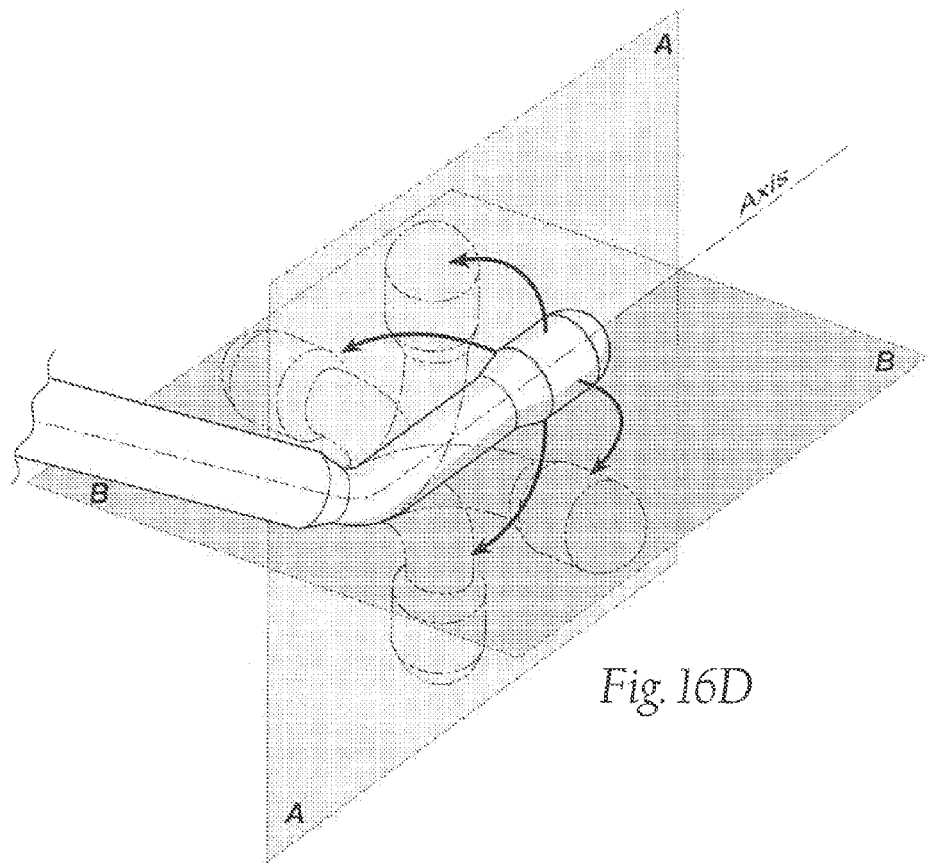
Fig. 16D
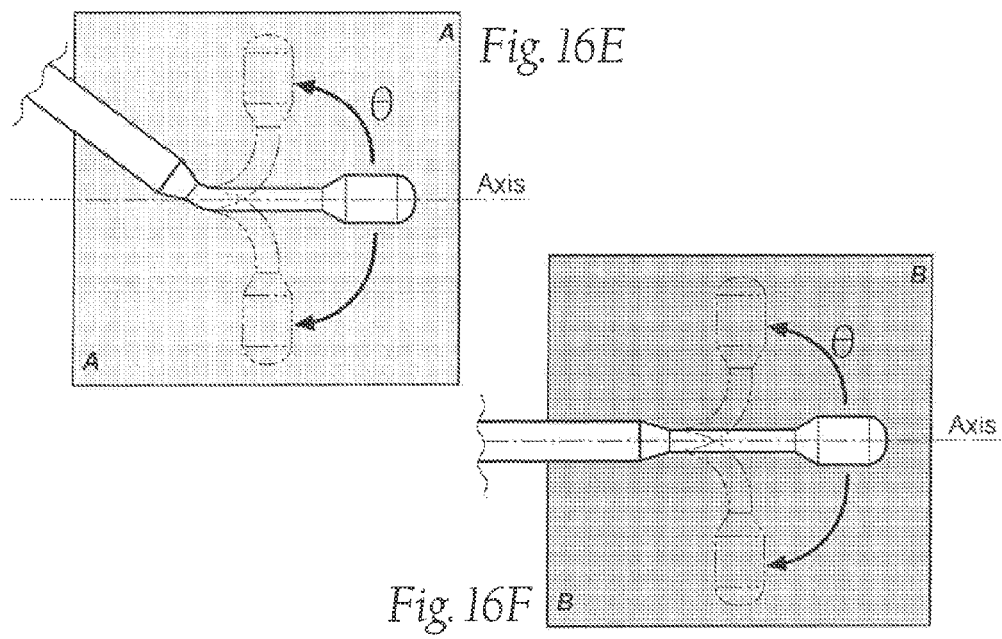
Fig. 16E
Fig. 16F

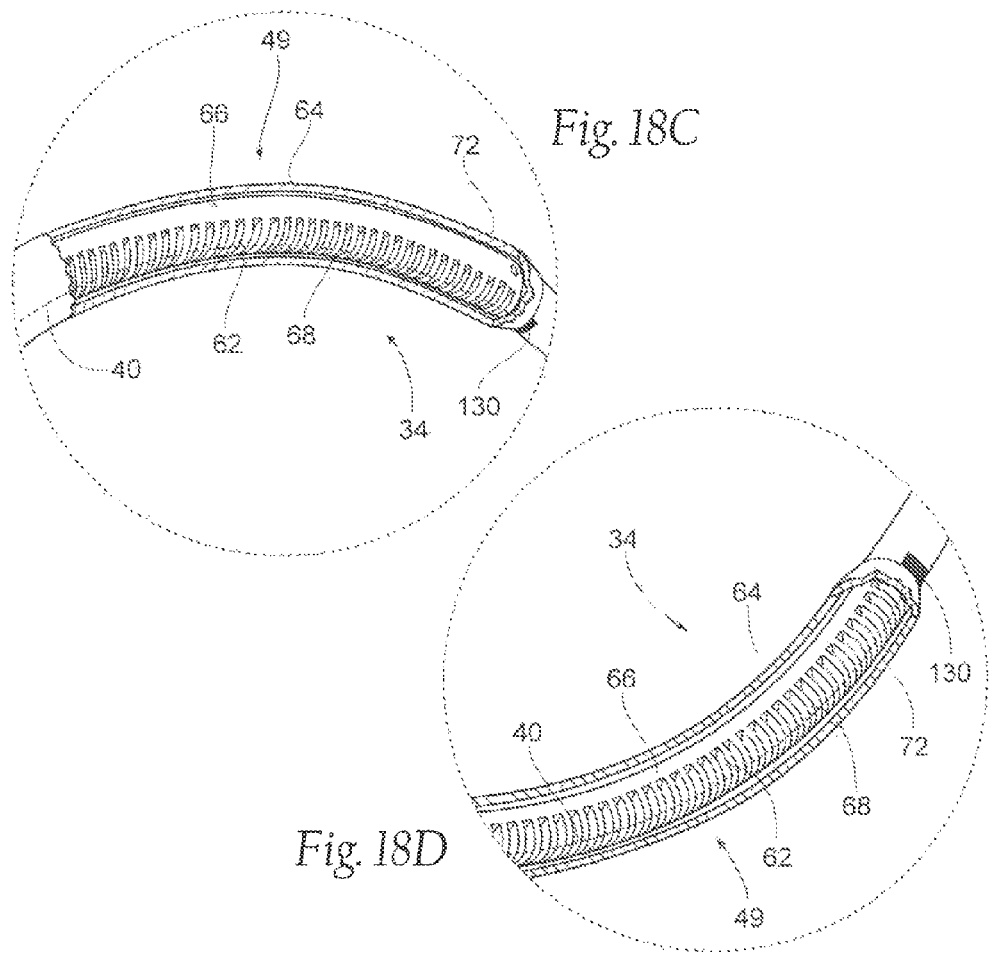
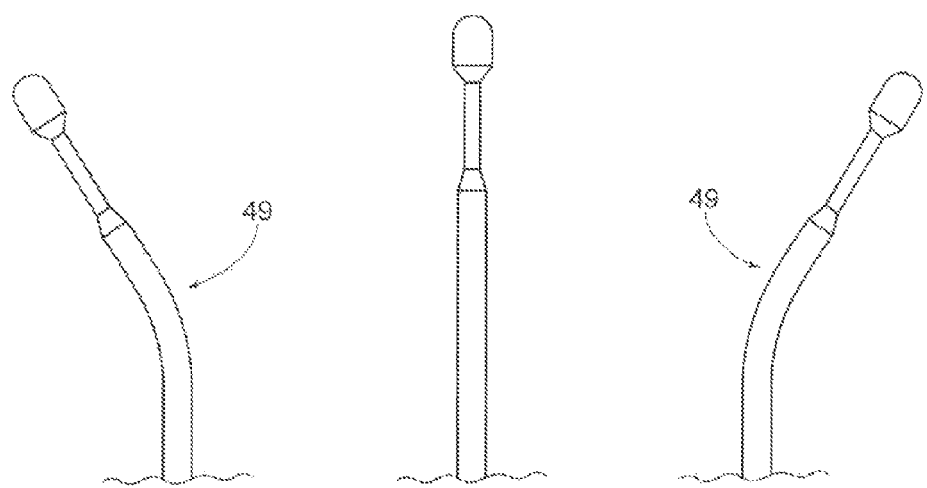
Fig. 18E    Fig. 18F    Fig. 18G

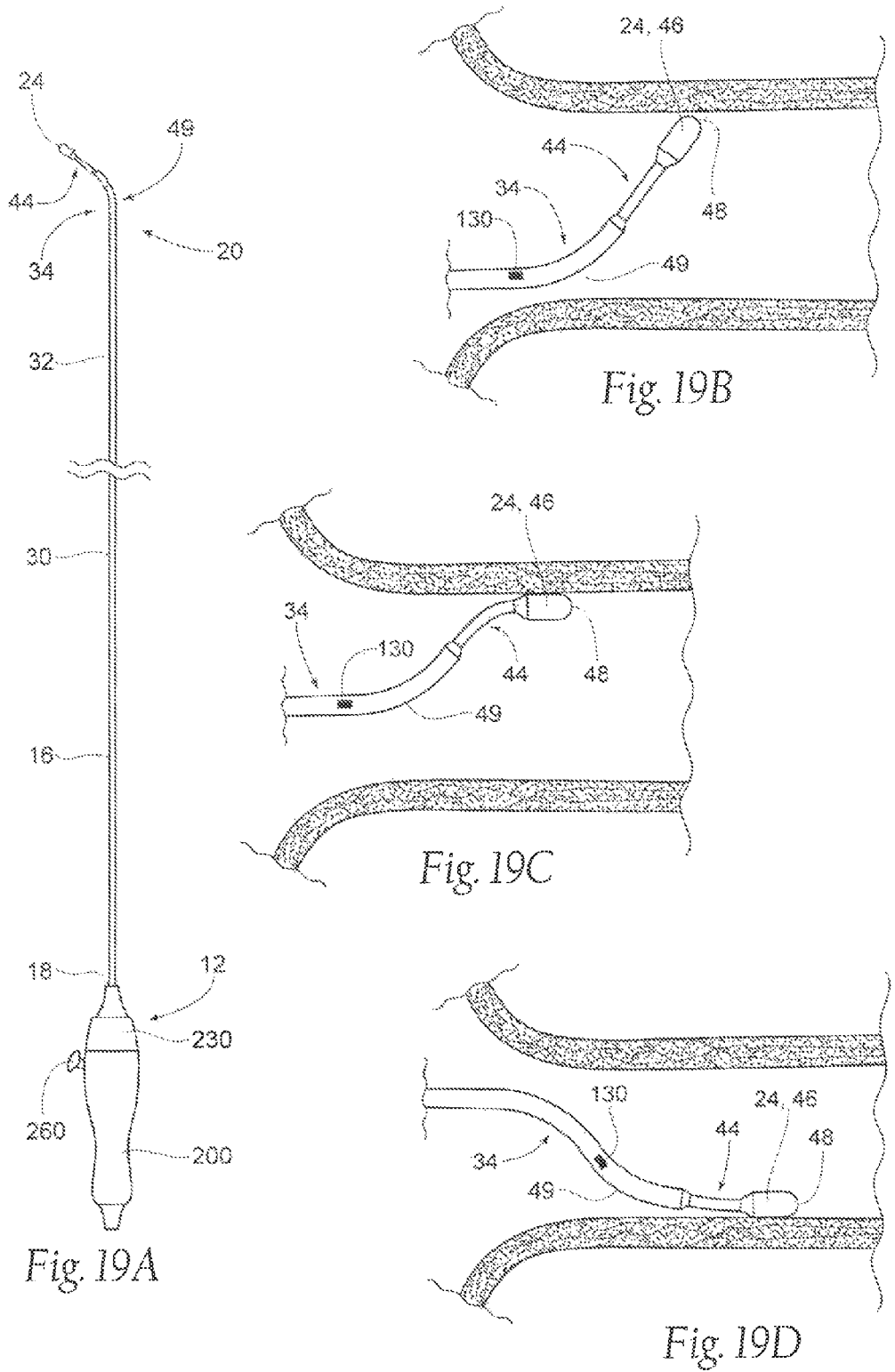

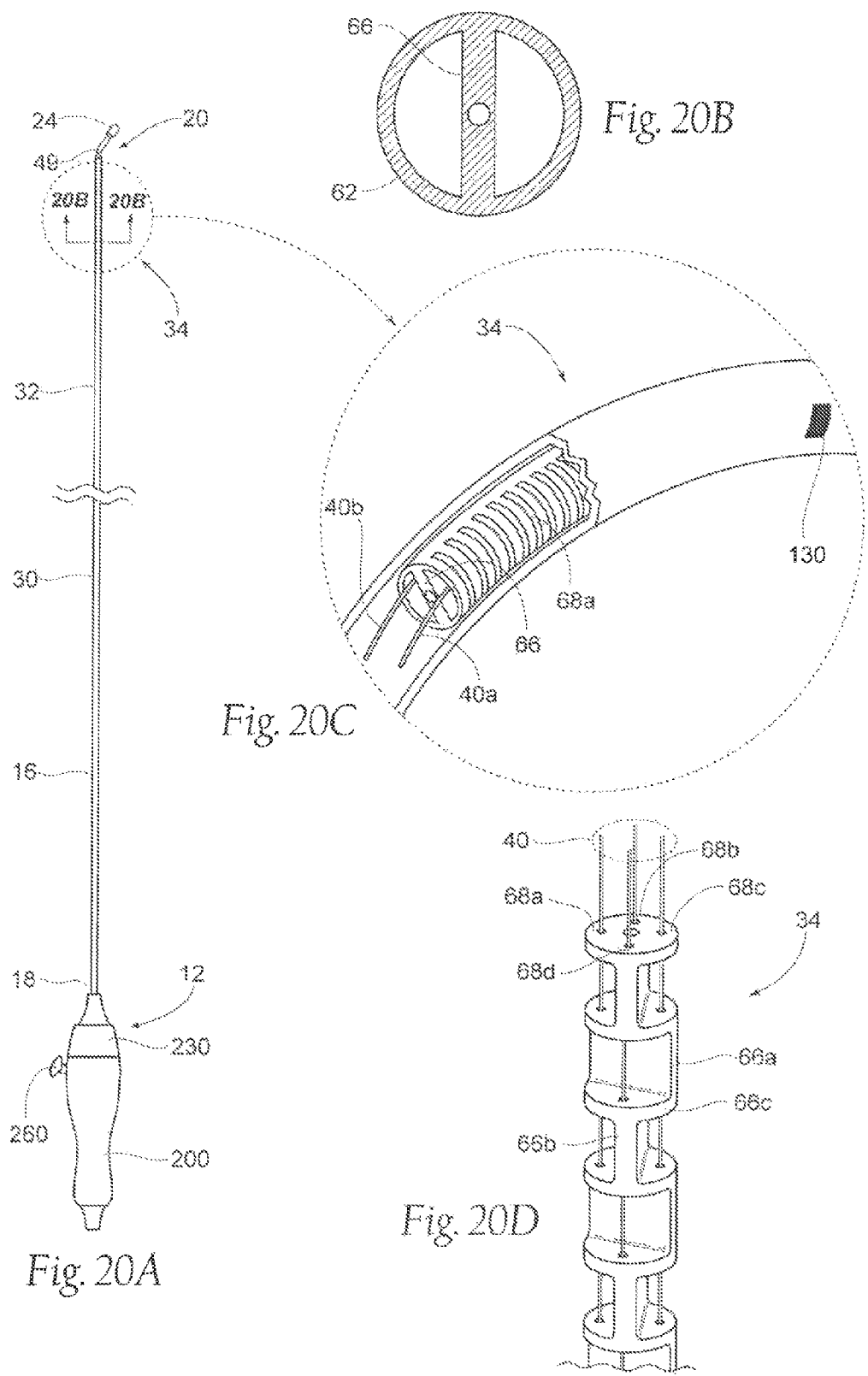

CATHETER APPARATUSES, SYSTEMS, AND METHODS FOR RENAL NEUROMODULATION

REFERENCE TO RELATED APPLICATION(S)

The present application claims the benefit of U.S. Provisional Patent Application No. 61/328,105, filed Apr. 26, 2010, and incorporated herein by reference in its entirety.

TECHNICAL FIELD

The technologies disclosed in the present application generally relate to catheter apparatuses, systems and methods for intravascular neuromodulation. More particularly, the technologies disclosed herein relate to catheter apparatuses, systems, and methods for achieving intravascular renal neuromodulation via application of thermal and/or electrical energy.

BACKGROUND

Hypertension, heart failure, chronic kidney disease, insulin resistance, diabetes and metabolic syndrome represent a significant and growing global health issue. Current therapies for these conditions include non-pharmacological, pharmacological and device-based approaches. Despite this variety of treatment options, the rates of control of blood pressure and the therapeutic efforts to prevent progression of these disease states and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions.

Reduction of sympathetic renal nerve activity (e.g., via denervation), can reverse these processes. Ardian, Inc., of Palo Alto, Calif., has discovered that an energy field, including and comprising an electric field, can initiate renal neuromodulation via denervation caused by irreversible electroporation, electrofusion, apoptosis, necrosis, ablation, thermal alteration, alteration of gene expression or another suitable modality.

Catheter-based intervention is widely used for medical treatments where access to a location in the body is obtained, for example, through a vessel of the cardiovascular system. Ardian, Inc. has shown that an energy field can be applied to the sympathetic renal nerves from within a renal artery. The renal artery has features unique from other vessels or parts of the body and thus applying an energy field to the sympathetic renal nerves from within the renal artery is not trivial. Accordingly, a need exists for a catheter capable of effectively delivering energy to the renal sympathetic nerves from within a renal artery, where the catheter is better configured to i) navigate through a renal artery with reduced risk of applying traumatic force to the artery wall; ii) precisely place an energy delivery element at a desired location on the vessel wall; and iii) maintain stable contact between the energy delivery element and the location on the vessel wall during blood flow pulsatility and respiratory motion of the renal artery.

SUMMARY

The following summary is provided for the benefit of the reader only, and is not intended to limit the disclosure in any way. The present application provides catheter apparatuses, systems and methods for achieving electrically- and/or thermally-induced renal neuromodulation by intravascular access.

One aspect of the present application provides apparatuses, systems, and methods that incorporate a catheter treatment device comprising an elongated shaft. The elongated shaft is sized and configured to deliver at least one energy delivery element to a renal artery via an intravascular path that includes a femoral artery, an iliac artery and the aorta. Different sections of the elongated shaft serve different mechanical functions when in use. The sections are differentiated in terms of their size, configuration, and mechanical properties for (i) percutaneous introduction into a femoral or brachial artery through a small-diameter access site; (ii) atraumatic passage through the tortuous intravascular path through an iliac artery, into the aorta, and into a respective left/right renal artery, including (iii) accommodating significant flexure at the junction of the left/right renal arteries and aorta to gain entry into the respective left or right renal artery; (iv) accommodating controlled translation, deflection, and/or rotation within the respective renal artery to attain proximity to and a desired alignment with an interior wall of the respective renal artery; (v) allowing the placement of at least one energy delivery element into contact with tissue on the interior wall in an orientation that optimizes the active surface area of the energy delivery element; and (vi) allowing substantially stable contact force between the at least one energy delivery element and the interior wall during motion of the renal artery with respect to the aorta due to respiration and/or blood flow pulsatility.

BRIEF DESCRIPTION OF THE DRAWINGS

FIG. 5 is a perspective view of a system for achieving intravascular, thermally-induced renal neuromodulation, comprising a treatment device and a generator.

FIGS. 7A to 7D are a series of views of the elongated shaft of the treatment device shown in FIG. 5, showing the different mechanical and functional regions that the elongated shaft incorporates.

FIGS. 13A and 13B show a representative embodiment of the force transmitting section of the elongated shaft of the treatment device shown in FIG. 5.

FIGS. 14A to 14C show a representative embodiment of the first flexure zone of the elongated shaft of the treatment device shown in FIG. 5.

FIGS. 16A to 16C show a representative embodiment of the force dampening section of the elongated shaft of the treatment device shown in FIG. 5.

FIGS. 16D to 16F show multiple planar views of the bending capability of the force dampening section corresponding to the elongated shaft of the treatment device shown in FIG. 5.

FIGS. 18A to 18G show additional alternative representative embodiments of an elongated shaft for a treatment device like that shown in FIG. 5, showing examples of the different structural, mechanical and functional regions that the elongated shaft can incorporate.

FIGS. 19A to 19D show additional alternative representative embodiments of an elongated shaft for a treatment device like that shown in FIG. 5, showing examples of the different structural, mechanical and functional regions that the elongated shaft can incorporate.

FIGS. 20A to 20D show additional alternative representative embodiments of an elongated shaft for a treatment device like that shown in FIG. 5, showing examples of the different structural, mechanical and functional regions that the elongated shaft can incorporate.

DETAILED DESCRIPTION

Figure 1:
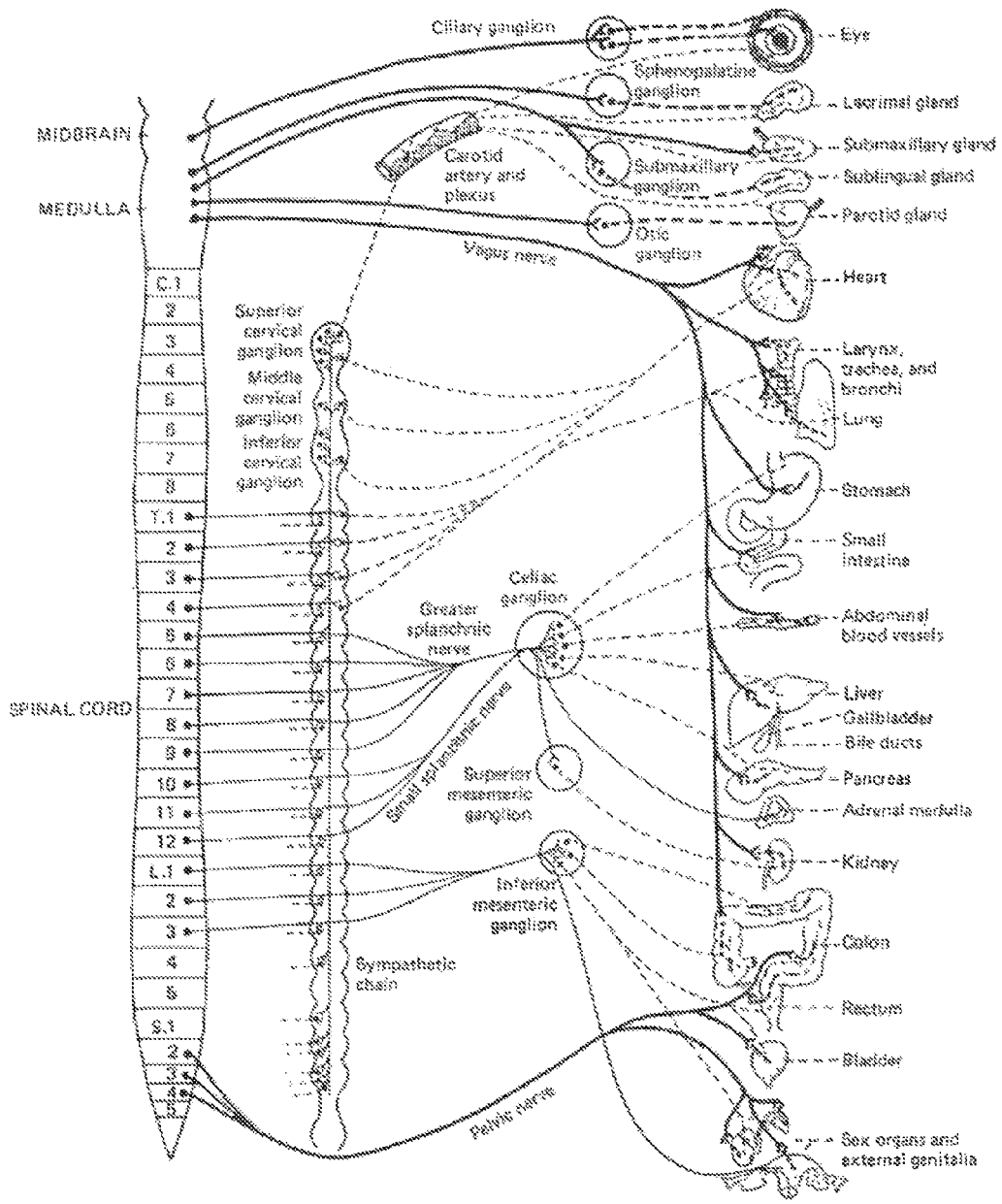
FIG. 1 is a conceptual illustration of the sympathetic nervous system (SNS) and how the brain communicates with the body via the SNS.

Although the disclosure hereof is detailed and exact to enable those skilled in the art to practice the disclosed technologies, the physical embodiments herein disclosed merely exemplify the various aspects of the invention, which may be embodied in other specific structures. While the preferred embodiment has been described, the details may be changed without departing from the invention, which is defined by the claims.

I. Pertinent Anatomy and Physiology

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation can elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

As shown in FIG. 1, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons must travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 2:
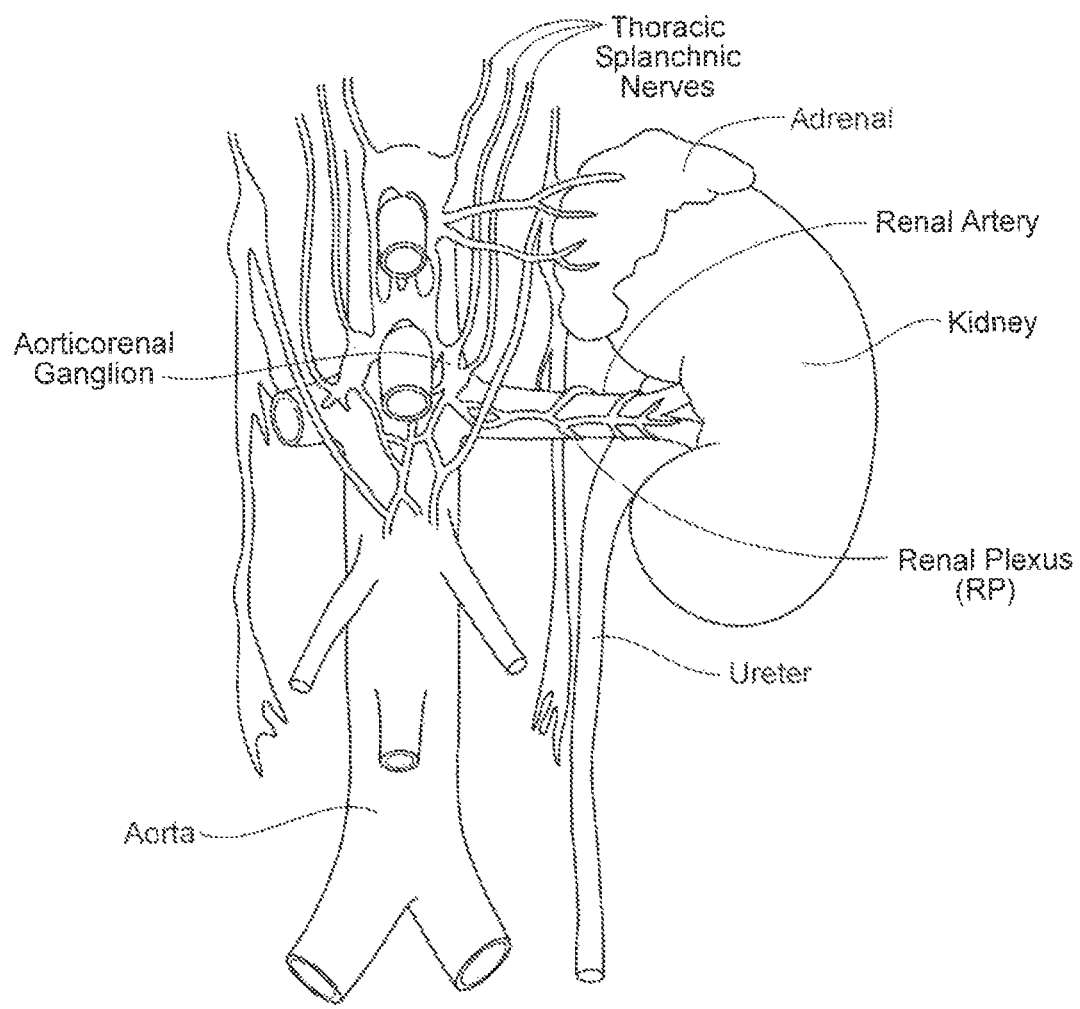
FIG. 2 is an enlarged anatomic view of nerves innervating a left kidney to form the renal plexus surrounding the left renal artery.

As FIG. 2 shows, the kidney is innervated by the renal plexus (RP), which is intimately associated with the renal artery. The renal plexus is an autonomic plexus that surrounds the renal artery and is embedded within the adventitia of the renal artery. The renal plexus extends along the renal artery until it arrives at the substance of the kidney. Fibers contributing to the renal plexus arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages can trigger changes in different parts of the body simultaneously. For example, the sympathetic nervous system can accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all cause death and death from cardiovascular disease. This is also true for patients suffering from diabetic or contrast nephropathy. There is compelling evidence that suggests that sensory afferent signals originating from the diseased kidneys are major contributors to the initiation and sustainment of elevated central sympathetic outflow in this patient group, which facilitates the occurrence of the well known adverse consequences of chronic sympathetic overactivity such as hypertension, left ventricular hypertrophy, ventricular arrhythmias, sudden cardiac death, insulin resistance, diabetes and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 3A:
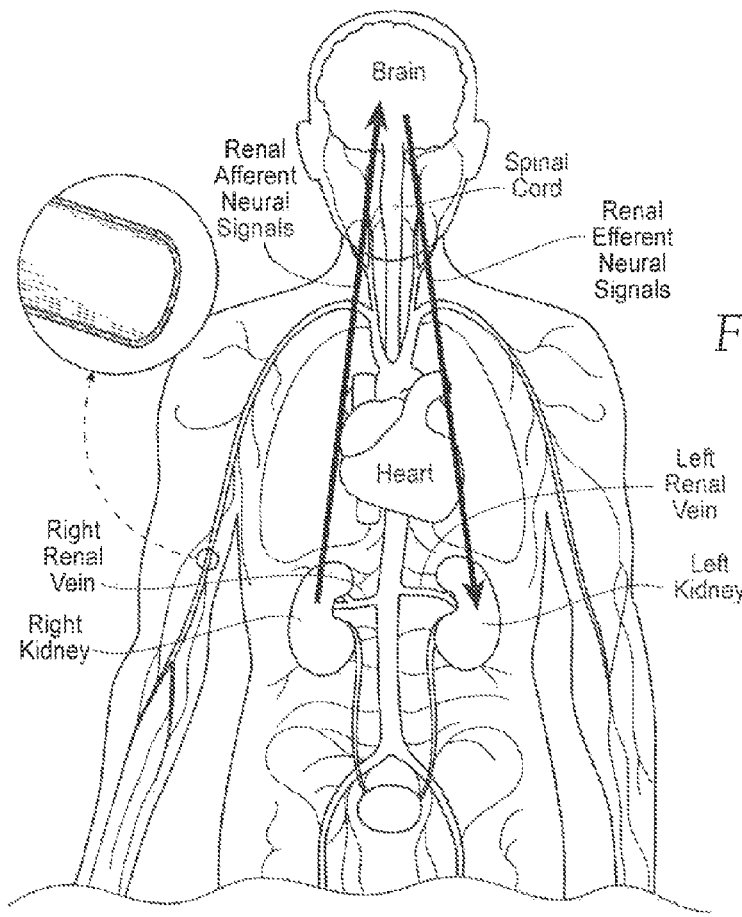
FIGS. 3A and 3B provide anatomic and conceptual views of a human body, respectively, depicting neural efferent and afferent communication between the brain and kidneys
Figure 3B:
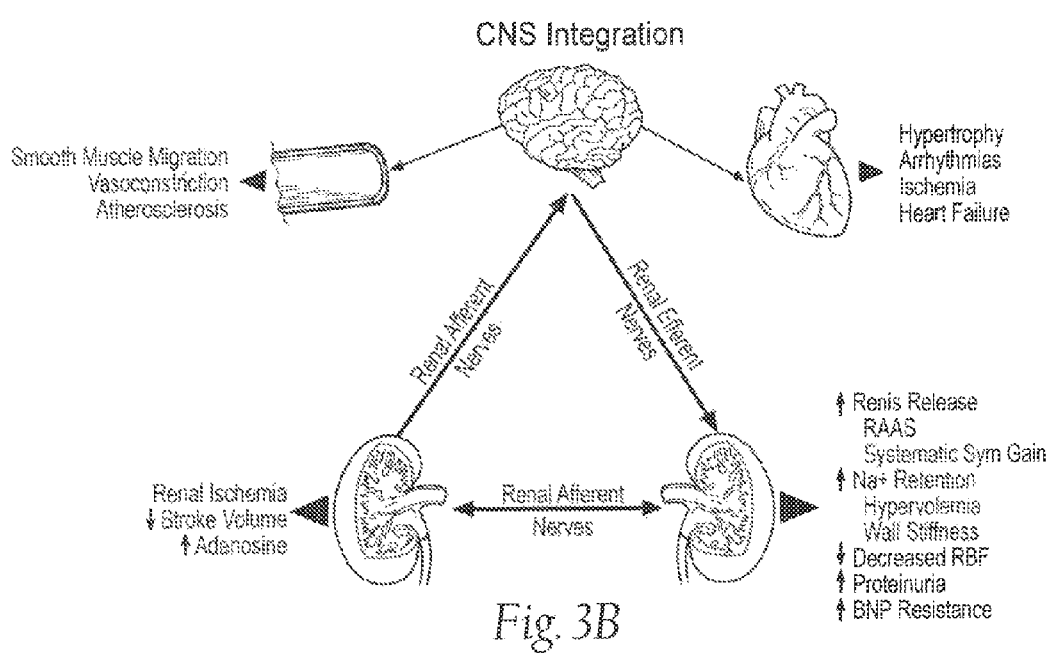

The kidneys communicate with integral structures in the central nervous system via renal sensory afferent nerves. Several forms of "renal injury" can induce activation of sensory afferent signals. For example, renal ischemia, reduction in stroke volume or renal blood flow, or an abundance of adenosine enzyme may trigger activation of afferent neural communication. As shown in FIGS. 3A and 3B, this afferent communication might be from the kidney to the brain or might be from one kidney to the other kidney (via the central nervous system). These afferent signals are centrally integrated and can result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) denervation of tissue with efferent sympathetic nerves will reduce inappropriate renin release, salt retention, and reduction of renal blood flow, and that (ii) denervation of tissue with afferent sensory nerves will reduce the systemic contribution to hypertension, and other disease states associated with increased central sympathetic tone, through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic and end stage renal disease, inappropriate fluid retention in heart failure, cardio-renal syndrome and sudden death. Since the reduction of afferent neural signals contributes to the systemic reduction of sympathetic tone/drive, renal denervation might also be useful in treating other conditions associated with systemic sympathetic hyperactivity. Accordingly, renal denervation can also benefit other organs and bodily structures innervated by sympathetic nerves, including those identified in FIG. 1. For example, a reduction in central sympathetic drive may reduce the insulin resistance that afflicts people with metabolic syndrome and Type II diabetics. Additionally, patients with osteoporosis are also sympathetically activated and might also benefit from the downregulation of sympathetic drive that accompanies renal denervation.

C. Achieving Intravascular Access to the Renal Artery

Figures 4A, 4B:
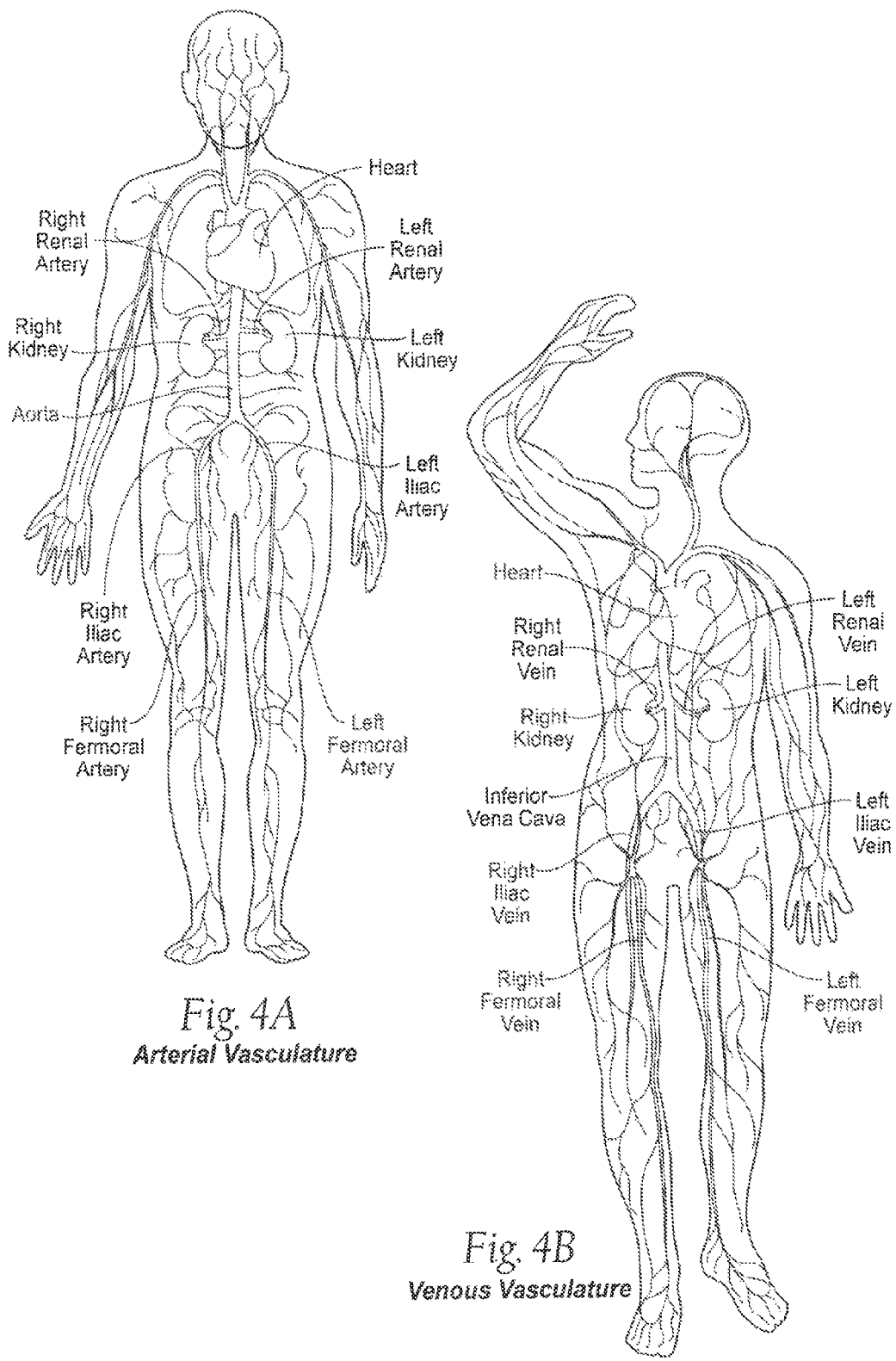
FIGS. 4A and 4B are, respectively, anatomic views of the arterial and venous vasculatures of a human.

In accordance with the present invention, neuromodulation of a left and/or right renal plexus (RP), which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed to the left atrium. From the left atrium, the oxygenated blood is conveyed by the left ventricle back to the aorta.

As will be described in greater detail later, the femoral artery can be exposed and cannulated at the base of the femoral triangle, just inferior to the midpoint of the inguinal ligament. A catheter can be inserted through this access site, percutaneously into the femoral artery and passed into the iliac artery and aorta, into either the left or right renal artery. This comprises an intravascular path that offers minimally invasive access to a respective renal artery and/or other renal blood vessels.

The wrist, upper arm, and shoulder region provide other locations for introduction of catheters into the arterial system. Catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present invention through intravascular access, properties and characteristics of the renal vasculature may impose constraints upon and/or inform the design of apparatus, systems and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained below, may have bearing on the clinical safety and efficacy of the procedure and the specific design of the intravascular device. Properties of interest may include, for example, material/mechanical, spatial, fluid dynamic/hemodynamic and/or thermodynamic properties.

As discussed previously, a catheter can be advanced percutaneously into either the left or right renal artery via a minimally invasive intravascular path. However, minimally invasive renal arterial access can be challenging, for example, because, as compared to some other arteries that are routinely accessed using catheters, the renal arteries are often extremely tortuous, may be of relatively small diameter and/or may be of relatively short length. Furthermore, renal arterial atherosclerosis is common in many patients, particularly those with cardiovascular disease. Renal arterial anatomy also may vary significantly from patient to patient, further complicating minimally invasive access. Significant interpatient variation may be seen, for example, in relative tortuosity, diameter, length and/or atherosclerotic plaque burden, as well as in the take-off angle at which a renal artery branches from the aorta. Apparatus, systems and methods for achieving renal neuromodulation via intravascular access must account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus comprises an energy delivery element, such as an electrode, consistent positioning and contact force application between the energy delivery element and the vessel wall is important for predictability and safety. However, navigation is impeded by the tight space within a renal artery, as well as tortuosity of the artery. Furthermore, respiration and/or the cardiac cycle may cause significant movement of the renal artery relative to the aorta, and the cardiac cycle and/or the neuromodulatory apparatus may transiently distend the renal artery, further complicating establishment of stable contact.

Even after accessing a renal artery and facilitating stable contact between neuromodulatory apparatus and a luminal surface of the artery, nerves in and around the adventia of the artery must be safely modulated via the neuromodulatory apparatus. Safely applying thermal treatment from within a renal artery is non-trivial given the potential clinical complications associated with such treatment. For example, the intima and media of the renal artery are highly vulnerable to thermal injury. As discussed in greater detail below, the Intima-Media Thickness separating the vessel lumen from its adventitia means that target renal nerves may be multiple millimeters distant from the luminal surface of the artery. Sufficient thermal energy must be delivered to the target renal nerves to modulate the target renal nerves without excessively heating and desiccating the vessel wall. Another potential clinical complication associated with excessive heating is thrombus formation from coagulating blood flowing through the artery. Given that this thrombus can cause a kidney infarct, thereby causing irreversible damage to the kidney, thermal treatment from within the renal artery must be applied carefully. Accordingly, the complex fluid mechanic and thermodynamic conditions present in the renal artery during treatment, particularly those that may impact heat transfer dynamics at the treatment site, can be important is applying thermal treatment from within the renal artery.

It is also desirable for the neuromodulatory apparatus to be configured to allow for adjustable positioning and repositioning of the energy delivery element within the renal artery since location of treatment may also impact clinical safety and efficacy. For example, it may be tempting to apply a full circumferential treatment from within the renal artery given that the renal nerves may be spaced circumferentially around a renal artery. However, the full-circle lesion likely resulting from a continuous circumferential treatment may create a heighten risk of renal artery stenosis, thereby negating any potential therapeutic benefit of the renal neuromodulation. Therefore, the formation of more complex lesions along a longitudinal dimension of the renal artery and/or repositioning of the neuromodulatory apparatus to multiple treatment locations may be desirable. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Based on the above described challenges of (1) renal artery intervention, (2) consistent and stable placement of the energy delivery element against the vessel wall, (3) safe application of thermal treatment across the vessel wall, and (4) positioning and repositioning the treatment apparatus to allow for multiple treatment locations, various independent and dependent properties of the renal vasculature that may be of interest include, for example, vessel diameter, length, intima-media thickness, coefficient of friction and tortuosity; distensibility, stiffness and modulus of elasticity of the vessel wall; peak systolic and end-diastolic blood flow velocity, as well as the mean systolic-diastolic peak blood flow velocity, mean/max volumetric blood flow rate; specific heat capacity of blood and/or of the vessel wall, thermal conductivity of blood and/or of the vessel wall, thermal convectivity of blood flow past a vessel wall treatment site and/or radiative heat transfer; and renal motion relative to the aorta, induced by respiration and/or blood flow pulsatility, as well as the take-off angle of a renal artery relative to the aorta. These properties will be discussed in greater detail with respect to the renal arteries. However, dependent on the apparatus, systems and methods utilized to achieve renal neuromodulation, such properties of the renal veins also may guide and/or constrain design characteristics.

Apparatus positioned within a renal artery must conform to the geometry of the artery. Renal artery vessel diameter, $D_{RA}$, typically is in a range of about 2-10 mm, with an average of about 6 mm. Renal artery vessel length, $L_{RA}$, between its ostium at the aorta/renal artery juncture and its distal branchings, generally is in a range of about 5-70 mm, more generally in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

Apparatus navigated within a renal artery also must contend with friction and tortuosity. The coefficient of friction, μ, (e.g., static or kinetic friction) at the wall of a renal artery generally is quite low, for example, generally is less than about 0.05, or less than about 0.03. Tortuosity, τ, a measure of the relative twistiness of a curved segment, has been quantified in various ways. The arc-chord ratio defines tortuosity as the length of a curve, $L_{curve}$, divided by the chord, $C_{curve}$, connecting the ends of the curve (i.e., the linear distance separating the ends of the curve):

$$\tau = L_{curve}/C_{curve} \quad (1)$$

Renal artery tortuosity, as defined by the arc-chord ratio, is generally in the range of about 1-2.

The pressure change between diastole and systole changes the luminal diameter of the renal artery, providing information on the bulk material properties of the vessel. The Distensibility Coefficient, DC, a property dependent on actual blood pressure, captures the relationship between pulse pressure and diameter change:

$$DC = 2*((D_{sys}-D_{dia})/D_{dia})/\Delta P = 2*(\Delta D/D_{dia})/\Delta P, \quad (2)$$

where $D_{sys}$ is the systolic diameter of the renal artery, $D_{dia}$ is the diastolic diameter of the renal artery, and ΔD (which generally is less than about 1 mm, e.g., in the range of about 0.1 mm to 1 mm) is the difference between the two diameters:

$$\Delta D = D_{sys} - D_{dia} \quad (3)$$

The renal arterial Distensibility Coefficient is generally in the range of about 20-50 kPa$^{-1}$*10$^{-3}$.

The luminal diameter change during the cardiac cycle also may be used to determine renal arterial Stiffness, β. Unlike the Distensibility Coefficient, Stiffness is a dimensionless property and is independent of actual blood pressure in normotensive patients:

$$\beta = (\ln[BP_{sys}/BP_{dia}])/(\Delta D/D_{dia}) \quad (4)$$

Renal arterial Stiffness generally is in the range of about 3.5-4.5.

In combination with other geometric properties of the renal artery, the Distensibility Coefficient may be utilized to determine the renal artery's Incremental Modulus of Elasticity, $E_{inc}$:

$$E_{inc} = 3(1+(LCSA/IMCSA))/DC, \quad (5)$$

where LCSA is the luminal cross-sectional area and IMCSA is the intima-media cross-sectional area:

$$LCSA = \pi(D_{dia}/2)^2 \quad (6)$$

$$IMCSA = \pi(D_{dia}/2 + IMT)^2 - LCSA \quad (7)$$

For the renal artery, LCSA is in the range of about 7-50 mm$^2$, IMCSA is in the range of about 5-80 mm$^2$, and $E_{inc}$ is in the range of about 0.1-0.4 kPa*10$^3$.

For patients without significant Renal Arterial Stenosis (RAS), peak renal artery systolic blood flow velocity, $\upsilon_{max-sys}$, generally is less than about 200 cm/s; while peak renal artery end-diastolic blood flow velocity, $\upsilon_{max-dia}$, generally is less than about 150 cm/s, e.g., about 120 cm/s.

In addition to the blood flow velocity profile of a renal artery, volumetric flow rate also is of interest. Assuming Poiseulle flow, the volumetric flow rate through a tube, Φ, (often measured at the outlet of the tube) is defined as the average velocity of fluid flow through the tube, $\tau_{avg}$, times the cross-sectional area of the tube:

$$\Phi = \upsilon_{avg} * \pi R^2 \quad (8)$$

By integrating the velocity profile (defined in Eq. 10 above) over all r from 0 to R, it can be shown that:

$$\Phi = \upsilon_{avg} * \pi R^2 = (\pi R^4 * \Delta Pr)/8\eta\Delta x \quad (9)$$

As discussed previously, for the purposes of the renal artery, η may be defined as $\eta_{blood}$, Δx may be defined as $L_{RA}$, and R may be defined as $D_{RA}/2$. The change in pressure, ΔPr, across the renal artery may be measured at a common point in the cardiac cycle (e.g., via a pressure-sensing guidewire) to determine the volumetric flow rate through the renal artery at the chosen common point in the cardiac cycle (e.g. during systole and/or during enddiastole). Volumetric flow rate additionally or alternatively may be measured directly or may be determined from blood flow velocity measurements. The volumetric blood flow rate through a renal artery generally is in the range of about 500-1000 mL/min.

Thermodynamic properties of the renal artery also are of interest. Such properties include, for example, the specific heat capacity of blood and/or of the vessel wall, thermal conductivity of blood and/or of the vessel wall, thermal convectivity of blood flow past a vessel wall treatment site. Thermal radiation also may be of interest, but it is expected that the magnitude of conductive and/or convective heat transfer is significantly higher than the magnitude of radiative heat transfer.

The heat transfer coefficient may be empirically measured, or may be calculated as a function of the thermal conductivity, the vessel diameter and the Nusselt Number. The Nusselt Number is a function of the Reynolds Number and the Prandtl Number. Calculation of the Reynolds Number takes into account flow velocity and rate, as well as fluid viscosity and density, while calculation of the Prandtl Number takes into account specific heat, as well as fluid viscosity and thermal conductivity. The heat transfer coefficient of blood flowing through the renal artery is generally in the range of about 500-6000 W/m$^2$K.

An additional property of the renal artery that may be of interest is the degree of renal motion relative to the aorta, induced by respiration and/or blood flow pulsatility. A patient's kidney, located at the distal end of the renal artery, can move as much as 5 cm cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

These and other properties of the renal vasculature may impose constraints upon and/or inform the design of apparatus, systems and methods for achieving renal neuromodulation via intravascular access. Specific design requirements may include accessing the renal artery, facilitating stable contact between neuromodulatory apparatus and a luminal surface or wall of the renal artery, and/or safely modulating the renal nerves with the neuromodulatory apparatus.

II. Catheter Apparatuses, Systems and Methods for Renal Neuromodulation

A. Overview

FIG. 5 shows a system 10 for thermally inducing neuromodulation of a left and/or right renal plexus (RP) through intravascular access.

As just described, the left and/or right renal plexus (RP) surrounds the respective left and/or right renal artery. The renal plexus (RP) extends in intimate association with the respective renal artery into the substance of the kidney. The system thermally induces neuromodulation of a renal plexus (RP) by intravascular access into the respective left or right renal artery.

Figure 6A:
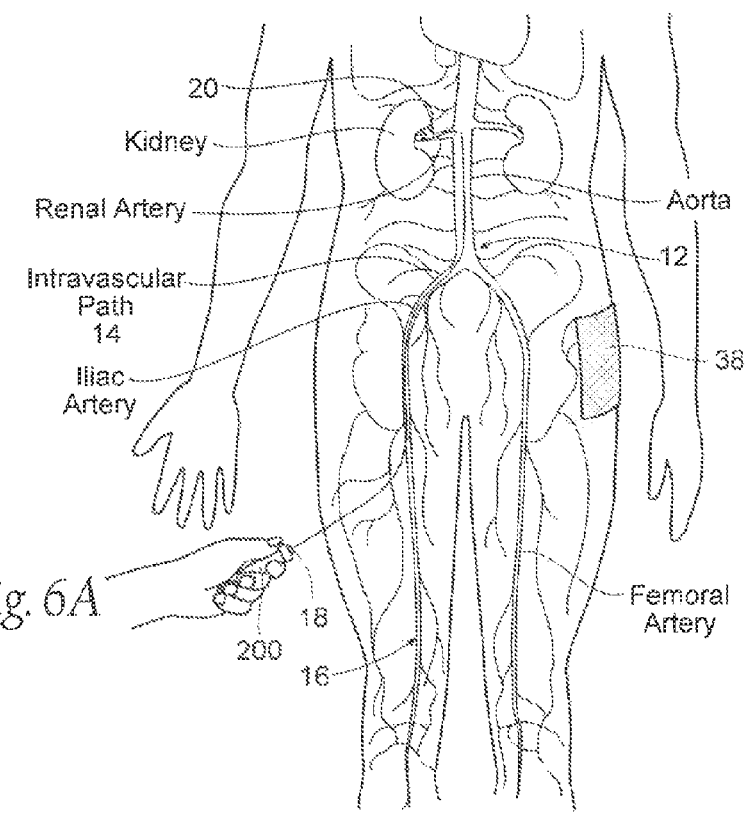
FIGS. 6A to 6C are anatomic views of the intravascular delivery, deflection and placement of various embodiments of the treatment device shown in FIG. 5 through the femoral artery and into a renal artery.

The system 10 includes an intravascular treatment device 12. The treatment device 12 provides access to the renal plexus (RP) through an intravascular path 14 that leads to a respective renal artery, as FIG. 6A shows.

As FIG. 5 shows, the treatment device 12 includes an elongated shaft 16 having a proximal end region 18 and a distal end region 20.

The proximal end region 18 of the elongated shaft 16 is optionally connected to a handle assembly 200. The handle assembly 200 is sized and configured to be securely or ergonomically held and manipulated by a caregiver (see, e.g., FIG. 17A) outside an intravascular path 14 (see, e.g., FIG. 6A). By manipulating the handle assembly 200 from outside the intravascular path 14, the caregiver can advance the elongated shaft 16 through the tortuous intravascular path 14 and remotely manipulate or actuate the distal end region 20. Image guidance, e.g., CT, radiographic, IVUS, OCT or another suitable guidance modality, or combinations thereof, can be used to aid the caregiver's manipulation.

Figure 6B:
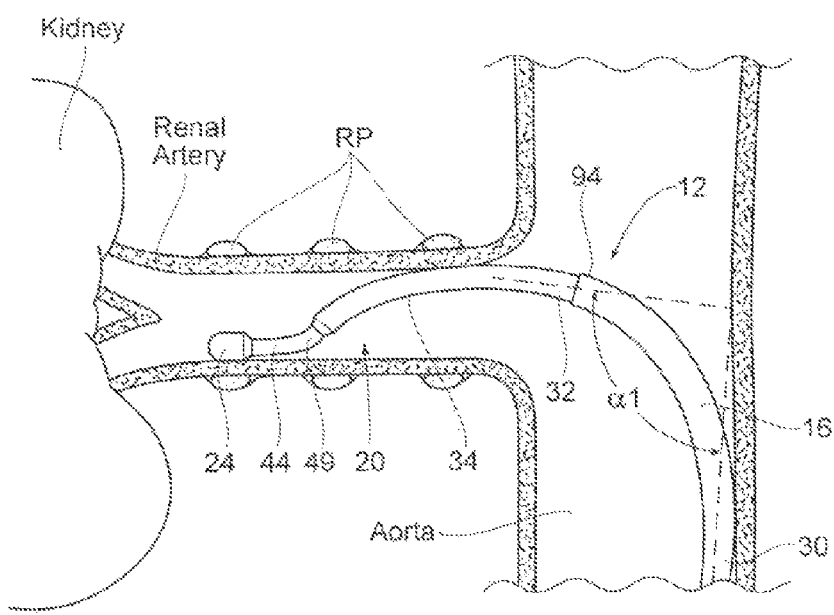
Figure 24A:
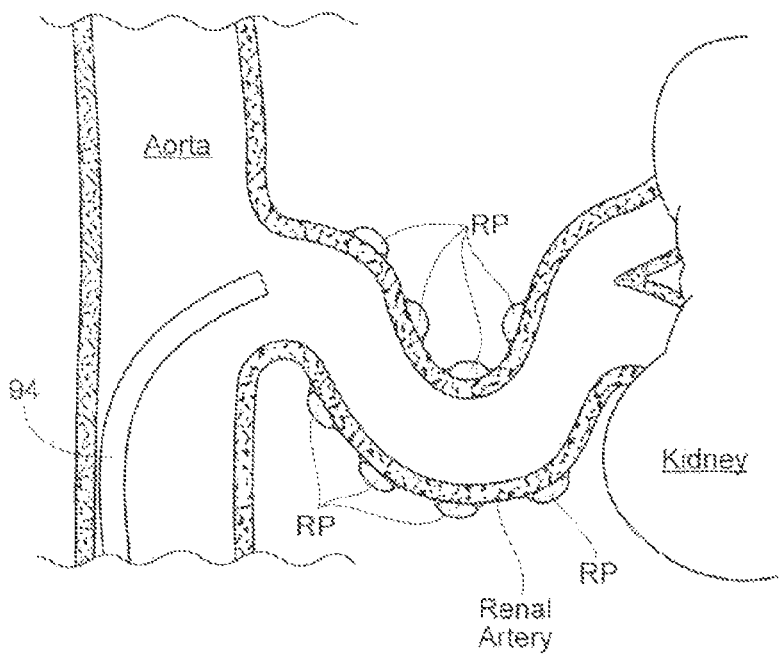
FIGS. 24A to 24H show the intravascular delivery, placement, deflection, rotation, retraction, repositioning and use of a treatment device, like that shown in FIG. 5, to achieve thermally-induced renal neuromodulation from within a renal artery.
Figure 24B:
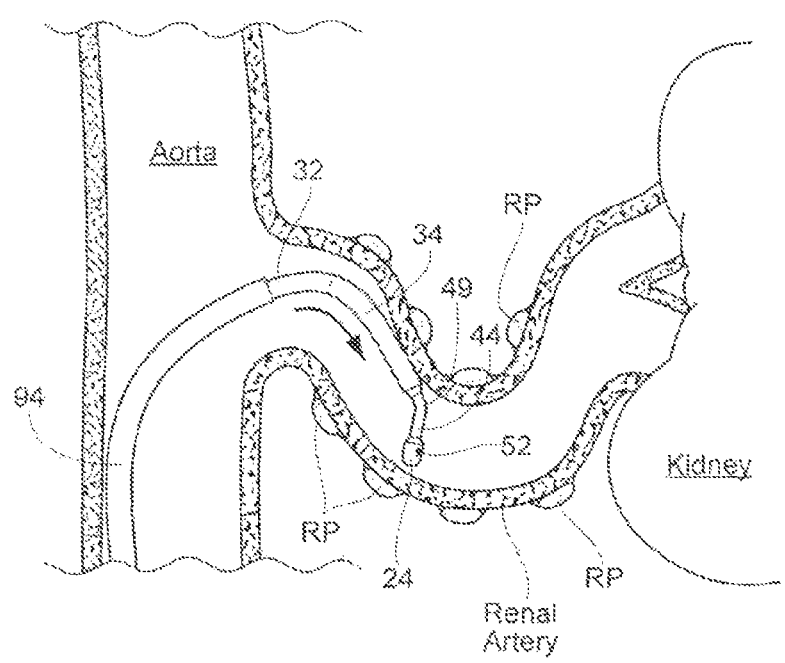

As shown in FIG. 6B, the distal end region 20 of the elongated shaft 16 can flex in a substantial fashion to gain entrance into a respective left/right renal artery by manipulation of the elongated shaft 16. As shown in FIGS. 24A and 24B, the distal end region 20 of the elongated shaft 16 can gain entrance to the renal artery via passage within a guide catheter 94. The distal end region 20 of the elongated shaft 16 carries at least one energy delivery element 24 (e.g., radiofrequency electrode, electrode, cooled radiofrequency electrode, thermal element, thermal heating element, electrically resistive heating element, cryoablation applicator, microwave antenna, ultrasound transducer, high intensity focused ultrasound transducer, laser emitter). The energy delivery element 24 is also specially sized and configured for manipulation and use within a renal artery.

As FIG. 6B shows (and as will be described in greater detail later), once entrance to a renal artery is gained, further manipulation of the distal end region 20 and the energy delivery element 24 within the respective renal artery establishes proximity to and alignment between the energy delivery element(s) 24 and tissue along an interior wall of the respective renal artery. In some embodiments, manipulation of the distal end region 20 will also facilitate contact between the energy delivery element 24 and a wall of the renal artery. In the context of the present application, the phrasing "contact between an energy delivery element and a wall of the renal artery" generally means contiguous physical contact with or without atraumatic distension of the renal artery wall and without puncturing or perforating the renal artery wall.

As also will be described in greater detail later, different sections of the elongated shaft 16 serve different mechanical functions when in use. The sections are thereby desirably differentiated in terms of their size, configuration and mechanical properties for (i) percutaneous introduction into a femoral artery through a small-diameter access site; (ii) atraumatic passage through the tortuous intravascular path 14 through an iliac artery, into the aorta, and into a respective left/right renal artery, including (iii) significant flexure near the junction of the left/right renal arteries and aorta to gain entry into the respective left or right renal artery; (iv) controlled translation, deflection, rotation and/or actuation within the respective renal artery to attain proximity to and a desired alignment with an interior wall of the respective renal artery; (v) the placement of at least one energy delivery element 24 into contact with tissue on the interior wall; (vi) allowing substantially stable contact force between the at least one energy delivery element and the interior wall during motion of the renal artery with respect to the aorta due to respiration and/or blood flow pulsatility; and (vii) repositioning via retraction and/or rotation within the renal artery for subsequent treatment(s).

Referring back to FIG. 5, the system 10 also includes an energy generator 26 (e.g., a radiofrequency generator). Under the control of the caregiver or automated control algorithm 102 (as will be described in greater detail later), the generator 26 generates a selected form and magnitude of energy. A cable 28 operatively attached to the handle assembly 200 electrically connects the energy delivery element 24 to the generator 26. At least one supply wire (not shown) passing along the elongated shaft 16 or through a lumen in the elongated shaft 16 from the handle assembly 200 to the energy delivery element 24 conveys the treatment energy to the energy delivery element 24. A control mechanism, such as foot pedal 100, can be connected (e.g., pneumatically connected or electrically connected) to the generator 26 to allow the operator to initiate, terminate and, optionally, adjust various operational characteristics of the generator, including, but not limited to, power delivery.

For systems that provide for the delivery of a monopolar electric field via the energy delivery element 24, a neutral or dispersive electrode 38 can be electrically connected to the generator 26 and attached to the exterior of the patient. Additionally, one or more sensors 52 (see, e.g., FIGS. 12 and 24), such as one or more temperature (e.g., thermocouple, thermistor, etc.), impedance, pressure, optical, flow, chemical or other sensors, can be located proximate to or within the energy delivery element and connected to one or more of the supply wires. For example, a total of two supply wires can be included, in which both wires could transmit the signal from the sensor and one wire could serve dual purpose and also convey the energy to the energy delivery element. Alternatively, both wires could transmit energy to the energy delivery element.

Once proximity between, alignment with, and contact between the energy delivery element 24 and tissue are established within the respective renal artery (as FIG. 6B shows), the purposeful application of energy from the generator 26 to tissue by the energy delivery element 24 induces one or more desired neuromodulating effects on localized regions of the renal artery and adjacent regions of the renal plexus (RP), which lay intimately within or adjacent to the adventitia of the renal artery. The purposeful application of the neuromodulating effects can achieve neuromodulation along all or a portion of the RP.

The neuromodulating effects can include thermal ablation, non-ablative thermal alteration or damage (e.g., via sustained heating and/or resistive heating), and electromagnetic neuromodulation. Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration. Desired electromagnetic neuromodulation effects may include altering the electrical signals transmitted in a nerve.

Further details of special size, configuration, and mechanical properties of the elongated shaft 16, the distal end region 20 and the energy delivery element 24, as well as other aspects of the system 10, will now be described. In still other embodiments, the system 10 may have a different configuration and/or include different features. For example, alternative multi-energy delivery element devices, such as multi-electrode baskets, spirals or lassos, or balloon expandable devices, may be implemented to intravascularly deliver neuromodulatory treatment with or without contacting the vessel wall.

B. Size and Configuration of the Elongated Shaft for Achieving Intravascular Access to a Renal Artery As explained above, intravascular access to an interior of a renal artery can be achieved, for example, through the femoral artery. As FIG. 6A shows, the elongated shaft 16 is specially sized and configured to accommodate passage through this intravascular path 14, which leads from a percutaneous access site in the femoral artery to a targeted treatment site within a renal artery. In this way, the caregiver is able to orient the energy delivery element 24 within the renal artery for its intended purpose.

For practical purposes, the maximum outer dimension (e.g., diameter) of any section of the elongated shaft 16, including the energy delivery element 24 it carries, is dictated by the inner diameter of the guide catheter or delivery catheter through which the elongated shaft 16 is passed. Assuming, for example, that an 8 French guide catheter (which has an inner diameter of approximately 0.091 inches) would likely be, from a clinical perspective, the largest guide catheter used to access the renal artery, and allowing for a reasonable clearance tolerance between the energy delivery element 24 and the guide catheter, the maximum outer dimension can be realistically expressed as being less than or equal to approximately 0.085 inches. However, use of a smaller 5 French guide catheter 94 may require the use of smaller outer diameters along the elongated shaft 16. For example, an energy delivery element 24 that is to be routed within a 5 French guide catheter would have an outer dimension of no greater than 0.053 inches. In another example, an energy delivery element 24 that is to be routed within a 6 French guide catheter would have an outer dimension of no greater than 0.070 inches.

1. Force Transmitting Section

As FIG. 7A shows, the proximal end region 18 of the elongated shaft 16 includes, coupled to the handle assembly 200, a force transmitting section 30. The force transmitting section 30 is sized and configured to possess selected mechanical properties that accommodate physical passage through and the transmission of forces within the intravascular path 14, as it leads from the accessed femoral artery (left or right), through the respective iliac branch artery and into the aorta, and in proximity to the targeted renal artery (left or right). The mechanical properties of the force transmitting section 30 include at least a preferred effective length (expressed in inches or centimeters). It should be understood that the term force transmitting section can be used interchangeably with elongated tubular shaft or proximal force transmitting section.

As FIG. 7A shows, the force transmitting section 30 includes a preferred effective length L1. The preferred effective length L1 is a function of the anatomic distance within the intravascular path 14 between the access site and a location proximate to the junction of the aorta and renal arteries. The preferred effective length L1 can be derived from textbooks of human anatomy, augmented by a caregiver's knowledge of the targeted site generally or as derived from prior analysis of the particular morphology of the targeted site. The preferred effective length L1 is also dependent on the length of the guide catheter that is used, if any. In a representative embodiment, for a normal human, the preferred effective length L1 comprises about 30 cm to about 110 cm. If no guide catheter is used, then the preferred effective length L1 comprises about 30 cm to about 35 cm. If a 55 cm length guide catheter is used, then the preferred effective length L1 comprises about 65 cm to about 70 cm. If a 90 cm length guide catheter is used, then the preferred effective length L1 comprises about 95 cm to about 105 cm.

The force transmitting section 30 also includes a preferred axial stiffness and a preferred torsional stiffness. The preferred axial stiffness expresses the capability of the force transmitting section 30 to be advanced or withdrawn along the length of the intravascular path 14 without buckling or substantial deformation. Since some axial deformation is necessary for the force transmitting section 30 to navigate the tortuous intravascular path 14 without providing too much resistance, the preferred axial stiffness of the force transmitting section should also provide this capability. The preferred torsional stiffness expresses the capability of the force transmitting section 30 to rotate the elongated shaft 16 about its longitudinal axis along its length without kinking or permanent deformation. As will be described in greater detail later, the ability to advance and retract, as well as rotate, the distal end region 20 of the elongated shaft 16 within the respective renal artery is desirable.

The desired magnitude of axial stiffness and rotational stiffness for the force transmitting section 30 can be obtained by selection of constituent material or materials to provide a desired elastic modulus (expressed in terms, e.g., of a Young's Modulus (E)) indicative of axial and torsional stiffnesses, as well as selecting the construct and configuration of the force transmitted section in terms of, e.g., its interior diameter, outer diameter, wall thickness, and structural features, including cross-sectional dimensions and geometry. Representative examples are described in greater detail below.

2. First Flexure Zone

As FIGS. 7A and 7B show, the distal end region 20 of the elongated shaft 16 is coupled to the force transmitting section 30. The length L1 of the force transmitting section 30 generally serves to bring the distal end region 20 into the vicinity of the junction of the respective renal artery and aorta (as FIG. 6B shows). The axial stiffness and torsional stiffness of the force transmitting region transfer axial and rotation forces from the handle assembly 200 to the distal end region 20, as will be described in greater detail later. It should be understood that the term first flexure zone can be used interchangeably with flexible tubular structure.

As shown in FIG. 7B, the distal end region 20 includes a first flexure zone 32 proximate to the force transmitting section 30. The first flexure zone 32 is sized and configured to have mechanical properties that accommodate significant flexure or bending at a prescribed preferred access angle α1 and provide for the transmission of torque during rotation, without fracture, collapse, substantial distortion, or significant twisting of the elongated shaft 16. The first flexure zone 32 should accommodate flexure sufficient for the distal end region 20 to advance via a guide catheter into the renal artery without substantially straightening out the guide catheter.

Angle α1 is defined by the angular deviation that the treatment device 12 must navigate to transition between the aorta (along which the force transmitting section 30 is aligned) and the targeted renal artery (along which the distal end region 20 is aligned) (this is also shown in FIG. 6B). This is the angle that the first flexure zone 32 must approximate to align the distal end region 20 of the elongated shaft 16 with the targeted renal artery, while the force transmitting section 30 of the elongated shaft 16 remains aligned with the native axis of the aorta (as FIG. 6B shows). The more severe the take-off angle between the renal artery and the aorta, the greater bend the first flexure zone 32 will need to make for the distal end region of the treatment device to access the renal artery and the smaller the angle $\alpha 1$.

When the catheter is outside the patient and the first flexure zone 32 is in a substantially straight, non-deflected configuration, angle $\alpha 1$ (as shown in FIG. 7B) is approximately 180°. Upon full deflection of the first flexure zone 32, the angle $\alpha 1$ is reduced to anywhere between about 30° and 180°. In a representative embodiment, upon full deflection angle $\alpha 1$ is about 30° to about 135°. In another representative embodiment, upon full deflection angle $\alpha 1$ is about 90°.

The first flexure zone 32 is sized and configured to possess mechanical properties that accommodate significant, abrupt flexure or bending at the access angle $\alpha 1$ near the junction of the aorta and the renal artery. Due to its size, configuration, and mechanical properties, the first flexure zone 32 must resolve these flexure or bending forces without fracture, collapse, distortion, or significant twisting. Such flexure or bending of the first flexure zone may occur at least in part within the distal region of a guide catheter without substantially straightening out the guide catheter. The resolution of these flexure or bending forces by the first flexure zone 32 makes it possible for the distal end region 20 of the elongated shaft 16 to gain entry along the intravascular path 14 into a targeted left or right renal artery.

The first flexure zone 32 is sized and configured in length L2 to be less than length L1 (see FIG. 7A). That is because the distance between the femoral access site and the junction of the aorta and renal artery (typically approximating about 40 cm to about 55 cm) is generally greater than the length of a renal artery between the aorta and the most distal treatment site along the length of the renal artery, which is typically less than about 7 cm. The preferred effective length L2 can be derived from textbooks of human anatomy, augmented with a caregiver's knowledge of the site generally or as derived from prior analysis of the particular morphology of the targeted site. For example, the length L2 generally may be less than about 15 cm, e.g., may be less than about 10 cm. In one representative embodiment, the length L2 may be about 9 cm.

Desirably, the length L2 is selected to make it possible to rest a portion of the first flexure zone 32 partially in the aorta at or near the length L1, as well as rest the remaining portion of the first flexure zone 32 partially within the renal artery (as FIG. 6B shows). In this way, the first flexure zone 32 defines a transitional bend that is supported and stable within the vasculature.

In the deflected configuration of FIG. 7B, the first flexure zone 32 comprises a radius of curvature $RoC_1$. In embodiments where the curvature of first flexure zone 32 does not vary or is consistent along the length L2, the length L2 and the deflection angle $\alpha 1$ may define the radius of curvature $RoC_1$. It should be understood that the curvature of first flexure zone 32, and thereby the radius of curvature $RoC_1$ of the first flexure zone, alternatively may vary along the length L2.

In such embodiments where the curvature does not vary, the length L2 may define a fraction $(180°-\alpha 1)/360°$ of the circumference $C_1$ of a circle with an equivalent radius of curvature $RoC_1$. Thus, the circumference of such an equivalent circle is:

$$C_1 = \frac{360°}{(180° - \alpha 1)} \times L2 = 2\pi \times RoC_1 \qquad (10)$$

Solving for the radius of curvature $RoC_1$:

$$RoC_1 = \frac{360° \times L2}{2\pi \times (180° - \alpha 1)} \qquad (11)$$

Thus, in a representative embodiment of the first flexure zone 32 where the curvature of the first flexure zone does not vary along the length L2, where the length L2 is about 9 cm, and where the angle $\alpha 1$ is about 30° to about 135°, the radius of curvature $RoC_1$ is about 3.5 cm to about 11.5 cm. In a representative embodiment of first flexure zone 32 where the curvature of the first flexure zone does not vary along the length L2, where the length L2 is about 9 cm, and where the angle $\alpha 1$ is about 90°, the radius of curvature $RoC_1$ is about 5.75 cm.

As will be apparent, Equation (11) may be rearranged such that the length L2 and the radius of curvature $RoC_1$ define the angle $\alpha 1$. Furthermore, Equation (11) may be rearranged such that the radius of curvature $RoC_1$ and the angle $\alpha 1$ define the length L2. Thus, in embodiments where the curvature of first flexure zone 34 does not vary along the length L2, any one of the length L2, angle $\alpha 1$ and radius of curvature $RoC_1$ may be specified by specifying the other two variables.

As will be described in greater detail later, and as shown in FIG. 6B, the length L2 of the first flexure zone 32 optionally does not extend the full length of the targeted length of the renal artery. That is because the distal end region 20 of the elongated shaft 16 optionally includes one or more additional flexure zones, distal to the first flexure zone 32 (toward the substance of the kidney), to accommodate other different functions important to the therapeutic objectives of the treatment device 12. As will be described later, the ability to transmit torque through the first flexure zone 32 makes it possible to rotate the thermal heating device to properly position the energy delivery element within the renal artery for treatment.

In terms of axial and torsional stiffness, the mechanical properties of first flexure zone 32 can, and desirably do, differ from the mechanical properties of the force transmitting section 30. This is because the first flexure zone 32 and the force transmitting section serve different functions while in use. Alternatively, the mechanical properties of first flexure zone 32 and force transmitting section 30 can be similar.

The force transmitting section 30 serves in use to transmit axial load and torque over a relatively long length (L1) within the vascular pathway. In contrast, the first flexure zone 32 needs to transmit axial load and torque over a lesser length L2 proximate to or within a respective renal artery. Importantly, the first flexure zone 32 must abruptly conform to an access angle $\alpha 1$ near the junction of the aorta and the respective renal artery, without fracture, collapse, significant twisting, or straightening a guide catheter imparting the access angle $\alpha 1$. This is a function that the force transmitting zone need not perform. Accordingly, the first flexure zone 32 is sized and configured to be less stiff and to possess greater flexibility than the force transmitting section 30.

Additionally, the first flexure zone 32 may allow energy delivery element(s) 24 to maintain stable contact with the interior wall of the renal artery as the respective kidney moves due to patient respiration. As a patient breathes the kidney may move, causing the renal artery to pivot about the ostium, where the renal artery joins the aorta. Stable contact between the energy delivery element(s) 24 and the inner wall of the renal artery is desired during energy delivery. Therefore, the energy delivery element(s) 24 must move, along with the renal artery, relative to the aorta. The mechanical properties of the first flexure zone 32 that accommodate significant, abrupt flexure or bending at the access angle α1 near the junction of the aorta and the renal artery also allow the sections of the catheter distal to the first flexure zone 32 to pivot about the ostium without significant impediment, allowing the energy delivery element to maintain stable contact force with the inner wall of the renal artery. In some embodiments, deflectable section 34 distal to first flexure zone 32 may become more stiff than the first flexure zone 32 when it is controllably deflected. The additional stiffness of deflectable section 34 helps maintain a stable contact force between the energy delivery element 24 and an inner wall of the renal artery and allows the catheter to move with the renal artery relative to the aorta with sufficient freedom due to the flexible deformation of the first flexure zone 32. The renal artery pivots about the juncture with the aorta such that movement of the renal artery increases with distance from the juncture with the aorta. The length of the distal end region 20 distal to the first flexure zone 32 along with the length of the first flexure zone 32 is configured such that an increasing portion of the first flexure zone 32 is positioned in the renal artery the more distal the treatment site to provide sufficient increased flexibility in the region of the juncture with the aorta to allow stable contact force between the energy delivery element 24 and the more distal treatment site of the inner wall of the renal artery, especially during increased motion at the more distal treatment site.

The desired magnitude of axial stiffness, rotational stiffness, and flexibility for the first flexure zone 32 can be obtained by selection of constituent material or materials to provide a desired elastic modulus (expressed, e.g., in terms of a Young's Modulus (E)) indicative of flexibility, as well as selecting the construct and configuration of the force transmitting section, e.g., in terms of its interior diameter, outer diameter, wall thickness, and structural features, including cross-sectional dimensions and geometry. Representative examples will be described in greater detail later.

Although it is desirable that the force transmitting section 30 and the first flexure zone 32 have stiffness and flexibility properties that are unique to their respective functions, it is possible that the force transmitting section 30 and the first flexure zone 32 comprise the same materials, size and geometric configuration such that the force transmitting section 30 and the first flexure zone 32 constitute the same section.

3. Deflectable Section

As shown in FIGS. 7A, 7B, and 7C, the distal end region 20 of the elongated shaft 16 also optionally may include, distal to the first flexure zone 32, a deflectable section 34. In some embodiments, the energy delivery element 24 may be supported by the deflectable section 34. It should be understood that the deflectable section can be used interchangeably with second flexure zone or intermediate flexure zone or deflectable tubular body.

The deflectable section 34 is sized, configured, and has the mechanical properties that accommodate additional flexure or bending, independent of the first flexure zone 32, at a preferred contact angle α2, without fracture, collapse, substantial distortion, or significant twisting. The deflectable section 34 should also accommodate flexure sufficient for the distal end region 20 to advance via a guide catheter into the renal artery without straightening out the guide catheter.

The preferred contact angle α2 is defined by the angle through which the energy delivery element 24 can be radially deflected within the renal artery to establish contact between the energy delivery element 24 and an inner wall of the respective renal artery (as FIG. 6B shows). The magnitude of the contact angle α2 and the length of the deflectable section L3 preferably are based on the native inside diameter of the respective renal artery where the energy delivery element 24 rests, which may vary between about 2 mm and about 10 mm, as well as the diameter of the energy delivery element 24. It is most common for the diameter of the renal artery to vary between about 2 mm and about 8 mm, with a mean diameter of about 6 mm.

The deflectable section 34 extends distally from the first flexure zone 32 for a length L3 into the targeted renal artery (see FIG. 6B). Desirably, the length L3 is selected, taking into account the length L2 of the first flexure zone 32 that extends into the renal artery, as well as the anatomy of the respective renal artery, to actively place the energy delivery element 24 (carried at the end of the distal end region 20) at or near the targeted treatment site (as FIG. 6B shows). The length L3 can be derived, taking the length L2 into account, from textbooks of human anatomy, together with a caregiver's knowledge of the site generally or as derived from prior analysis of the particular morphology of the targeted site.

As FIG. 7A shows, the deflectable section 34 is desirably sized and configured in length L3 to be less than length L2. This is because, in terms of length, the distance required for actively deflecting the energy delivery element 24 into contact with a wall of the renal artery is significantly less than the distance required for bending the elongated shaft 16 to gain access from the aorta into the renal artery. Thus, the length of the renal artery is occupied in large part by the deflectable section 34 and not as much by the first flexure zone 32.

In a representative embodiment, L2 is about 9 cm and L3 is about 5 mm to about 15 mm. In certain embodiments, particularly for treatments in relatively long blood vessels, L3 can be as long as about 20 mm. In another representative embodiment, and as described later in greater detail, L3 is about 12.5 mm.

When the catheter is outside the patient and the deflectable section 34 is in a substantially straight, non-deflected configuration, contact angle α2 (as shown in FIG. 7C) is approximately 180°. Upon full deflection of the deflectable section 34, the angle α2 is reduced to anywhere between about 45° and 180°. In a representative embodiment, upon full deflection, angle α2 is about 75° to about 135°. In another representative embodiment, upon full deflection, angle α2 is about 90°.

In the deflected configuration of FIG. 7C, the deflectable section 34 comprises a radius of curvature $RoC_2$. In embodiments where the curvature of deflectable section 34 does not vary or is consistent along the length L3, the length L3 and the contact angle α2 may define the radius of curvature $RoC_2$. It should be understood that the curvature of deflectable section 34, and thereby the radius of curvature $RoC_2$ of the deflectable section, alternatively may vary along the length L3.

In such embodiments where the curvature does not vary, the length L3 may define a fraction (180°−α2)/360° of the circumference $C_2$ of a circle with an equivalent radius of curvature $RoC_2$. Thus, the circumference of such an equivalent circle is:

$$C_2 = \frac{360°}{(180° - \alpha 2)} \times L3 = 2\pi \times RoC_2 \quad (12)$$

Solving for the radius of curvature $RoC_2$:

$$RoC_2 = \frac{360° \times L3}{2\pi \times (180° - \alpha 2)} \quad (13)$$

Thus, in a representative embodiment of the deflectable section 34 where the curvature of the deflectable section does not vary along the length L3, where the length L3 is about 5 mm to about 20 mm, and where the contact angle α2 is about 75° to about 135°, the radius of curvature $RoC_2$ is about 3 mm to about 25 mm. In a representative embodiment of deflectable section 34 where the curvature of the deflectable section does not vary along the length L3, where the length L3 is about 12.5 mm, for example less than or equal to about 12.5 mm, and where the angle α2 is about 75° to about 135°, the radius of curvature $RoC_2$ is about 7 mm to about 16 mm, for example less than or equal to about 15 mm. In a representative embodiment of deflectable section 34 where the curvature of the deflectable section does not vary along the length L3, where the length L3 is about 12.5 mm, and where the angle α2 is about 90°, the radius of curvature $RoC_2$ is about 8 mm.

As will be apparent, Equation (13) may be rearranged such that the length L3 and the radius of curvature $RoC_2$ define the contact angle α2. Furthermore, Equation (13) may be rearranged such that the radius of curvature $RoC_2$ and the angle α2 define the length L3. Thus, in embodiments where the curvature of deflectable section 34 does not vary along the length L3, any one of the length L3, angle α2 and radius of curvature $RoC_2$ may be specified by specifying the other two variables.

In the deflected configuration of FIG. 7C, the deflectable section 34 locates the energy delivery element 24 at a dimension Y from a longitudinal axis A of the deflectable section 34 just distal of the first flexure zone 32. The dimension Y can vary from about 2 mm to about 20 mm. In some configurations, and given the dimension of most renal arteries, the dimension Y can be from about 5 mm to about 15 mm. Since the average diameter of most renal arteries is generally less than 10 mm as described below, it may be desirable for dimension Y to be less than or equal to 10 mm. For example the Y dimension can be 6 mm or 8 mm or anywhere between and including 6 mm to 10 mm.

By way of example, the average diameter of a human renal artery is from about 2 mm to about 8 mm, but may range from about 2 mm to about 10 mm. Accordingly, if the distal end of the first flexure zone 32 were positioned adjacent to a wall of an artery having an 8 mm diameter, the deflectable section 34 would be capable of deflection sufficient for the energy delivery element 24 to contact the opposite wall of the artery. In other embodiments, however, the dimension Y may have a different value and may be oversized to facilitate contact in a straight or curved vessel. The deflectable section 34 is also configured to locate the energy delivery element 24 at a dimension X from a distal end of the first flexure zone 32. The dimension X can vary, e.g., based on the dimension Y and the length L3.

As FIG. 7C shows, having first flexure zone and deflectable section 32 and 34, the distal end region 20 of the elongated shaft 16 can, in use, be placed into a complex, multi-bend structure 36. The complex, multi-bend structure 36 comprises one deflection region at the access angle α1 over a length L2 (the first flexure zone 32) and a second deflection region at the contact angle α2 over a length L3 (the deflectable section 34). In the complex, multi-bend, both L2 and L3 and angle α1 and angle α2 can differ. This is because the angle α1 and length L2 are specially sized and configured to gain access from an aorta into a respective renal artery through a femoral artery access point, and the angle α2 and length L3 are specially sized and configured to align an energy delivery element 24 with an interior wall inside the renal artery.

In the illustrated embodiment (see, e.g., FIG. 7C), the deflectable section 34 is sized and configured to allow a caregiver to remotely deflect the deflectable section 34 within the renal artery, to radially position the energy delivery element 24 into contact with an inner wall of the renal artery.

Figures 15A, 15B, 15C, 15D:
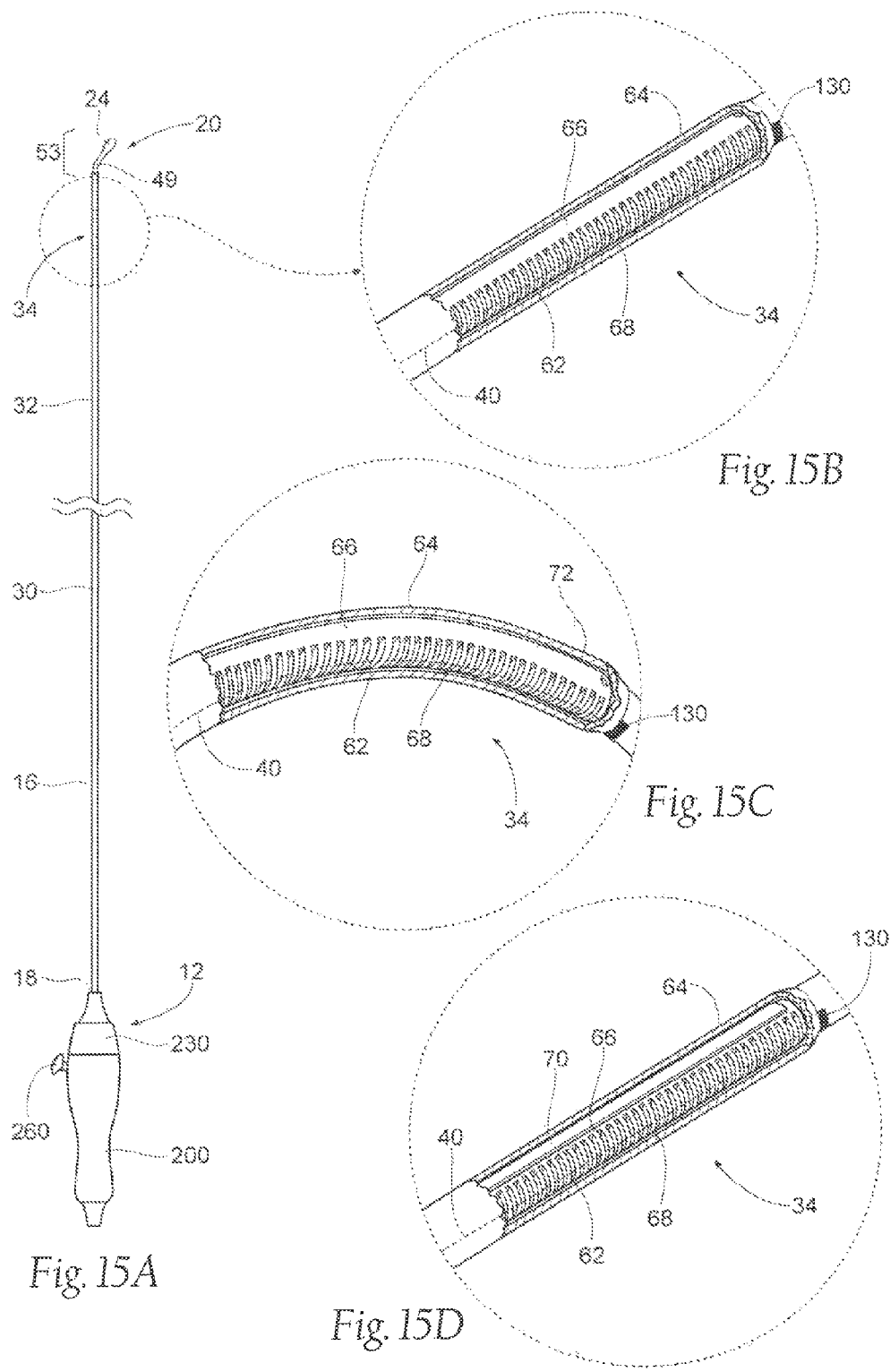
FIGS. 15A to 15D show a representative embodiment of the deflectable section of the elongated shaft of the treatment device shown in FIG. 5.

In the illustrated embodiment, a control mechanism is coupled to the deflectable section 34. The control mechanism includes a control wire 40 attached to the distal end of the deflectable section 34 (a representative embodiment is shown in FIGS. 15B and 15C and will be described in greater detail later). It should be understood that the term control wire can be used interchangeably with flexure control element. The control wire 40 is passed proximally through the elongated shaft 16 and coupled to an actuator 260 on the handle assembly 200. Operation of the actuator 260 (e.g., by the caregiver pulling proximally on or pushing forward the actuator 260) pulls the control wire 40 back to apply a compressive and bending force to the deflectable section 34 (as FIGS. 7C and 15C show) resulting in bending. The compressive force in combination with the optional directionally biased stiffness (described further below) of the deflectable section 34 deflects the deflectable section 34 and, thereby, radially moves the energy delivery element 24 toward an interior wall of the renal artery (as FIG. 6B shows).

Desirably, as will be described in greater detail later, the distal end region 20 of the elongated shaft 16 can be sized and configured to vary the stiffness of the deflectable section 34 about its circumference. The variable circumferential stiffness imparts preferential and directional bending to the deflectable section 34 (i.e., directionally biased stiffness). In response to operation of the actuator 260, the deflectable section 34 may be configured to bend in a single preferential direction. Representative embodiments exemplifying this feature will be described in greater detail later. Additional representative embodiments depicting multidirectional bending will also be described later in greater detail.

The compressive and bending force and resulting directional bending from the deflection of the deflectable section 34 has the consequence of altering the axial stiffness of the deflectable section. The actuation of the control wire 40 serves to increase the axial stiffness of the deflectable section. As will be described later, the axial stiffness of the deflected deflectable section in combination with other flexible aspects of the distal end region of the catheter treatment device allows for favorable performance in a renal artery neuromodulation treatment.

In terms of axial and torsional stiffnesses, the mechanical properties of deflectable section 34 can, and desirably do, differ from the mechanical properties of the first flexure zone 32. This is because the first flexure zone 32 and the deflectable section 34 serve different functions while in use.

The first flexure zone 32 transmits axial load and torque over a longer length (L2) than the deflectable section 34 (L3). Importantly, the deflectable section 34 is also sized and configured to be deflected remotely within the renal artery by the caregiver. In this arrangement, less resistance to deflection is desirable. This is a function that the first flexure zone 32 need not perform. Accordingly, the deflectable section 34 is desirably sized and configured to be less stiff (when the control wire 40 is not actuated) and, importantly, to possess greater flexibility than the first flexure zone 32 in at least one plane of motion.

Still, because the deflectable section 34, being distal to the first flexure zone 32, precedes the first flexure zone 32 through the access angle access angle α1, the deflectable section 34 also includes mechanical properties that accommodate its flexure or bending at the preferred access angle α1, without fracture, collapse, substantial distortion, or significant twisting of the elongated shaft 16.

The desired magnitude of axial stiffness, rotational stiffness, and flexibility for the deflectable section 34 can be obtained by selection of constituent material or materials to provide a desired elastic modulus (expressed, e.g., in terms of a Young's Modulus (E)) indicative of flexibility, as well as by selecting the construct and configuration of the deflectable section 34, e.g., in terms of its interior diameter, outer diameter, wall thickness, and structural features, including cross-sectional dimensions and geometry. Representative examples will be described in greater detail later. Axial stiffness, torsional stiffness, and flexibility are properties that can be measured and characterized in conventional ways.

As before described, both the first flexure zone and deflectable section 32 and 34 desirably include the mechanical properties of axial stiffness sufficient to transmit to the energy delivery element 24 an axial locating force. By pulling back on the handle assembly 200, axial forces are transmitted by the force transmitting section 30 and the first flexure zone and deflectable section 32 and 34 to retract the energy delivery element 24 in a proximal direction (away from the kidney) within the renal artery. Likewise, by pushing forward on the handle assembly 200, axial forces are transmitted by the force transmitting section 30 and the first flexure zone and deflectable section 32 and 34 to advance the energy delivery element 24 in a distal direction (toward the kidney) within the renal artery. Thus, proximal retraction of the distal end region 20 and energy delivery element 24 within the renal artery can be accomplished by the caregiver by manipulating the handle assembly 200 or shaft from outside the intravascular path 14.

As before described, both the first flexure zone and deflectable section 32 and 34 also desirably include torsional strength properties that will allow the transmission of sufficient rotational torque to rotate the distal end region 20 of the treatment device 12 such that the energy delivery element 24 is alongside the circumference of the blood vessel wall when the deflectable section 34 is deflected. By pulling or pushing on the actuator to deflect the energy delivery element 24 such that it achieves vessel wall contact, and then rotating the force transmitting section 30 and, with it, the first flexure zone and deflectable section 32 and 34, the energy delivery element 24 can be rotated in a circumferential path within the renal artery. As described later, this rotating feature enables the clinical operator to maintain vessel wall contact as the energy delivery element 24 is being relocated to another treatment site. By maintaining wall contact in between treatments, the clinical operator is able to achieve wall contact in subsequent treatments with higher certainty in orientations with poor visualization.

4. Force Redirecting Element

As shown in FIG. 7A the distal end region 20 comprises a distal assembly 53 which comprises a force redirecting element 49, a force dampening section 44, and an energy delivery element 24. In some embodiments the force redirecting element 49 is connected to the elongated shaft 16 distal to the deflectable section 34; the force redirecting element 49 is further joined to a force dampening section 44 which is joined to an energy delivery element 24 positioned at the distal most point of the elongated shaft. In some embodiments the force redirecting element 49 is part of the force dampening section 44. In other embodiments the force redirecting element 49 is part of the deflectable section 34. It should be understood that the force redirecting element can be used interchangeably with pre-shaped geometry.

In some embodiments it may be desirable to establish proximity to and alignment between the energy delivery element 24 and specific target regions of tissue along an interior wall of the renal artery. As previously discussed, renal arteries may vary in length, diameter and tortuosity. Establishing proximity to and alignment between the energy delivery element 24 and specific target regions may require advancing the distal end region 20 through a renal artery with a high degree of tortuosity. As will be discussed in greater detail later, in some embodiments, the distal end region comprises a distal assembly 53 comprising a force redirecting element 49 specially sized and configured to facilitate advancement through renal arteries of various tortuosity and dimension while reducing the risk of exerting traumatic forces to the interior wall of the renal artery. In some embodiments a force redirecting element 49 is configured to facilitate contact between the energy delivery element 24 and target regions of a wall of the renal artery. In some embodiments a force redirecting element 49 is configured to facilitate the establishment and maintenance of stable contact force between the energy delivery element 24 and a wall of the renal artery prior to and during delivery of energy.

Figure 8A:
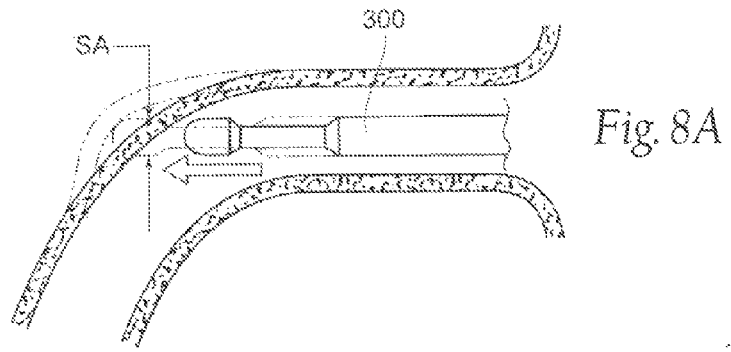
FIG. 8A shows an anatomic view of the advancement of a treatment device without the features of the present invention within a renal artery.
Figure 8B:
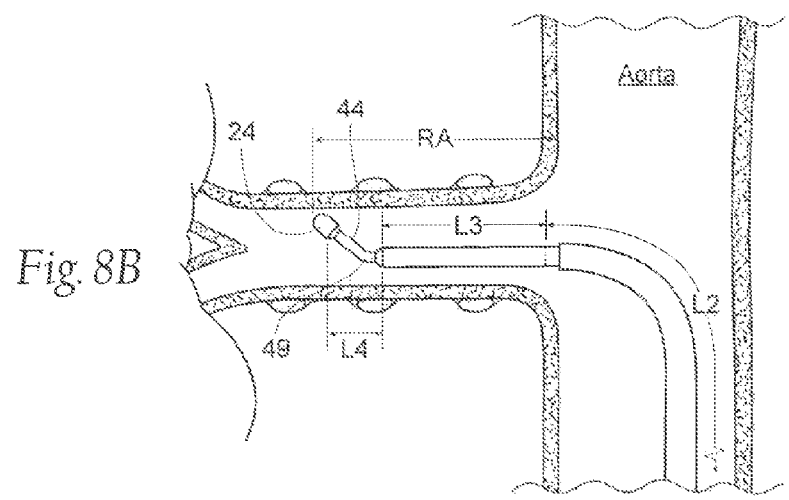
FIGS. 8B to 8D show an anatomic view of the placement of the treatment device shown in FIG. 5 within the dimensions of the renal artery.
Figure 8C:
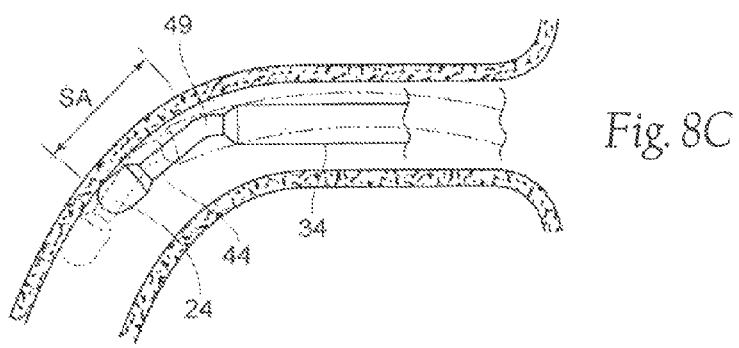
Figure 8D:
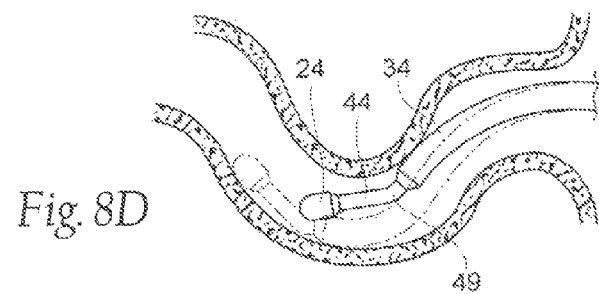

Advancement of a catheter through a renal artery can involve navigating the catheter through tight bends as shown in FIG. 8D. Considering the fragility of the renal artery wall, especially in patients with vascular disease (e.g., arthrosclerosis), the risk of trauma during catheter advancement is a concern. The force redirecting element 49, in combination with the deflectable section 34, force dampening section 44 and energy delivery element 24, is specially shaped and configured to reduce the risk of traumatic contact force between the catheter and renal artery wall as the catheter is advanced. Trauma can be caused by over distending, perforating and/or puncturing the renal artery wall and/or scraping the wall and disrupting the epithelial tissue. A force redirecting element 49 can reduce the risk of trauma by means of i) displacing an axial load on a catheter column to an eccentric load and/or a side load to facilitate buckling of the catheter shaft, ii) changing the direction of a force applied to a renal artery wall, iii) reducing pressure exerted to the renal artery wall by increasing surface area, and/or iv) facilitating navigation around a sharp bend.

For purposes of discussing the force interactions between the catheter and artery wall a simplified example with an effectively stiff and straight catheter 300 (as shown in FIG. 8A) follows. As discussed in more detail later, variables such as catheter flexibility, dimensions, and geometry as represented by the present invention modify the force interactions. Every force has both a magnitude and direction. The magnitude of the force applied by an effectively stiff and straight catheter on to the artery wall is essentially equal to the force applied by the caregiver advancing the catheter into the body. In this example the essentially straight and stiff catheter is advanced into a renal artery by pushing the proximal end of the catheter, thus the catheter's advancing trajectory is translation along the catheter's axis. Therefore, the direction of the force applied by the catheter on the artery wall is forward along the catheter's axis. In this simplified example, the artery wall is represented by an elastic wall that has a maximum distension and wall strength. The force exerted by the artery wall includes a normal force, the component perpendicular to the surface, which is characterized by the artery wall's ability to withstand distension and puncture (a function of elasticity and strength); and the component parallel to the artery wall surface, which is characterized by the friction between the artery wall and catheter surface.

A straight catheter shaft is similar to a column which can withstand a significant load along its axis before deforming. A load applied to the side of a column will cause it to bend at a lower force than an axial load. A load applied parallel to the column but at a distance from its axis, an eccentric load, will cause the column to buckle with a smaller load than an axial load. The more eccentric the load the smaller the force required to buckle the column. A specially configured force redirecting element 49 distances the distal tip of the catheter from the axis such that as the distal tip is advanced into a renal artery wall the load applied to all parts of the distal end region 20 is eccentric. In particular, the load applied to the force dampening section 44 is at an angle to the axis, thereby promoting deformation or buckling of the force dampening section 44; the load applied to the deflectable section is eccentric causing it to buckle as shown in FIGS. 8C and 8D. Thus, the distal end region 20 is configured to deform under a load that is less than a load that could apply a pressure to an artery wall causing excessive trauma, thereby reducing the risk of trauma to the renal artery wall. Examples of distal end regions 20 comprising different embodiments of force redirecting element 49 are shown in FIGS. 10A to 10E.

FIGS. 9A to 9D provide a conceptual illustration of the force vectors that may exist as a catheter is advanced within the artery. For example, $F_C$ corresponds to a force vector applied by a catheter, which is broken out into a component vector parallel to the artery wall, $F_{CP}$, and perpendicular or normal to the artery wall, $F_{CN}$. Likewise, $F_A$ corresponds to a force vector applied by the artery wall, which is broken out into a component vector parallel to the artery wall, $F_{AP}$, and perpendicular to the artery wall, $F_{AN}$. $F_R$ corresponds to a resultant force vector.

As illustrated in FIGS. 9A to 9D, when the catheter's trajectory is parallel to the artery wall the catheter may glide through the artery occasionally glancing off the wall contacting at the tip or along the side of the catheter's shaft. The force applied to the artery wall would be parallel to the wall and there would be minimal normal component $F_{CN}$ with small parallel component $F_{CP}$. As the angle of the catheter's trajectory with the wall increases to a small acute angle the normal and frictional reactive components increase. If the normal and frictional components are not exceeded the vessel wall will stay intact and the catheter will slide against the wall. As the angle of the catheter's trajectory with the wall increases to a larger acute angle, the normal component increases, increasing the risk of trauma by scraping or puncture. The following scenarios are illustrated with force vectors in FIGS. 9A to 9D.

Figure 9A:
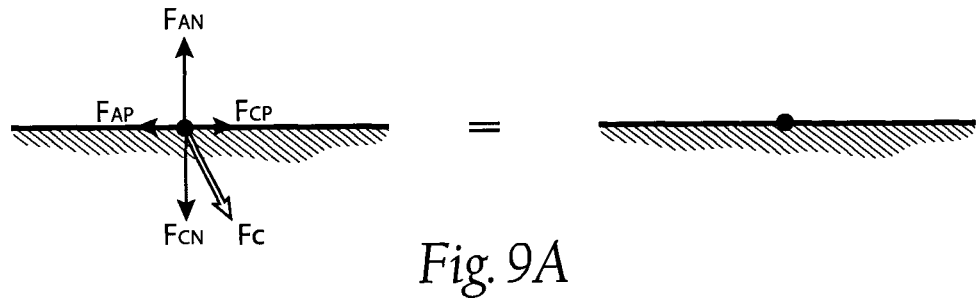
FIGS. 9A to 9D show force vectors of trajectories of a straight catheter (not of the present invention) advancing into a soft wall and the resultant forces.

If $F_{CP}<=F_{AP}$ and $F_{CN}<=F_{AN}$, then $F_R=0$ and the catheter will not move nor exert trauma to the artery wall. (FIG. 9A)

Figure 9B:
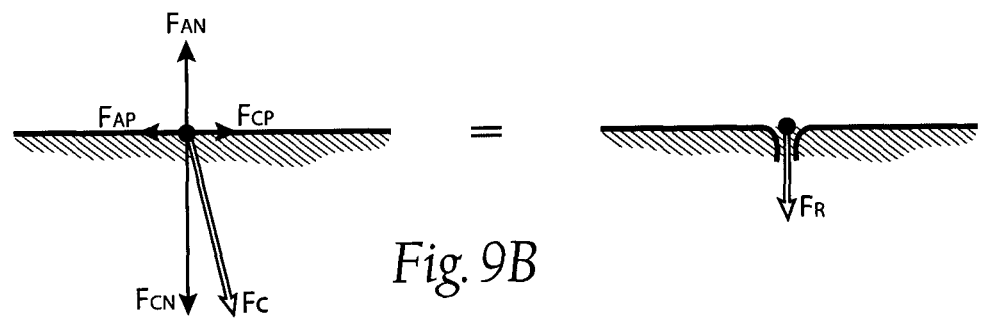

If $F_{CP}<=F_{AP}$ and $F_{CN}>F_{AN}$, then $F_R$ is of a magnitude and direction that could cause the catheter to distend or perforate the artery wall. (FIG. 9B)

Figure 9C:
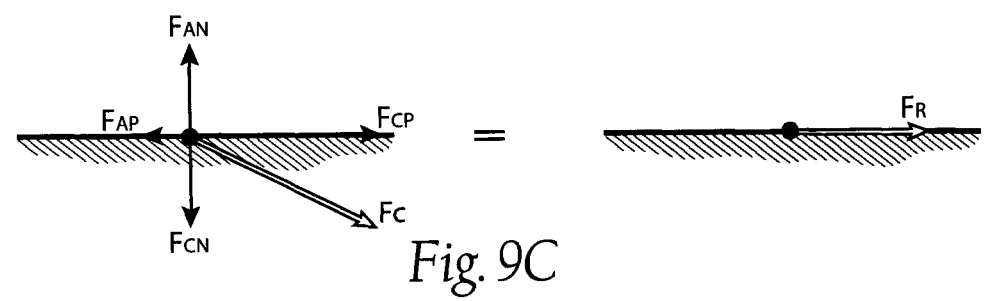

If $F_{CP}>F_{AP}$ and $F_{CN}<=F_{AN}$, then $F_R$ is of a magnitude and direction that could cause the catheter to slide forward with no trauma. (FIG. 9C)

Figure 9D:
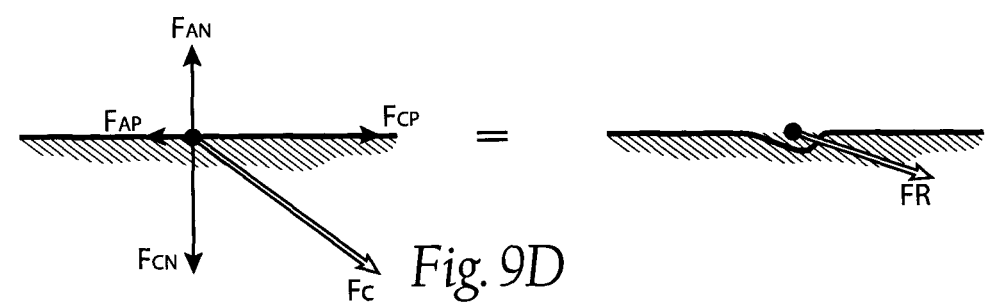

If $F_{CP}>F_{AP}$ and $F_{CN}>F_{AN}$, then $F_R$ is of a magnitude and direction that could cause the catheter to slide forward and distend the artery wall and possibly cause scraping trauma to the epithelial layer. (FIG. 9D)

If a catheter's trajectory is essentially at a perpendicular angle with the wall of the artery there is very little parallel component and mostly normal component. Any force applied to advance the catheter will be directed straight into the artery wall creating a very high risk of puncture trauma. Angles that are close to perpendicular will have a large normal component and some parallel component which can cause scraping trauma. In some embodiments as described later, a specially configured force redirecting element 49 in combination with force dampening section 44, deflectable section and first flexure zone 32 can mitigate this risk, first by promoting a portion of the catheter shaft to buckle under an eccentric load, then by changing a direction of the exerted force to redistribute the normal force component to more parallel force component as shown in FIGS. 8C and 8D.

Furthermore, the pressure applied by the catheter to the artery wall is the force divided by the area of contact. If only the tip of the catheter contacts the artery wall, the pressure is equal to the force divided by the contacting surface area of the tip. If the catheter contacts the artery wall over a large contacting surface area SA such as along the side of an energy delivery element 24 and force dampening section 44, as shown in FIG. 8C, then the pressure is greatly reduced as the force is divided by a much larger area. For example, the pressure exerted by a catheter with a 0.049" diameter tip is about equal to the force applied to an area of a 0.049" circle which is about 530 times the force. With a specially configured force redirecting element 49 a catheter can contact the artery wall over an area of about 0.0076 inches squared applying a pressure of about 131 times the force. This feature provides a force reduction of approximately 75% or more.

A specially configured force redirecting element 49 can also facilitate navigation around a tight bend in a renal artery. As described in more detail later, a force redirecting element 49 has dimensions and geometry that allows the distal end of the catheter 57 to advance around a bend in a renal artery ahead of the catheter's axis and facilitates flexure of the force dampening section.

In some embodiments a force redirecting element is specially configured to further facilitate placement of an energy delivery element 24 in alignment with an inner wall of a renal artery. A force redirecting element 49 can facilitate placement of an energy delivery element 24 in alignment with an inner wall of a renal artery by means of i) providing multiple direction deflection of a deflectable section 34 about the axis with a force redirecting element 49 located on the deflectable section 34, or ii) deflecting the distal end region in multiple directions toward the renal artery wall when a force redirecting element 49 is specially configured to be used with a delivery sheath.

Figure 11A:
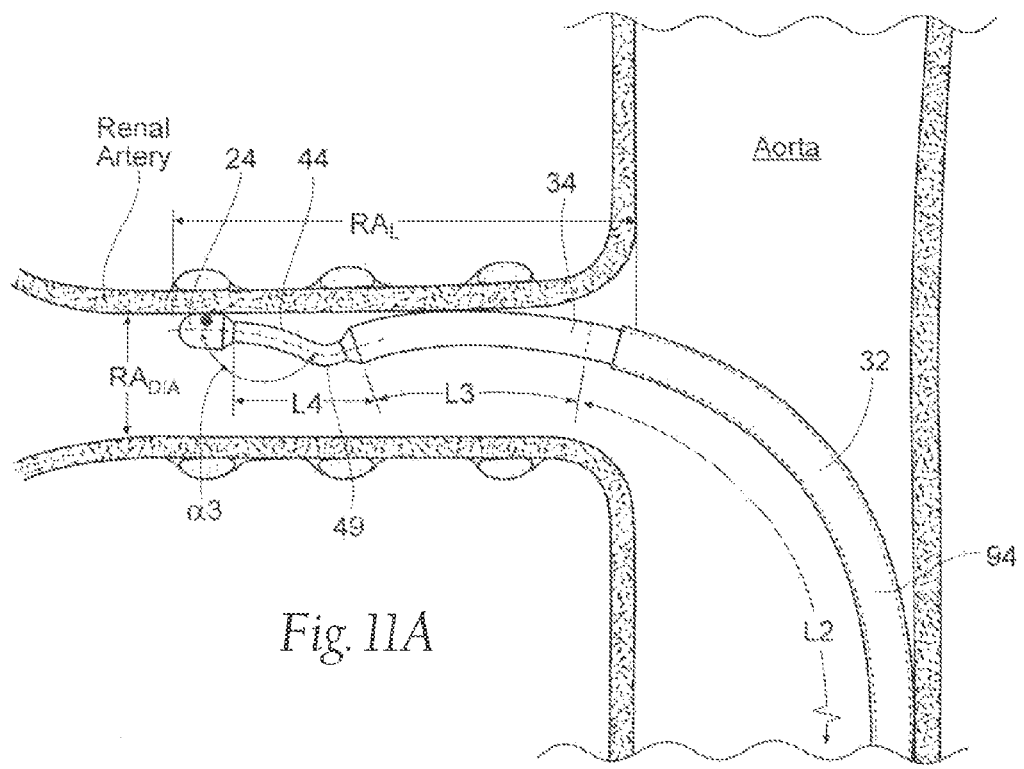
FIGS. 11A to 11B show the placement of an energy delivery element, which is carried at the distal end of the elongated shaft of the treatment device shown in FIG. 5, into contact with tissue along a renal artery.
Figure 12A:
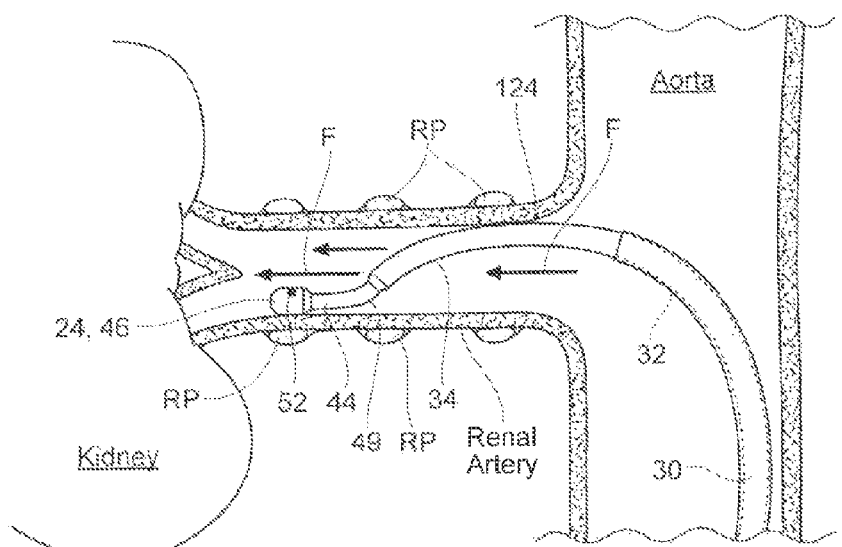
FIGS. 12A and 12B show placement of the energy delivery element shown in FIGS. 11A to 11B into contact with tissue along a renal artery and delivery of thermal treatment to the renal plexus.

In some embodiments a deflectable section 34 is configured for single-direction deflection and the placement of an energy delivery element 24 in contact with an inner wall of a renal artery in various radial directions about the catheter axis is accomplished by combinations of deflecting the deflectable section 34 and rotating the catheter as will be discussed in more detail later. In some embodiments a deflectable section 34 is configured for multiple direction deflection which can facilitate the placement of an energy delivery element 24 in contact with an inner wall of a renal artery with less need for rotating the catheter. In some embodiments with single direction deflection, a force redirecting element 49 can further facilitate placement of an energy delivery element 24 by providing off axis displacement of the energy delivery element 24 in additional radial directions about the catheter axis. For example, in some embodiments a force redirecting element 49 distances an energy delivery element 24 from the catheter axis in an opposite direction than the biased deflection of a deflectable section 34. As shown in FIG. 11A a force redirecting element 49 displaces an energy delivery element 24 above the undeflected deflectable section 34 and the energy delivery element 24 exerts a stable contact force on, and is aligned with, the inner wall of a renal artery through flexure of a force dampening section 44. As shown in FIG. 12A without rotating the catheter, the deflectable section 34 is deflected to bring the energy delivery element 24 in alignment with, and exerting a stable contact force on, the inner wall of the renal artery.

In yet another embodiment shown in FIGS. 18A through 18G a force redirecting element 49 is located in a deflectable section 34 and distances the energy delivery element 24 a predetermined distance from the axis of the catheter in the opposite direction from the biased deflection of the deflectable section 34 when the deflectable section 34 is not deflected. Partial deflection of the deflectable section 34 straightens the deflectable section 34 and full deflection of the deflectable section 34 deflects it in the biased deflection direction. This embodiment facilitates placement of an energy delivery element 24 in multiple directions about the catheter axis without multiple control wires and with less need for rotation.

In the embodiments shown in FIGS. 22A through 22F a distal assembly 53 comprises two force redirecting elements 49' and 49" longitudinally spaced apart. This embodiment utilizes force redirecting elements 49' and 49" to facilitate placement of an energy delivery element 24 in contact with an inner wall of a renal artery at various locations using multiple direction deflection without the requirement of a deflectable section 34. This embodiment is employed with a delivery sheath 95. When the distal end region 20 is retracted within the delivery sheath 95 the force redirecting elements 49' and 49" are flexibly conformed to the delivery sheath 95. When the delivery sheath is pulled back to expose the first force redirecting element 49' the force dampening section 44 is deflected in the direction of angle $\alpha 8$. When the delivery sheath 95 is further pulled back to expose a second force redirecting element 49" the force dampening section 44 is deflected in a new direction that is a cumulative effect of both angles $\alpha 8$ and $\alpha 9$. In this embodiment the distal assembly 53 is configured so that the energy delivery element 24 is sufficiently distanced from the axis of the catheter to be placed in contact with renal artery wall with stable contact force.

Figure 22A:
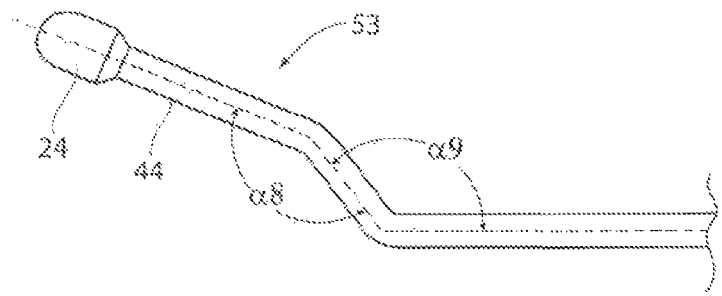
FIGS. 22A to 22G show additional alternative representative embodiments of an elongated shaft for a treatment device like that shown in FIG. 5, showing examples of the different structural, mechanical and functional regions that the elongated shaft can incorporate.
Figure 22B:
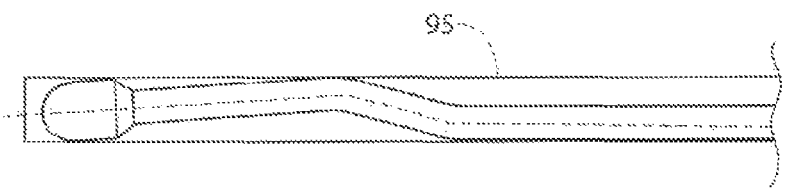
Figure 22C:
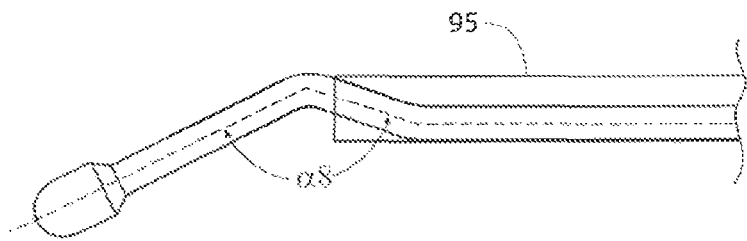
Figure 22D:
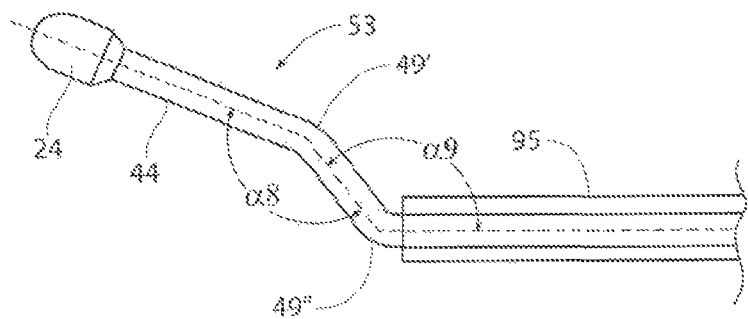
Figure 22E:
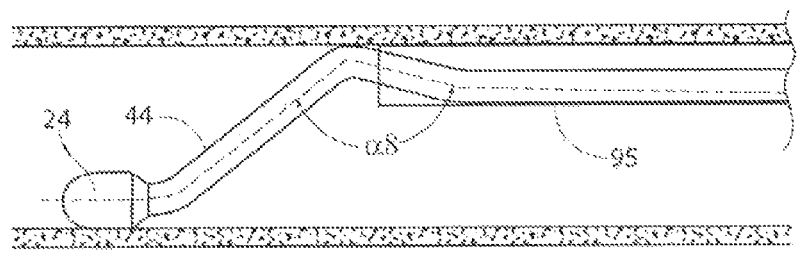
Figure 22F:
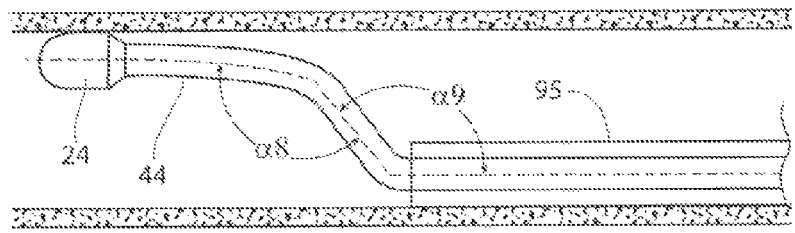
Figure 22G:
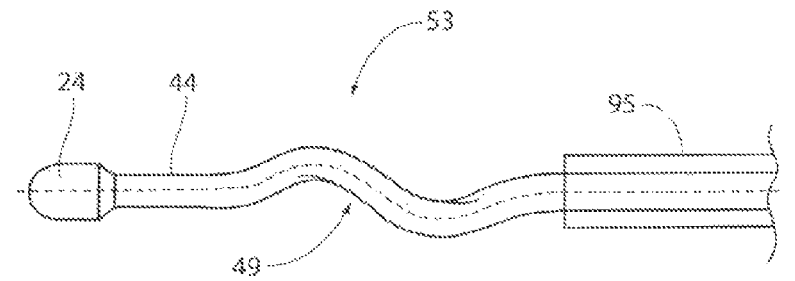

In a similar embodiment shown in FIG. 22G a force redirecting element 49 comprises a helical bend such that as a delivery sheath 95 is pulled back gradually exposing the force redirecting element 49 the force dampening section 44 is deflected in a rotating radial direction about the axis placing an energy delivery element 24 at different locations circumferentially spaced around the inner wall of the renal artery.

Figure 23A:
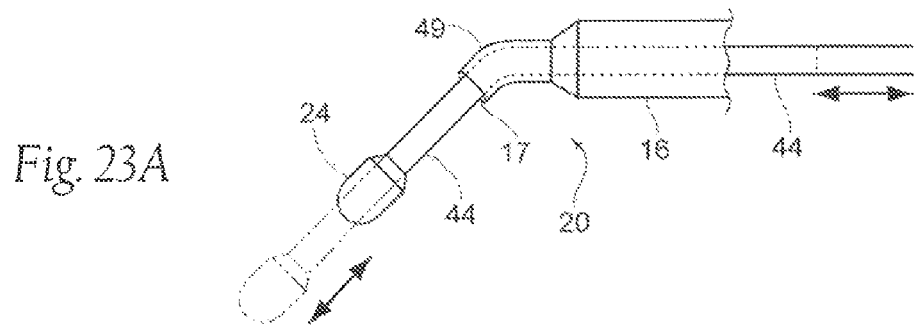
FIGS. 23A to 23D show additional alternative representative embodiments of an elongated shaft for a treatment device like that shown in FIG. 5, showing examples of the different structural, mechanical and functional regions that the elongated shaft can incorporate.
Figure 23B:
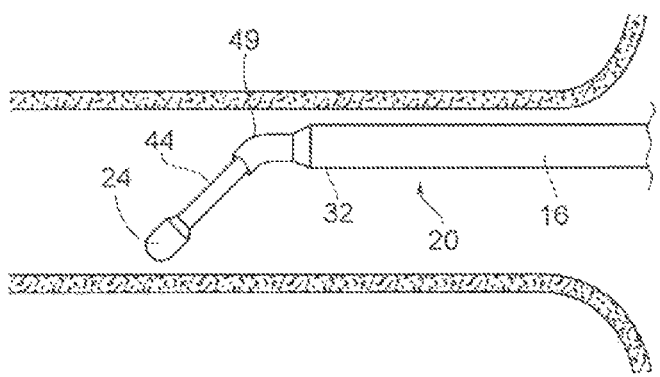
Figure 23C:
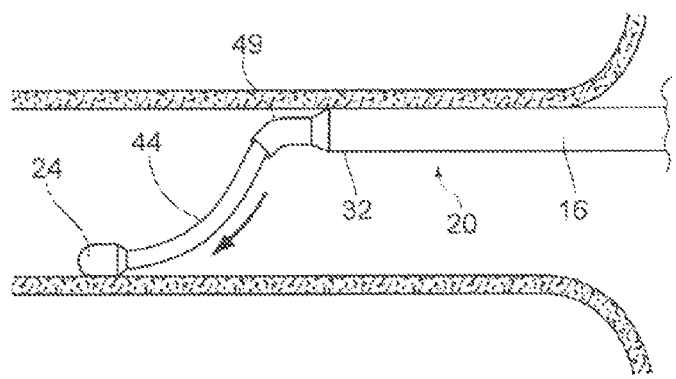
Figure 23D:
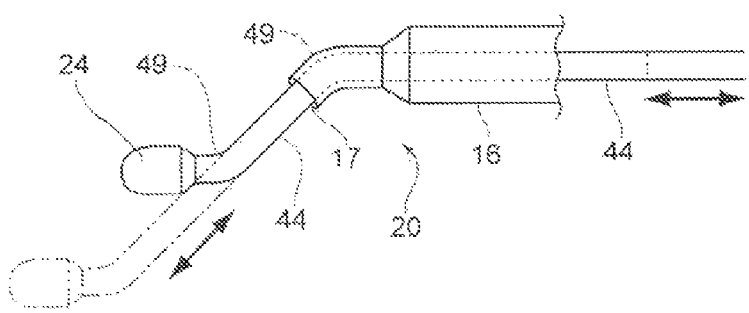

As shown in FIGS. 23A to 23D another embodiment comprises an energy delivery element 24 mounted distally to a force dampening section 44 made of a long flexible element, such as a wire or tube, which is slidably engaged in a lumen 17 of an elongated tubular body 16 and a force redirecting element 49. The force redirecting element 49 directs the force dampening section 44 off-axis from the elongated tubular body 16 so that the energy delivery element 24 is distanced from the axis of the elongated tubular body and the benefits of catheter navigation with reduced risk of trauma, as described earlier, are realized. Once distal end region 20 is navigated to a desired location in a renal artery, the force dampening section 44 is telescopically advanced through the lumen 17 by advancing the proximal end of the force dampening section 44 such that the energy delivery element 24 is placed at a greater distance from the axis of the elongated tubular body 16 until the energy delivery element 24 is placed in contact with an inner wall of a renal artery. In FIG. 23D the force dampening section 44 further comprises a distal force redirecting element 49' that distances the distal end of the energy delivery element 24 from the axis of the force dampening section 44 to redirect any force exerted to the energy delivery element 24 away from an axial load on the force dampening section 44 to promote buckling of the force dampening section 44 and reduce the risk of trauma that could be caused by telescopically advancing the force dampening section 44 and to facilitate alignment of the energy delivery element 24 in contact with the inner wall of the renal artery. Placement and stable contact force of the energy delivery element 24 is facilitated by the force redirecting element 49, which redirects the force dampening section 44 away from the axis of the elongated tubular structure.

5. Force Dampening Section

As FIGS. 7A, 7B, 7C, and 7D show, the distal end region 20 of the elongated shaft 16 also optionally may include, distal to the optional deflectable section 34, and distal to a force redirecting element 49, a force dampening section 44. In this arrangement, the length L3 of the deflectable section 34 may be shortened by a length L4, which comprises the length of the force dampening section 44. In this arrangement, the energy delivery element 24 is carried at the end of the force dampening section 44. It should be understood that the term force dampening section can be used interchangeably with third flexure zone or distal flexure zone or passively flexible structure.

As FIG. 7D shows, the force dampening section 44 is sized, configured, and has the mechanical properties that accommodate additional flexure or bending, independent of the first flexure zone 32 and the deflectable section 34, at a preferred treatment angle $\alpha 3$. The force dampening section 44 should also accommodate flexure sufficient for the distal end region 20 to advance via a guide catheter into the renal artery without straightening out the guide catheter or causing injury to the blood vessel. The treatment angle $\alpha 3$ provides for significant flexure about the axis of the distal end region 20 (a representative embodiment is shown in FIG. 16B). Not under the direct control of the physician, flexure at the force dampening section occurs in response to contact between the energy delivery element 24 and wall tissue occasioned by the radial deflection of the energy delivery element 24 at the deflectable section 34 (see FIG. 6B). Passive deflection of the force dampening section provides the clinical operator with visual feedback via fluoroscopy or other angiographic guidance of vessel wall contact (as shown in FIGS. 27A to 27E). Additionally, the force dampening section desirably orients the region of tissue contact along a side of the energy delivery element 24, thereby increasing the area of contact. The force dampening section 44 also biases the energy delivery element 24 against tissue, thereby stabilizing the energy delivery element 24.

The function of the force dampening section 44 provides additional benefits to the therapy. As actuation of the control wire 40 deflects the deflectable section 34, pressing the energy delivery element 24 against an inner wall of an artery the force dampening section effectively dampens the contact force between the energy delivery element 24 and the vessel wall. This effect is particularly valuable in a renal artery treatment due to movement of the renal artery caused by respiration and/or pulsatile flow. While the flexibility of the first flexure zone allows the distal end region of the treatment catheter to follow movement of the renal artery during respiration, the increased axial stiffness of the deflected deflectable section provides helpful integrity to the distal end region to maintain contact between the energy delivery element and vessel wall. The force dampening section helps soften or cushion the contact force so that atraumatic contact can be achieved and maintained, particularly during movement of the renal artery. By dampening this contact force, the force dampening section minimizes the chance of mechanical injury to the vessel wall and avoids excessive contact between the energy delivery element and vessel wall (see discussion of active surface area).

As FIG. 7A shows, the force dampening section 44 is desirably sized and configured in length L4 to be less than length L3. This is because, in terms of length, the distance required for orienting and stabilizing the energy delivery element 24 in contact with a wall of the renal artery is significantly less than the distance required for radially deflecting the energy delivery element 24 within the renal artery. In some embodiments, length L4 can be as long as about 1 cm. In other embodiments, the length L4 is from about 2 mm to about 5 mm. In one representative embodiment, the length L4 is about 5 mm. In another representative embodiment, the length L4 is about 2 mm. In another representative embodiment wherein the deflectable section 34 is comprised of a hinge joint, the length L4 is about 16 mm which in this embodiment can be greater than the length L3 of the deflectable section 34.

When the catheter is outside the patient and the force dampening section 44 is in a substantially straight, non-deflected configuration, treatment angle $\alpha 3$ (as shown in FIG. 7D) is approximately 180°. Upon full deflection of the force dampening section 44, the angle $\alpha 3$ is reduced to anywhere between about 45° and 180°. In a representative embodiment, upon full deflection, angle $\alpha 3$ is about 75° to about 135°. In another representative embodiment, upon full deflection, angle $\alpha 3$ is about 90°.

In the passively deflected configuration of FIG. 7D, the force dampening section 44 comprises a radius of curvature $RoC_3$. In embodiments where the curvature of force dampening section 44 does not vary or is consistent along the length L4, the length L4 and the contact angle $\alpha 3$ may define the radius of curvature $RoC_3$. It should be understood that the curvature of force dampening section 44, and thereby the radius of curvature $RoC_3$ of the force dampening section, alternatively may vary along the length L4.

In such embodiments where the curvature does not vary, the length L4 may define a fraction $(180°-\alpha 3)/360°$ of the circumference $C_3$ of a circle with an equivalent radius of curvature $RoC_3$. Thus, the circumference of such an equivalent circle is:

$$C_3 = \frac{360°}{(180° - \alpha 3)} \times L4 = 2\pi \times RoC_3 \quad (14)$$

Solving for the radius of curvature $RoC_2$:

$$RoC_3 = \frac{360° \times L4}{2\pi \times (180° - \alpha 3)} \quad (15)$$

Thus, in a representative embodiment of the force dampening section 44 where the curvature of the force dampening section does not vary along the length L4, where the length L4 is about 2 mm to about 5 mm, and where the contact angle $\alpha 3$ is about 75° to about 135°, the radius of curvature $RoC_3$ is about 1 mm to about 6 mm.

As will be apparent, Equation (15) may be rearranged such that the length L4 and the radius of curvature $RoC_3$ define the contact angle $\alpha 3$. Furthermore, Equation (15) may be rearranged such that the radius of curvature $RoC_3$ and the angle $\alpha 3$ define the length L4. Thus, in embodiments where the curvature of force dampening section 44 does not vary along the length L4, any one of the length L4, angle $\alpha 3$ and radius of curvature $RoC_3$ may be specified by specifying the other two variables.

The mechanical properties of force dampening section 44 and the deflectable section 34 in terms of axial stiffness, torsional stiffness, and flexibility can be comparable. However, the force dampening section 44 can be sized and configured to be less stiff and, importantly, to possess greater flexibility than the deflectable section 34.

In the embodiment just described (and as shown in FIG. 7D), the distal end region 20 may comprise a first flexure zone 32, a deflectable section 34, and a force dampening section 44. The first flexure zone, deflection section, and force dampening section function independently from each other, so that the distal end region 20 of the elongated shaft 16 can, in use, be placed into a more compound, complex, multi-bend structure 36. The compound, complex, multi-bend structure 36 comprises a first deflection region at the access angle $\alpha 1$ over a length L2 (the first flexure zone 32); an second deflection region at the contact angle $\alpha 2$ over a length L3 (the deflectable section 34); and a third deflection region at the treatment angle $\alpha 3$ over a length L4 (the force dampening section 44). In the compound, complex, multi-bend structure 36, all lengths L2, L3, and L4 and all angles $\alpha 1$, $\alpha 2$, and $\alpha 3$ can differ. This is because the angle $\alpha 1$ and length L2 are specially sized and configured to gain access from an aorta into a respective renal artery through a femoral artery access point; the angle $\alpha 2$ and length L3 are specially sized and configured to align an energy delivery element 24 element with an interior wall inside the renal artery; and the angle $\alpha 3$ and length L4 are specially sized and configured to optimize surface contact between tissue and the energy delivery element/heat transfer element.

The composite length of L2, L3 and L4 of the first flexure zone, deflectable section and force dampening section, respectively, of the distal end region 20, along with the length L1 of the force transmitting section 30 and the length L5 (see FIG. 11A) of the energy delivery element 24 (i.e., the composite length equal to L1+L2+L3+L4+L5), specifies a working length of the elongated shaft 16 of the treatment device 12. In some representative embodiments, this working length is about 40 cm to about 125 cm. In a representative embodiment where no guide catheter is used, then this working length may be about 40 cm to about 50 cm. If, alternatively, a 55 cm length guide catheter is used, then this working length may be about 70 cm to about 80 cm. If a 90 cm length guide catheter is used, then this working length may be about 105 cm to about 115 cm.

C. Size and Configuration of the Energy Delivery Element for Achieving Neuromodulation in a Renal Artery In some patients, it may be desirable to create multiple focal lesions that are circumferentially spaced along the longitudinal axis of the renal artery. However, it should be understood that a single focal lesion with desired longitudinal and/or circumferential dimensions, one or more full-circle lesions, multiple circumferentially spaced focal lesions at a common longitudinal position, and/or multiple longitudinally spaced focal lesions at a common circumferential position alternatively or additionally may be created.

Creating multiple focal lesions that are circumferentially spaced along the longitudinal axis of the renal artery avoids the creation of a full-circle lesion, thereby reducing a risk of vessel stenosis, while still providing the opportunity to circumferentially treat the renal plexus, which is distributed about the renal artery. It is desirable for each lesion to cover at least 10% of the vessel circumference to increase the probability of affecting the renal plexus. However, it is important that each lesion not be too large (e.g., >60% of vessel circumference) lest the risk of a stenotic effect increases (or other undesirable healing responses such as thrombus formation or collateral damage). In one embodiment the energy delivery element 24 is configured to create a lesion at least 30% (i.e., greater than or equal to 30%) of the vessel circumference. In another embodiment, the energy delivery element 24 is configured to create a lesion of greater than or equal to 30% but less than 60% of the vessel circumference. It is also important that each lesion be sufficiently deep to penetrate into and beyond the adventitia to thereby affect the renal plexus. However, lesions that are too deep (e.g., >5 mm) run the risk of interfering with non-target tissue and tissue structures (e.g., renal vein) so a controlled depth of thermal treatment is desirable.

As described in greater detail below, energy delivery element 24 may be delivered to a first treatment site within the renal artery such that the energy delivery element 24 is positioned in contact with an interior wall of the artery for treating the renal plexus (see FIG. 24C). Once positioned within the artery as desired, energy may be delivered via the energy delivery element to create a first focal lesion at this first treatment site (see FIG. 24D). The first focal lesion creates a first treatment zone 98a that is not continuous completely around the circumference of the renal artery in a radial plane or cross-section normal to the wall or to the longitudinal axis of the artery (i.e., the first focal lesion does not extend all the way around the circumference of the vessel wall). As a result, there is a discrete untreated zone about the circumference of the artery in the radial plane of the first treatment zone normal to the longitudinal axis of the artery.

Figure 24C:
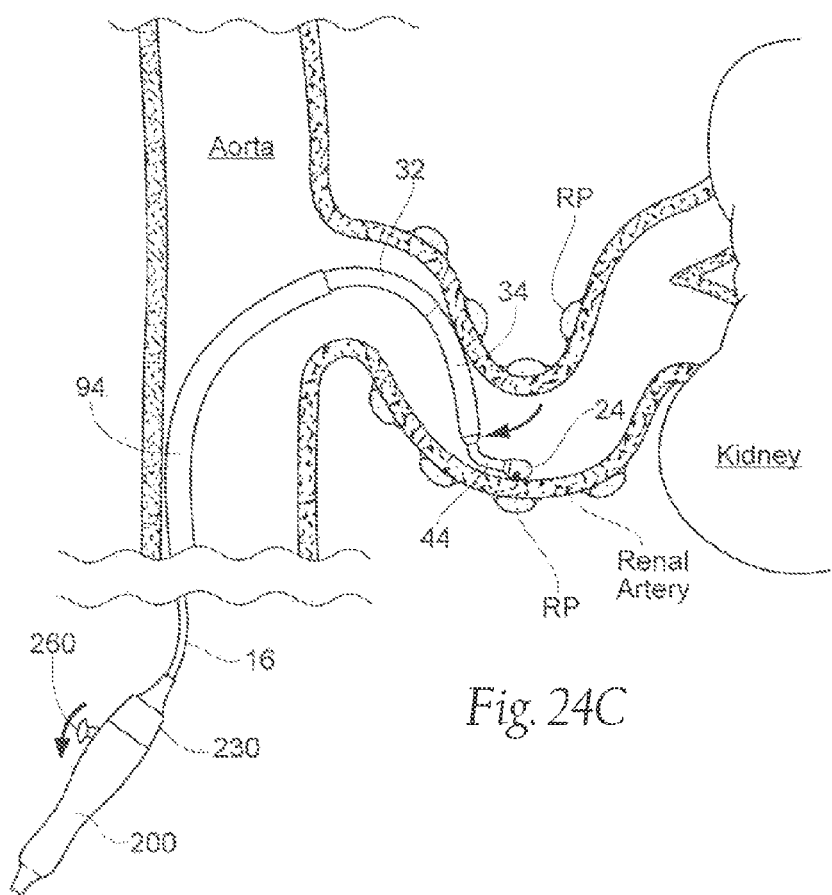
Figure 24D:
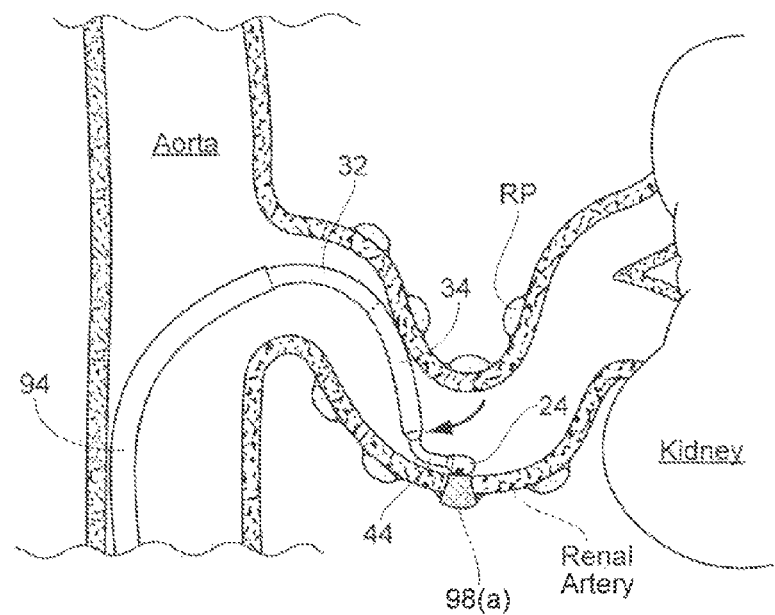
Figure 24E:
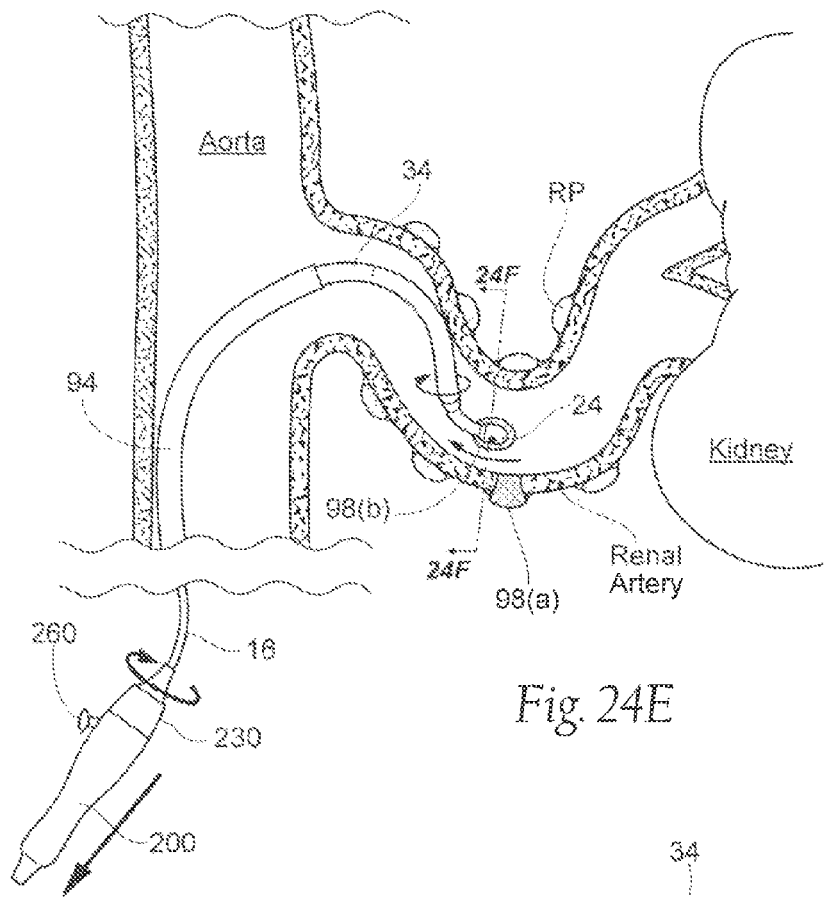
Figure 24F:
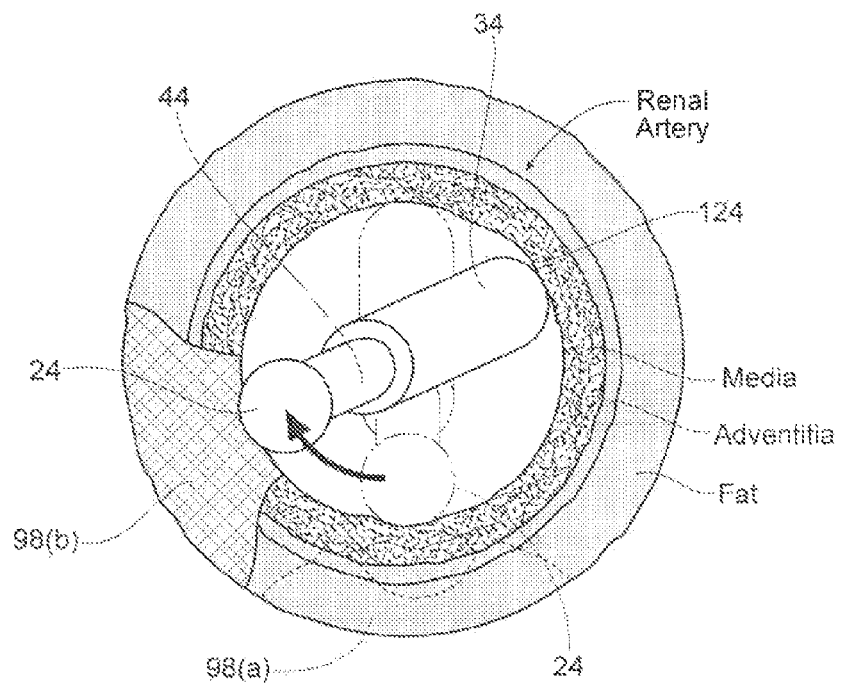

After formation of the first focal lesion at the first treatment zone 98a, the energy delivery element 24 optionally may be angularly repositioned relative to the renal artery (see FIGS. 24E and 24F). This angular repositioning may be achieved, for example, by angularly rotating the elongated shaft 16 of treatment device 12 via handle assembly 200 (see FIG. 17A). In addition to angular repositioning of the energy delivery element 24, the energy delivery element optionally may be repositioned along the lengthwise or longitudinal dimension of the renal artery (see FIG. 24E). This longitudinal repositioning may be achieved, for example, by translating the elongated shaft 16 of treatment device 12 via handle assembly 200, and may occur before, after or concurrent with angular repositioning of the energy delivery element 24.

Repositioning the energy delivery element 24 in both the longitudinal and angular dimensions places the energy delivery element in contact with the interior wall of the renal artery at a second treatment site for treating the renal plexus (see FIG. 24E). Energy then may be delivered via the energy delivery element to form a second focal lesion at this second treatment site, thereby creating a second treatment zone 98b and a second untreated zone (see FIG. 24F).

As with the first treatment zone created by the first focal lesion, the second treatment zone is not continuous about the complete circumference of the renal artery. However, the first and second treatment zones (as well as the first and second untreated zones) are angularly and longitudinally offset from one another about the angular and lengthwise dimensions of the renal artery, respectively (see FIG. 24G). Superimposing the first and second treatment zones, which are positioned along different cross-sections or radial planes of the renal artery, about a common cross-section provides a composite treatment zone that covers a greater portion of the circumference of the artery than either treatment zone individually. As this composite treatment zone is not continuous (i.e., it is formed from multiple, longitudinally and angularly spaced treatment zones), it is expected that a greater portion of the circumference of the arterial wall may be treated with reduced risk of vessel stenosis, as compared to formation of a single focal lesion covering an equivalent portion of the arterial circumference at a single treatment site (i.e., at a single lengthwise position or about a single cross-section of the renal artery).

One or more additional focal lesions optionally may be formed at one or more additional angularly and longitudinally spaced treatment sites to created additional angularly and longitudinally spaced treatment zones (see FIGS. 24E-24H). In one representative embodiment, superimposition of all or a portion of the treatment zones provides a composite treatment zone that is non-continuous (i.e., that is broken up along the lengthwise dimension or longitudinal axis of the renal artery), yet that is substantially circumferential (i.e., that substantially extends all the way around the circumference of the renal artery over a lengthwise segment of the artery). This superimposed treatment zone beneficially does not create a continuous circumferential lesion along any individual radial plane or cross-section normal to the artery, which may reduce a risk of acute or late stenosis formation, as compared to circumferential treatments that create such continuous circumferential lesions.

Non-continuous circumferential treatment by positioning energy delivery element(s) at different angular orientations along multiple lengthwise locations may preferentially affect anatomical structures that substantially propagate along the lengthwise dimension of the artery. Such anatomical structures can be neural fibers and/or structures that support the neural fibers (e.g., the renal plexus). Furthermore, such non-continuous circumferential treatment may mitigate or reduce potentially undesirable effects induced in structures that propagate about the angular dimension of the artery, such as smooth muscle cells. Were a continuous circumferential lesion alternatively to be formed, the angular or circumferential orientation of the smooth muscle cells relative to the artery may increase a risk of acute or late stenosis or acute vessel spasm.

Figure 6C:
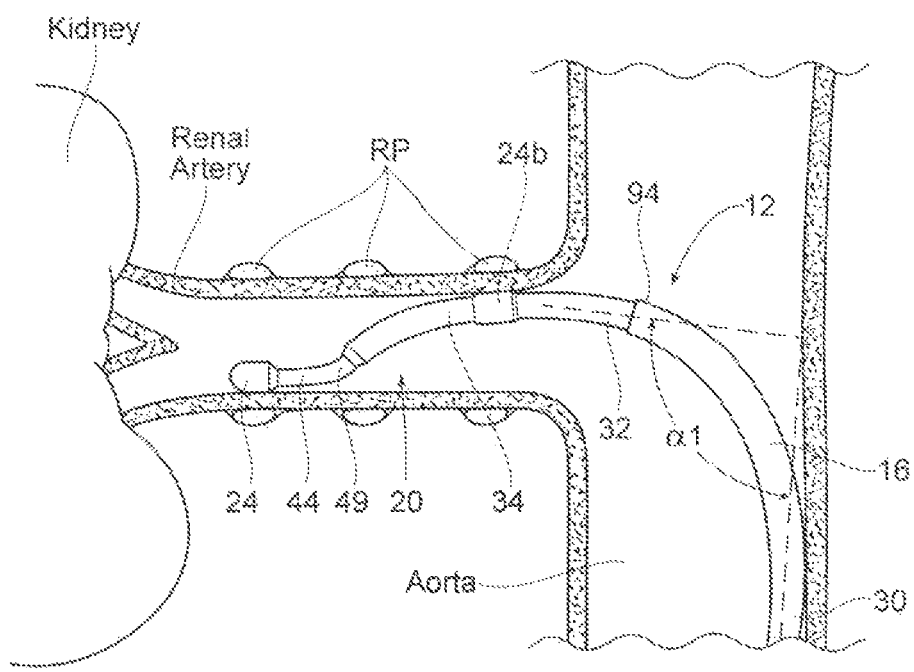

In multi-energy delivery element configurations (e.g., multi-electrode configurations), such as in FIG. 6C, multiple non-continuous circumferential treatment zones can be created during a single catheter placement within the renal artery. The multiple energy delivery elements can be spaced and located such that they are longitudinally and angularly spaced apart from one another and such that they create longitudinally offset and angularly opposed or offset treatment zones. Retraction and rotation of the treatment device 12 can reposition the energy delivery elements to create additional longitudinally and angularly separated treatment zones, thereby allowing the practitioner the ability to create multiple treatment zones per catheter placement and several treatment zones via only two catheter placements.

Figure 11B:
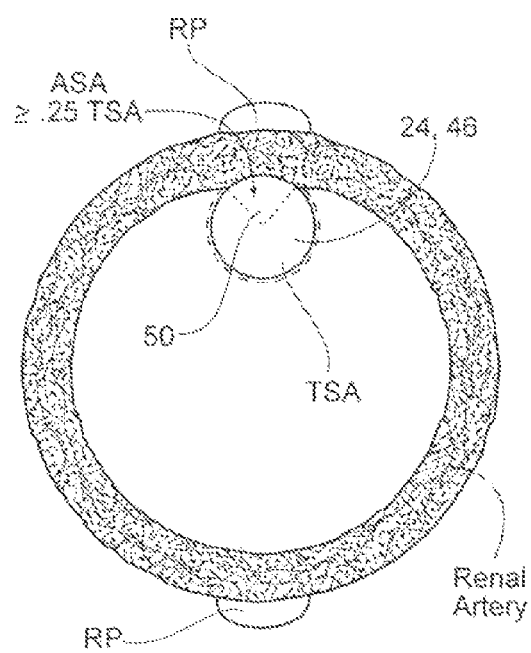

As described (and as FIG. 11A shows), the energy delivery element 24 is sized and configured, in use, to contact an internal wall of the renal artery. In the illustrated embodiment (see FIG. 11B), the energy delivery element 24 takes the form of an electrode 46 sized and configured to apply an electrical field comprising radiofrequency (RF) energy from the generator 26 to a vessel wall. In the illustrated embodiment, the electrode 46 is operated in a monopolar or unipolar mode. In this arrangement, a return path for the applied RF electric field is established, e.g., by an external dispersive electrode (shown as 38 in FIG. 6A), also called an indifferent electrode or neutral electrode. The monopolar application of RF electric field energy serves to ohmically or resistively heat tissue in the vicinity of the electrode 46. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall, which is shown, e.g., in FIG. 12B. Alternatively, a RF electrical field can be delivered with an oscillating intensity that does not thermally injure the tissue whereby neuromodulation in the targeted nerves is accomplished by electrical modification of the nerve signals.

The active surface area of contact (ASA) between the energy delivery element 24 or electrode 46 and the vessel wall has great bearing on the efficiency and control of the transfer of a thermal energy field across the vessel wall to thermally affect targeted neural fibers in the renal plexus (RP). The active surface area of the energy delivery element 24 and electrode 46 is defined as the energy transmitting area of the element 24 or electrode 46 that can be placed in intimate contact against tissue. Too much contact between the energy delivery element and the vessel wall and/or too much power may create unduly high temperatures at or around the interface between the tissue and the energy delivery element, thereby creating excessive heat generation at this interface and/or spasm and contraction of the vessel wall. This excessive heat can also create a lesion that is circumferentially too large, increasing the risk of stenosis. This excessive heat can also lead to undesirable thermal damage at the vessel wall, which stiffens and desiccates the vessel tissue making it more susceptible to puncture and perforation. Additionally, the tissue desiccation (i.e., dehydration) reduces the electrical and thermal conductivity of the tissue. Reduced conductivity may potentially create a lesion that is too shallow to reach the neural fibers and may also result in the buildup of excessive heat, causing increased and undesirable damage to the vessel wall and increasing the likelihood of thrombus formation. Although the risks of excessive wall contact and heating are many, too little contact between the energy delivery element and the vessel wall may impair the efficacy of the treatment. For example, too little contact may result in superficial heating of the vessel wall, thereby creating a lesion that is too small (e.g., <10% of vessel circumference) and/or too shallow to reach the target renal neural fibers.

While the active surface area (ASA) of the energy delivery element 24 and electrode 46 is important to creating lesions of desirable size and depth, the ratio between the active surface area (ASA) and total surface area (TSA) of the energy delivery element 24 and electrode 46 is also important. The ASA to TSA ratio influences lesion formation in two ways: (1) the degree of resistive heating via the electric field, and (2) the effects of blood flow or other convective cooling elements such as injected or infused saline. As discussed above, the RF electric field causes lesion formation via resistive heating of tissue exposed to the electric field. The higher the ASA to TSA ratio (i.e., the greater the contact between the electrode and tissue), the greater the resistive heating. As discussed in greater detail below, the flow of blood over the exposed portion of the electrode (TSA-ASA) provides conductive and convective cooling of the electrode, thereby carrying excess thermal energy away from the interface between the vessel wall and electrode. If the ratio of ASA to TSA is too high (e.g., 50%), resistive heating of the tissue can be too aggressive and not enough excess thermal energy is being carried away, resulting in excessive heat generation and increased potential for stenotic injury, thrombus formation and undesirable lesion size. If the ratio of ASA to TSA is too low (e.g., 10%), then there is too little resistive heating of tissue, thereby resulting in superficial heating and smaller and shallower lesions.

Various size constraints for the energy delivery element 24 may be imposed for clinical reasons by the maximum desired dimensions of the guide catheter, as well as by the size and anatomy of the renal artery itself. Typically, the maximum outer diameter (or cross-sectional dimension for non-circular cross-section) of the electrode 46 comprises the largest diameter encountered along the length of the elongated shaft 16 distal to the handle assembly 200. Thus, the outer diameters of the force transmitting section 30, first flexure zone 32, deflection section 34 and force dampening section 44 are equal to or (desirably) less than the maximum outer diameter of the electrode 46.

In a representative embodiment shown in FIG. 11A, the electrode 46 takes the form of a right circular cylinder, possessing a length L5 that is greater than its diameter. The electrode 46 further desirably includes a distal region that is rounded to form an atraumatic end surface 48. In the representative embodiment shown in FIG. 11B, the electrode 46 is spherical in shape, such that the length L5 is equal to the electrode's diameter. The spherical shape, too, presents an atraumatic surface to the tissue interface.

As shown in FIG. 8A, the angle $\alpha 3$ and length L4 of the distal assembly 53 are specially sized and configured, given the TSA of the respective electrode, to optimize an active surface area of contact between tissue and the respective electrode 46 (ASA). The angle $\alpha 3$ and the length L4 of the distal assembly 53 make it possible to desirably lay at least a side quadrant 50 of the electrode 46 against tissue (see FIG. 12A), though it should be understood that the electrode 46 does not necessarily need to be positioned with its side quadrant 50 against tissue prior to power delivery. In a representative embodiment, the active surface area of the electrode 46 contacting tissue (ASA) can be expressed as ASA≥0.25 TSA and ASA≤0.50 TSA.

An ASA to TSA ratio of over 50% may be effective with a reduced power delivery profile. Alternatively, increasing the convective cooling of the electrode that is exposed to blood flow can compensate for a higher ASA to TSA ratio. As discussed further below, this could be achieved by injecting or infusing cooling fluids such as saline (e.g., room temperature saline or chilled saline) over the electrode and into the blood stream.

The stiffnesses of each of the deflectable section 34 and force dampening section 44 are also selected to apply via the electrode a stabilizing force that positions the electrode 46 in substantially secure contact with the vessel wall tissue. This stabilizing force also influences the amount of wall contact achieved by the energy delivery element (i.e., the ASA to TSA ratio). With greater stabilizing force, the energy delivery element has more wall contact and with less stabilizing force, less wall contact is achieved. Additional advantages of the stabilizing force include, (1) softening the contact force between the distal end 20 and vessel wall to minimize risk of mechanical injury to vessel wall, (2) consistent positioning of the electrode 46 flat against the vessel wall, and (3) stabilizing the electrode 46 against the vessel wall. As discussed above with respect to the combined effect of the first flexure zone and second/deflectable section, this stabilizing force allows the catheter treatment device to maintain consistent contact with the vessel wall even during motion of the renal artery during respiration. The stabilizing force also allows the electrode to return to a neutral position after the electrode is removed from contact with the wall.

As previously discussed, for clinical reasons, the maximum outer diameter (or cross-sectional dimension) of the electrode 46 is constrained by the maximum inner diameter of the guide catheter through which the elongated shaft 16 is to be passed through the intravascular path 14. Assuming that an 8 French guide catheter 94 (which has an inner diameter of approximately 0.091 inches) is, from a clinical perspective, the largest desired catheter to be used to access the renal artery, and allowing for a reasonable clearance tolerance between the electrode 46 and the guide catheter, the maximum diameter of the electrode 46 is constrained to about 0.085 inches. In the event a 6 French guide catheter is used instead of an 8 French guide catheter, then the maximum diameter of the electrode 46 is constrained to about 0.070 inches. In the event a 5 French guide catheter is used, then maximum diameter of the electrode 46 is constrained to about 0.053 inches. Based upon these constraints and the aforementioned power delivery considerations, the electrode 46 desirably has a maximum outer diameter of from about 0.049 to about 0.051 inches. The electrode 46 also desirably has a minimum outer diameter of about 0.020 inches to provide sufficient cooling and lesion size. In some embodiments, the electrode 46 (i.e., the energy delivery element 24) may have a length of about 1 mm to about 3 mm. In some embodiments in which the energy delivery element is a resistive heating element, it can have a maximum outer diameter from about 0.049 to 0.051 inches and a length of about 10 mm to 30 mm.

D. Applying Energy to Tissue Via the Energy Delivery Element

Referring back to FIG. 5, in the illustrated embodiment, the generator 26 may supply to the electrode 46 a pulsed or continuous RF electric field. Although a continuous delivery of RF energy is desirable, the application of thermal energy in pulses may allow the application of relatively higher energy levels (e.g., higher power), longer or shorter total duration times, and/or better controlled intravascular renal neuromodulation therapy. Pulsed energy may also allow for the use of a smaller electrode.

The thermal therapy may be monitored and controlled, for example, via data collected with one or more sensors 52, such as temperature sensors (e.g., thermocouples, thermistors, etc.), impedance sensors, pressure sensors, optical sensors, flow sensors, chemical sensors, etc. (see FIGS. 12A and 12B). Sensor(s) 52 may be incorporated into or on electrode 46 and/or in/on adjacent areas on the distal end region 20 and/or distal assembly 53.

Advantageously, since the deflectable section 34 deflects in a controlled manner, the surface of electrode 46 that contacts tissue during treatment may be known. As such, sensor(s) 52 may be incorporated into the electrode in a manner that specifies whether the sensor(s) are in contact with tissue at the treatment site and/or are facing blood flow. The ability to specify sensor placement relative to tissue and blood flow is highly significant, since a temperature gradient across the electrode from the side facing blood flow to the side in contact with the vessel wall may be up to about 15° C. Significant gradients across the electrode in other sensed data (e.g., flow, pressure, impedance, etc.) also are expected.

The sensor(s) 52 may, for example, be incorporated on the side of the electrode that contacts the vessel wall at the treatment site during power and energy delivery (see FIG. 12B), may be incorporated into the tip of the electrode, may be incorporated on the opposing side of the electrode that faces blood flow during energy delivery (see FIG. 12A), and/or may be incorporated within certain regions of the electrode (e.g., distal, proximal, quandrants, etc.). In some embodiments, multiple sensors may be provided at multiple positions along the electrode and/or relative to blood flow. For example, a plurality of circumferentially and/or longitudinally spaced sensors may be provided. In one embodiment, a first sensor may contact the vessel wall during treatment, and a second sensor may face blood flow.

Additionally or alternatively, various microsensors can be used to acquire data corresponding to the energy delivery element, the vessel wall and/or the blood flowing across the energy delivery element. For example, arrays of micro thermocouples and/or impedance sensors can be implemented to acquire data along the energy delivery element or other parts of the treatment device. Sensor data can be acquired or monitored prior to, simultaneous with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

Figure 12B:
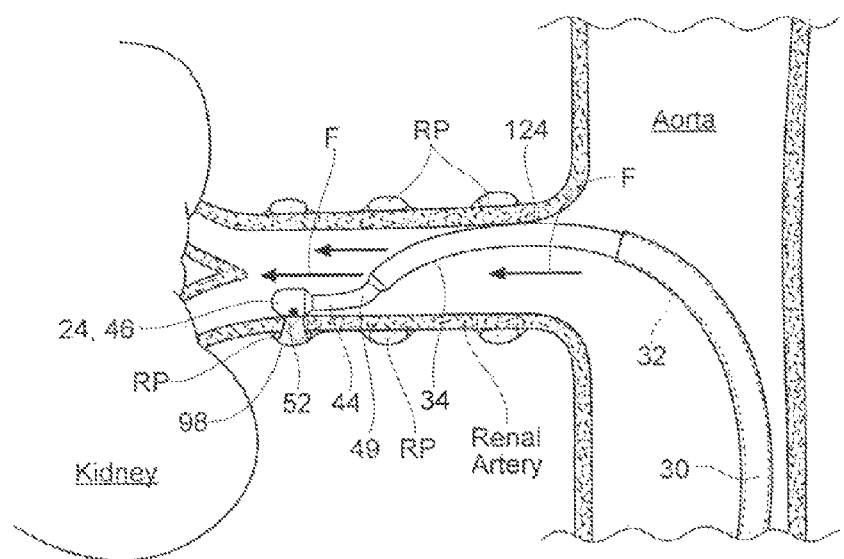

Non-target tissue may be protected by blood flow (F) within the respective renal artery that serves as a conductive and/or convective heat sink that carries away excess thermal energy. For example (as FIGS. 12A and 12B show), since blood flow (F) is not blocked by the elongated shaft 16 and the electrode 46 it carries, the native circulation of blood in the respective renal artery serves to remove excess thermal energy from the non-target tissue and the energy delivery element. The removal of excess thermal energy by blood flow also allows for treatments of higher power, where more power can be delivered to the target tissue as thermal energy is carried away from the electrode and non-target tissue. In this way, intravascularly-delivered thermal energy heats target neural fibers located proximate to the vessel wall to modulate the target neural fibers, while blood flow (F) within the respective renal artery protects non-target tissue of the vessel wall from excessive or undesirable thermal injury. When energy is delivered in pulses, the time interval between delivery of thermal energy pulses may facilitate additional convective or other cooling of the non-target tissue of the vessel wall compared to applying an equivalent magnitude or duration of continuous thermal energy.

It may also be desirable to provide enhanced cooling by inducing additional native blood flow across the energy delivery element. For example, techniques and/or technologies can be implemented by the caregiver to increase perfusion through the renal artery or to the energy delivery element itself. These techniques include positioning partial occlusion elements (e.g., balloons) within upstream vascular bodies such as the aorta or proximal portion of the renal artery to improve flow across the energy delivery element.

In addition, or as an alternative, to passively utilizing blood flow (F) as a heat sink, active cooling may be provided to remove excess thermal energy and protect non-target tissues. For example, a thermal fluid infusate may be injected, infused, or otherwise delivered into the vessel in an open circuit system. Additionally or alternatively, the energy delivery element 24 (e.g., electrode 46) may be actively cooled in a closed circuit system (i.e., without delivering any agents into the bloodstream) to remove excess thermal energy, such as by circulating a thermal fluid infusate (e.g., a cryogenic or chilled fluid) within the distal end region 20 or by some other mechanism.

Thermal fluid infusates used for active cooling may, for example, comprise (room temperature or chilled) saline or some other biocompatible fluid. The thermal fluid infusate(s)

may, for example, be introduced through the treatment device 12 via one or more infusion lumens and/or ports. When introduced into the bloodstream, the thermal fluid infusate(s) may, for example, be introduced through a guide catheter at a location upstream from the energy delivery element 24 or electrode 46, or at other locations relative to the tissue for which protection is sought. The delivery of a thermal fluid infusate in the vicinity of the treatment site (via an open circuit system and/or via a closed circuit system) may, for example, allow for the application of increased/higher power, may allow for the maintenance of lower temperature at the vessel wall during energy delivery, may facilitate the creation of deeper or larger lesions, may facilitate a reduction in treatment time, may allow for the use of a smaller electrode size, or a combination thereof.

Although many of the embodiments described herein pertain to electrical systems configured for the delivery of RF energy, it is contemplated that the desired treatment can be accomplished by other means, e.g., by coherent or incoherent light; direct thermal modification (e.g., with a heated or cooled fluid or resistive heating element); microwave; ultrasound (including high intensity focused ultrasound); diode laser; radiation; a tissue heating fluid; and/or a cryogenic fluid.

III. Representative Embodiments

A. First Representative Embodiment (First Flexure Zone, Deflectable Section, Force Redirecting Element, Force Dampening Section, and Energy Delivery Element)

FIGS. 10A to 17B show a representative embodiment of an elongated shaft 16 that includes a force transmitting section 30, as well as first flexure zone 32, deflectable section 34, and distal assembly 53, having the physical and mechanical features described above. In this embodiment, the distal assembly 53 comprises a force redirecting element 49, a force dampening section 44, and an energy delivery element 24, wherein the force redirecting element 49 is part of the force dampening section 44 and is located near the proximal end of the force dampening section 44 (see, e.g., FIG. 14A).

1. Force Transmitting Section

In the illustrated embodiment, as shown in FIGS. 13A and 13B, the force transmitting section 30 comprises a first elongated and desirably tubular structure, which can take the form of, e.g., a first tubular structure 54. The first tubular structure 54 is desirably a hypo tube that is made of a metal material, e.g. of stainless steel, or a shape memory alloy, e.g., nickel titanium (a.k.a., Nitinol or NiTi), to possess the requisite axial stiffness and torsional stiffness, as already described, for the force transmitting section 30. As already described, the force transmitting section 30 comprises the most stiff section along the elongated shaft 16, to facilitate axially movement of the elongated shaft 16, as well as rotational manipulation of the elongated shaft 16 within the intravascular path 14. Alternatively, the first tubular structure 54 may comprise a hollow coil, hollow cable, solid cable (w/embedded wires), a braided or braid reinforced shaft, a coil reinforced polymer shaft, a metal/polymer composite, etc.

The stiffness is a function of material selection as well as structural features such as interior diameter, outside diameter, wall thickness, geometry and other features that are made by micro-engineering, machining, cutting and/or skiving the hypo tube material to provide the desired axial and torsional stiffness characteristics. For example, the elongated shaft can be a hypo tube that is laser cut to various shapes and cross-sectional geometries to achieve the desired functional properties.

When the first tubular structure 54 is made from an electrically conductive metal material, the first tubular structure 54 may include a sheath 56 or covering made from an electrically insulating polymer material or materials, which is placed over the outer diameter of the underlying tubular structure. The polymer material can also be selected to possess a desired durometer (expressing a degree of stiffness or lack thereof) to contribute to the desired overall stiffness of the first tubular structure 54. Candidate materials for the polymer material include, but are not limited to, polyethylene terephthalate (PET); polyethylene block amide copolymer; nylon; polyurethane; transparent thermoplastic polyamide sold under the trademark GRILAMID; or combinations thereof. The polymer material can be laminated, dip-coated, spray-coated, or otherwise deposited/attached to the outer diameter of the tube.

2. First Flexure Zone

As FIGS. 14A, 14B, and 14C show, the first flexure zone 32 comprises a second elongated and desirably tubular structure, which can take the form of, e.g., a second tubular structure 58. The second tubular structure 58 can be made from the same or different material as the first tubular structure 54. The axial stiffness and torsional stiffness of the second tubular structure 58 possesses the requisite axial stiffness and torsional stiffness, as already described, for the first flexure zone 32. As already described, the first flexure zone 32 may be less stiff and more flexible than the force transmitting section 30, to navigate the severe bend at and prior to the junction of the aorta and respective renal artery. The second tubular structure is desirably a hypo tube, but can alternatively comprise a hollow coil, hollow cable, braided shaft, etc.

It may be desirable for the first and second tubular structures 54 and 58 to share the same material. In this event, the form and physical features of the second tubular structure 58 may be altered, compared to the first tubular structure 54, to achieve the desired stiffness and flexibility differences. For example, the interior diameter, outside diameter, wall thickness, and other engineered features of the second tubular structure 58 can be tailored to provide the desired axial and torsional stiffness and flexibility characteristics. For example, the second tubular structure 58 can be laser cut along its length to provide a bendable, spring-like structure. Depending on the ease of manufacturability the first and second tubular structures may be produced from the same piece of material or from two separate pieces. In the event the first tubular structure and second tubular structure are not of the same material, the outside diameter of the second tubular structure 58 can be less than the outer diameter of first tubular structure 54 (or have a smaller wall thickness) to create the desired differentiation in stiffness between the first and second tubular structures 54 and 58.

When the second tubular structure 58 is made from an electrically conductive metal material, the second tubular structure 58, like the first tubular structure 54, includes a sheath 60 (see FIGS. 14B and 14C) or covering made from an electrically insulating polymer material or materials, as already described. The sheath 60 or covering can also be selected to possess a desired durometer to contribute to the desired differentiation in stiffness and flexibility between the first and second tubular structures 58.

The second tubular structure 58 can comprise a different material than the first tubular structure 54 to impart the desired differentiation in stiffness and flexibility between the first and second tubular structures 58. For example, the second tubular structure 58 can comprise a cobalt-chromium-nickel alloy, instead of stainless steel. Alternatively, the second tubular structure 58 can comprise a less rigid polymer, a braided or braid-reinforced shaft, a coil reinforced polymer shaft, a metal/polymer composite, nitinol or hollow cable-like structure. In addition to material selection, the desired differentiation in stiffness and overall flexibility can be achieved by selection of the interior diameter, outside diameter, wall thickness, and other engineered features of the second tubular structure 58, as already described. Further, a sheath 60 or covering made from an electrically insulating polymer material, as above described, can also be placed over the outer diameter of the second tubular structure 58 to impart the desired differentiation between the first and second tubular structures 54 and 58.

3. Deflectable Section

As FIGS. 15A, 15B, 15C, and 15D show, the deflectable section 34 comprises a third elongated and desirably tubular structure, which can take the form of, e.g., a third tubular structure 62. The third tubular structure 62 can be made from the same or different material as the first and/or second tubular structures 54 and 58. The axial stiffness and torsional stiffness of the third tubular structure 62 possesses the requisite axial stiffness and torsional stiffness, as already described, for the deflectable section 34. As already described, the deflectable section 34 may be less stiff and more flexible than the first flexure zone 32, to facilitate controlled deflection of the deflectable section 34 within the respective renal artery.

If the second and third tubular structures 58 and 62 share the same material, the form and physical features of the third tubular structure 62 are altered, compared to the second tubular structure 58, to achieve the desired stiffness and flexibility differences. For example, the interior diameter, outside diameter, wall thickness, and other engineered features of the third tubular structure 62 can be tailored to provide the desired axial and torsional stiffness and flexibility characteristics. For example, the third tubular structure 62 can be laser cut along its length to provide a more bendable, more spring-like structure than the second tubular structure 58.

When the third tubular structure 62 is made from an electrically conductive metal material, the third tubular structure 62 also may include a sheath 64 (see FIGS. 15B, 15C, and 15D) or covering made from an electrically insulating polymer material or materials, as already described. The sheath 64 or covering can also be selected to possess a desired durometer to contribute to the desired differentiation in stiffness and flexibility between the second and third tubular structure 62.

The third tubular structure 62 can comprise a different material than the second tubular structure to impart the desired differentiation in stiffness and flexibility between the second and third tubular structures 62. For example, the third tubular structure 62 can include a Nitinol material, to impart the desired differentiation in stiffness between the second and third tubular structures 58 and 62. In addition to material selection, the desired differentiation in stiffness and overall flexibility can be achieved by selection of the interior diameter, outside diameter, wall thickness, and other engineered features of the third tubular structure 62, as already described.

For example, in diameter, the outside diameter of the third tubular structure 62 is desirably less than the outer diameter of second tubular structure 58. Reduction of outside diameter or wall thickness influences the desired differentiation in stiffness between the second and third tubular structures 58 and 62.

As discussed in greater detail above, preferential deflection of the deflectable section is desirable. This can be achieved by making the third tubular structure 62 compressible in the desired direction of deflection and resilient to compression opposite the direction of deflection. For example, as shown in FIGS. 15B and 15C, the third tubular structure 62 (unlike the second tubular structure 58) can include a laser-cut pattern that includes a spine 66 with connecting ribs 68. The pattern biases the deflection of the third tubular structure 62, in response to pulling on the control wire 40 coupled to the distal end of the third tubular structure 62, toward a desired direction. The control wire 40 is attached to a distal end of the deflectable section with solder 130. When the control wire is pulled the third tubular structure compresses on the compressible side biasing deflection in the direction of the compressible side. The benefits of preferential deflection within a renal artery have already been described.

As also shown in FIG. 15D, a flat ribbon material 70 (e.g., Nitinol, stainless steel, or spring stainless steel) can be attached to the third tubular structure 62. When the pulling force is removed from the control wire 40, the flat ribbon, which serves to reinforce the deflectable third tubular structure 62, will elastically straighten out the deflectable third tubular structure 62.

Further, a sheath 64 (see FIGS. 15B, 15C, and 15D) or covering made from an electrically insulating polymer material, as above described, and having a desired durometer can also be placed over the outer diameter of the second tubular structure 58 to impart the desired differentiation between the first and second tubular structures 54 and 58.

In the embodiment of FIGS. 15B-15D, the width of the spine 66 (i.e., the radial arc length of the spine 66 at regions along the longitudinal axis of the third tubular structure 62 that do not include ribs 68) affects the relative stiffness and elasticity of the third tubular structure 62. It should be understood that the width of the spine 66 may be specified to provide the third tubular structure 62 with a desired relative stiffness and/or elasticity. Furthermore, the width of the spine 66 may vary along the longitudinal axis of the third tubular structure 62, thereby providing the third tubular structure with a varying relative stiffness and/or elasticity along its length. Such variation in the width of the spine 66 may be gradual, continuous, abrupt, discontinuous, or combinations thereof.

The length L3 of the deflectable section 34 is between about 5 mm and 20 mm, for example less than or equal to about 12.5 mm. As the distal end region 20 is advanced from a guide catheter into a renal artery the energy delivery element 24 contacts the superior surface of the renal artery wall. The length L3 allows the energy delivery element 24 to be manipulated through deflection of the deflectable section 34 to contact dorsal, ventral and inferior surfaces of the renal artery wall within a short distance as long as a portion of the deflectable section 34 protrudes from the guide catheter. Thus the length L3 of the deflectable section 34 is chosen to be specially suited for use in a renal artery.

The width of the ribs 68 (i.e., the distance spanned by each rib along the longitudinal axis of the third tubular structure 62), as well as the spacing of the ribs 68 (i.e., the distance spanned by the spine 66 along the longitudinal axis of the third tubular member 62 between adjacent ribs 68), optionally may affect a maximal preferential deflection achievable by the deflectable section 34 before adjacent ribs 68 contact one another, i.e. may limit the maximum amount of compression to the side of the third tubular structure that is compressible. Such contact between adjacent ribs 68 optionally may define the radius of curvature and/or the angle α2 (see FIG. 7C) of the deflectable section 34 under such maximal preferential deflection. The deflectable section is configured for a state of maximum flexure, wherein the state of maximum flexure is achieved when the deflectable body moves the energy delivery element away from the axis of the elongated tubular body by a predetermined distance. The maximum flexure avoids the risk of causing trauma to the renal artery wall which could happen if a deflectable section 34 of length L3 were deflected significantly more than the diameter of a renal artery. As will be discussed in more detail later, the force dampening section 44 is configured to dampen force exerted to the artery wall when the deflectable section 34 is deflected. Stable contact force between an energy delivery element 24 and an inner wall of a renal artery can be created by exerting a force that is greater than an instable force and less than a traumatic force. The force dampening section 44 dampens the contact force keeping it within a stable yet atraumatic range even when the deflectable section 34 moves the energy delivery element 24 away from the axis of the elongated tubular body by a distance greater than the diameter of a renal artery. For example, the force dampening section 44 may flex enough for the deflectable section 34 to be configured for a state of maximum flexure such that the predetermined distance is about 4 mm greater than a renal artery diameter. In one embodiment the distal assembly 53 has a length of about 3 mm to 6 mm (e.g. less than or equal to 5 mm), the deflectable section 34 has a length L3 of about 8 mm to 15 mm (e.g. less than or equal to 12.5 mm) and has a maximum flexure displacing the energy delivery element 24 a predetermined distance of about 10 to 14 mm. Alternatively or additionally, the predetermined distance can be adjusted by a deflection limiter in the handle 200 that limits the actuator 260 to displacing the control wire a maximum amount thus limiting the deflection to an adjusted state of maximum flexure.

It should be understood that the width and/or the spacing of the ribs 68 may be specified as desired to achieve a desired maximal preferential deflection. Furthermore, the width and/or the spacing of the ribs 68 may vary along the longitudinal axis of the third tubular structure 62, thereby providing the deflectable section 34 with a varying radius of curvature under such maximal preferential deflection. Such variation in the width and/or spacing of the ribs 68 may be gradual, continuous, abrupt, discontinuous, or combinations thereof.

4. Force Redirecting Element

As shown in FIG. 16A the distal end region 20 comprises a distal assembly 53. Distal assembly 53 comprises a force redirecting element 49, a force dampening section 44 and an energy delivery element 24, wherein the force redirecting element 49 is part of the force dampening section 44 and is located near the proximal end of the force dampening section 44. The force redirecting element 49 comprises a bend in the force dampening section 44 adapted to induce buckling of at least one of the force dampening section 44, deflectable section 34, and a portion of the first flexure zone 32 at a force that is smaller than the maximum force a renal artery wall can withstand before trauma is caused such that the risk of trauma is greatly reduced while advancing the distal end region 20 through a tortuous renal artery. Buckling is facilitated by a) redirecting an axial load to an eccentric load along at least a portion of one of the deflectable section 34 and first flexure zone 32 by distancing the distal end of the energy delivery element 24 from the axis of an effective portion of the deflectable section 34 (and possibly an effective portion of the first flexure zone 32) by a preset angle and distance; or b) by redirecting an axial load to a side load along at least a portion of the force dampening section 44 or deflectable section 34. In this context the effective portion of the deflectable section 34 and first flexure zone 32 refers to the portion that is in the renal artery and is not substantially constrained by a guide catheter or by bends in the renal artery.

Figure 10A:
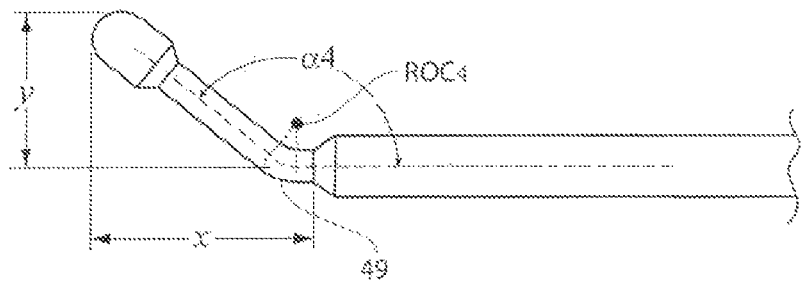
FIGS. 10A to 10E show examples of configurations of force redirecting elements.
Figure 10B:
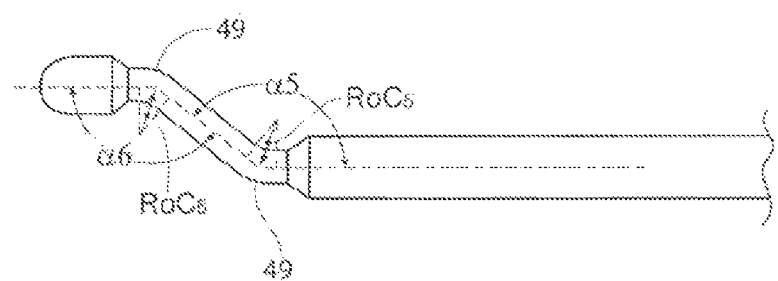
Figure 10C:
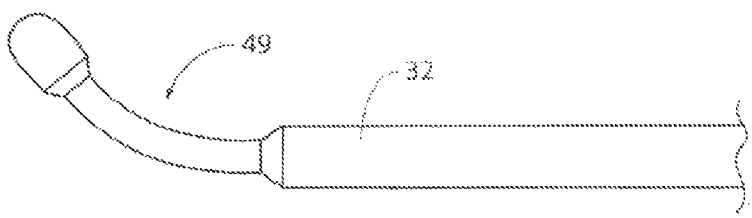
Figure 10D:
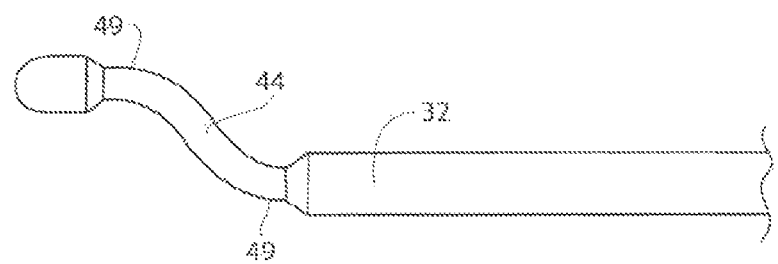
Figure 10E:
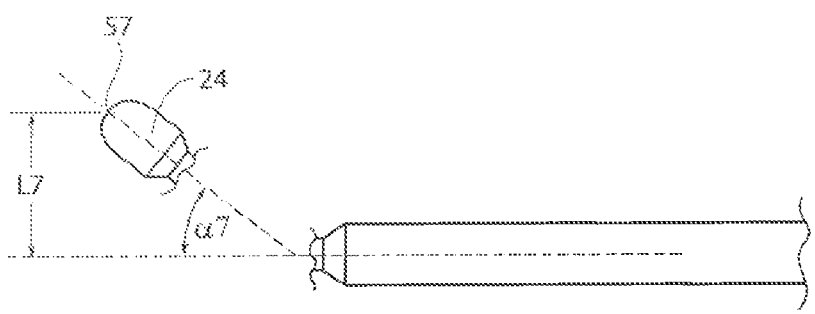

In some embodiments force redirecting element 49 and force dampening section 44 comprise the same structure wherein the force redirecting element is a preformed bend or curve in the force dampening section 44 as shown in FIGS. 10A and 10C. Alternatively, force redirecting element can be two preformed bends or curves in the force dampening section 44 as shown in FIGS. 10B and 10D, or force redirecting element can be any number and combination of bends or curves that distance the distal tip 57 of an energy delivery element 24 from the axis of the elongated body 16 as shown in FIG. 10E.

Figure 16G:
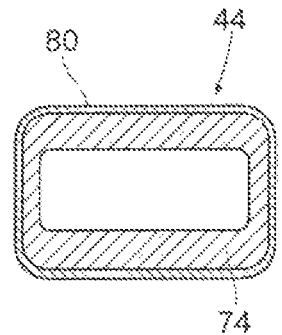
FIGS. 16G and 16H show alternative embodiments of the force dampening section corresponding to the elongated shaft of the treatment device shown in FIG. 5.
Figure 16H:
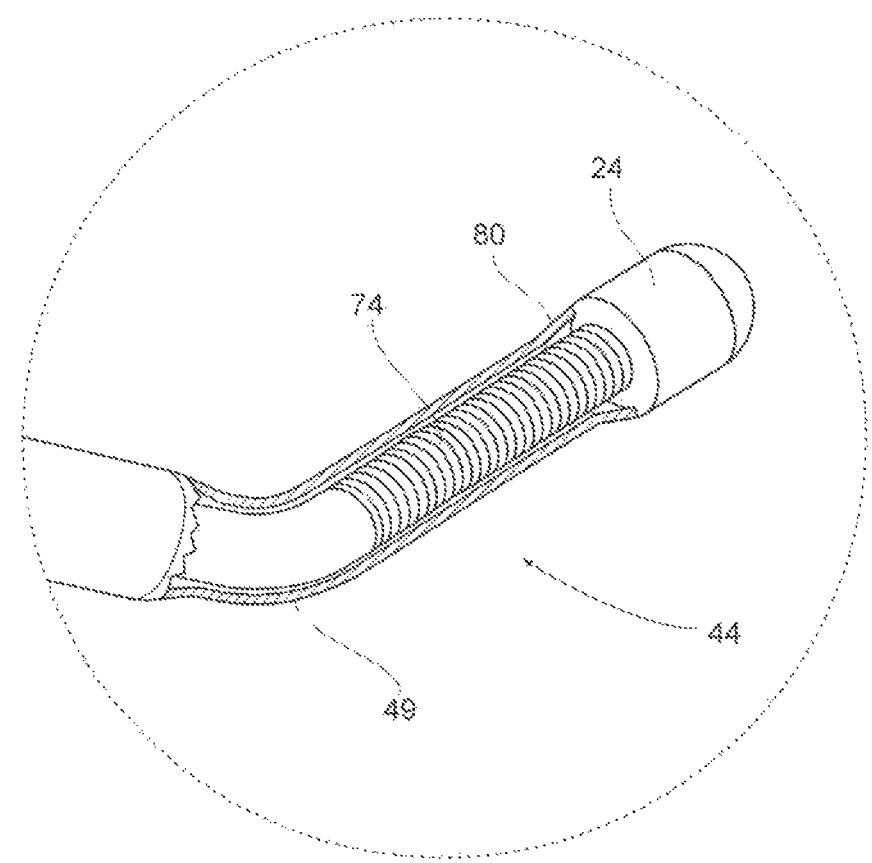

In other embodiments force redirecting element 49 and force dampening section 44 can comprise separate structures. For example, as shown in FIG. 16H force redirecting element 49 is a wire or tube with a preformed angular bend. The force redirecting element can be connected to a separate force dampening section 44, which in FIG. 16H is a spring coil.

Referring to FIG. 10A, a force redirecting element 49 can comprise an angular bend with an angle $\alpha 4$ between about 135° and 170°, for example less than or equal to about 160° and a radius of curvature $RoC_4$ between about 0 mm and 1 mm, for example less than or equal to about 0.25 mm. The force redirecting element 49 can be positioned along the force dampening section 44 within about 0 mm to 2 mm from the proximal end of the force dampening section 44, for example less than or equal to about 0.25 mm. The length of the distal assembly 53 distal to the force redirecting element 49 can be between 3 mm and 10 mm, for example less than or equal to about 5 mm.

Referring to FIG. 10B a force redirecting element 49 can comprise a first angular bend with and angle $\alpha 5$ and radius of curvature $RoC_5$ and a second angular bend with and angle $\alpha 6$ and radius of curvature $RoC_6$; wherein the angles $\alpha 5$ and $\alpha 6$ is between 135° and 170°, for example less than or equal to about 145°, radius of curvature $RoC_5$ and $RoC_6$ is between 0 mm and 2 mm, for example less than or equal to about 0.25 mm.

As shown in FIGS. 10C and 10D the force redirecting element 49 of the first representative embodiment can comprise one or two curves. The force redirecting element 49 can be a curved force dampening section 44.

As shown in FIG. 10D a force redirecting element 49 can comprise any pre-formed geometry that places the distal end of a catheter relative to the axis of the deflectable section 34 by a preset angle $\alpha 7$ and distance L7, wherein the preset angle $\alpha 7$ is between about 15° to 45°, for example less than or equal to about 20°, and the distance L7 is between about 1 mm and 6 mm, for example less than or equal to about 2 mm.

The force redirecting elements described above can be oriented such that the energy delivery element 24 is displaced in a direction that is in about the opposite direction and same plane as the predetermined biased flexure of the deflectable section 34. Alternatively a force redirecting element can be oriented such that the energy delivery element 24 is displaced in a direction that is in about the same direction and plane as the predetermined biased flexure of the deflectable section 34.

As shown in FIG. 16B the force redirecting element 49 is a bend in a force dampening section 44 created by a pre-formed sheath 74 over a flexible tether 104. Alternatively the force redirecting element 49 can be a bend in a force dampening section 44 made from a wire or tube with desired flexibility incorporated into the force dampening section 44 by means of material selection and dimension. For example, the force dampening section 44 can be made from Nitinol wire with a diameter of about 0.10 to 0.20 mm.

5. Force Dampening Section

As shown in FIGS. 16A to 16H, the force dampening section 44 comprises a flexible tubular structure 74. The flexible structure 74 can comprise a metal, a polymer, or a metal/polymer composite. The material and physical features of the flexible structure 74 are selected so that the force dampening section 44 has (1) sufficient flexibility to elastically deform when an energy delivery element 24 applies a pressure to an inner wall of a renal artery that is less than a pressure that is at high risk of causing trauma; but (2) sufficient stiffness to create a contact force or pressure between the energy delivery element 24 and inner wall of the renal artery that allows for energy delivery and stable contact. The flexibility of the force dampening section 44 dampens the force applied by the energy delivery element 24 to the artery wall so that the force remains in this suitable range as the deflectable section 34 is deflected over a wide range. Furthermore, by elastically deforming, a force dampening section 44 aligns an energy delivery element 24 so that its side is in contact with the artery wall as previously discussed.

The material and physical features of the flexible structure 74 could optionally be selected so that the axial stiffness and torsional stiffness of the flexible structure 74 is not greater than the axial stiffness and torsional stiffness of the third tubular structure 62. The overall flexibility of the flexible structure 74 could optionally be at least equal to or greater than the flexibility of third tubular structure 62 when the third tubular structure has not been deflected by the control wire 40.

The flexible structure 74, as a part of the force dampening section 44, can be coupled to the deflectable section as described above. Alternatively, in embodiments that do not provide a deflectable section, the force dampening section can be coupled to the first flexure zone. As shown in FIG. 16B, the energy delivery element 24 is carried at the distal end of the flexible structure 74 for placement in contact with tissue along a vessel wall of a respective renal artery.

The material selected for the flexible structure 74 can be radiopaque or non-radiopaque. For example, a radiopaque material, e.g., stainless steel, platinum, platinum iridium, or gold, can be used to enable visualization and image guidance. When using a non-radiopaque material, the material optionally may be doped with a radiopaque substance, such as barium sulfate, to facilitate visualization and image guidance.

The configuration of the flexible structure 74 can vary. For example, in the embodiment depicted in FIG. 16B, the flexible structure 74 comprises a thread 104 encased in, or covered with, a polymer coating or wrapping 110. The thread 104 is routed through a proximal anchor 108, which is attached to the distal end of the deflectable section 34, and a distal anchor 106, which is fixed within or integrated into the heating element 24/electrode 46. The distal anchor 106 may be fixed within the heating element 24/electrode 46 using, e.g., solder. Alternatively, the distal anchor 106 and heating element 24/electrode 46 may fabricated as a single piece or unitary structure.

Although various types of materials can be used to construct the aforementioned structures, in order to have a flexible structure 74 that securely connects to the deflectable section 34 and the energy delivery element 24, it is desirable for thread 104 to be comprised of a para-aramid synthetic fiber sold under the trademark KEVLAR or similar polymer thread and for the proximal anchor 108 and distal anchor 106 to be comprised of stainless steel. While the coating 110 can be comprised of any electrically insulative material, and particularly those listed later with respect to sheath 80, it is desirable for the structures of the flexible structure 74 to be encased/coated/covered by a low-durometer polymer laminate 110 such as an aliphatic, polycarbonate-based thermoplastic polyurethane sold under the trademark CARBOTHANE. As shown in FIG. 16B, one or more supply wires 29 may run alongside or within the flexible structure 74. As previously mentioned these wires may provide the energy delivery element 24 with electrical current/energy from the generator 26 and also convey data signals acquired by sensor 52. As depicted in FIG. 16B, the control wire 40 extending from the handle actuator 260 can be formed into the proximal anchor 108 and attached to the elongated shaft using solder 130.

One advantage of the above-described configuration of the flexible structure 74 is that the flexible structure 74 creates a region of electrical isolation between the energy delivery element and the rest of the elongated shaft. Both the thread 104 and laminate 110 are electrically insulative, thereby providing the supply wire(s) 29 as the sole means for electrical connectivity. Accordingly, the external surface of the flexible structure 74 and force dampening section 44 is electrically inactive.

As shown in FIGS. 16D through 16F, the flexible structure 74 allows considerable passive deflection of the force dampening section 44 when the energy delivery element 24 is put into contact with the vessel wall. As already described, this flexibility has several potential benefits. One such benefit may be the ability of the force dampening section 44 to reduce force or stress applied between the energy delivery element 24 and the vessel wall when or as the deflectable section 34 is deflected, relative to the force or stress that would be applied to the vessel wall during deflectable section 34 deflection if the force dampening section 44 were to be removed and the energy delivery element were to be coupled directly to the distal end of the deflectable section 34. This may reduce a risk of trauma. Furthermore, the force or stress applied by the energy delivery element 24 to the vessel wall may be maintained in a consistent range during deflectable section 34 deflection, particularly during movement caused by respiration and/or pulsatile flow, which may facilitate consistent and/or controlled lesion creation.

The size and configuration of the flexible structure 74 enables the energy delivery element to deflect in many directions because the force dampening section may bend by angle $\theta$ in any plane through the axis of the distal end region. For treatments within a peripheral blood vessel such as the renal artery, it is desirable that angle $\theta \leq 90$ degrees. Optionally, the flexible structure 74 is not very resilient, i.e., does not provide a significant restoring or straightening moment when deflected. For embodiments having a distal assembly 53 that comprises a force redirecting element 49, force dampening element 44 and energy delivery device 24 that are distal to a deflectable section, such as the embodiment shown in FIG. 7A, the distal assembly 53 can have a length of less than about 10 mm, for example less than about 5 mm.

The energy delivery element 24 desirably may provide omni-directional delivery of energy in substantially any or all directions. As the force dampening section 44 passively deflects at a treatment site about an angle $\theta$ appropriate to a given patient's anatomical geometry, any portion of the energy delivery element 24 may be aligned with an interior wall of the renal artery for energy delivery to target renal nerves. Blood flow may remove heat during such energy delivery, thereby reducing or mitigating a need for shielding or other preferential directing of the energy delivered to the target renal nerves that could make the force dampening section 44 undesirably stiffer or bulkier. Such omni-directional energy delivery without shielding/preferential directing may facilitate simpler or safer positioning of the energy delivery element 24 at a treatment site, as compared to shielded or directed energy delivery elements, e.g. energy delivery elements comprising a microwave or radioactive power source.

In alternative embodiments of the force dampening section 44, the flexible structure 74 can take the form of a tubular metal coil, cable, braid, polymer or metal/polymer composite, as FIG. 16H shows. Alternatively, the flexible structure 74 can take the form of an oval, or rectangular, or flattened metal coil or polymer, as FIG. 16G shows. In alternate embodiments, the flexible structure 74 may comprise other mechanical structures or systems that allow the energy delivery element 24 to pivot in at least one plane of movement. For example, the flexible structure 74 may comprise a hinge or ball/socket combination.

Candidate materials for the polymer material include polyethylene terephthalate (PET); polyethylene block amide copolymer; polyurethane; urethane; polycarbonate-based thermoplastic polyurethane; thermoplastic polyurethane; low density polyethylene (LDPE); silicone; or combinations thereof. The polymer material can be laminated, dip-coated, spray-coated, or otherwise deposited/applied over the flexible structure 74. Alternatively, a thin film of the polymer material (e.g., PTFE) can be wrapped about the flexible structure 74. Alternatively, the flexible structure 74 can be inherently insulated, and not require a separate sheath 80 or covering. For example, the flexible structure can comprise a polymer-coated coiled wire.

Figure 17A:
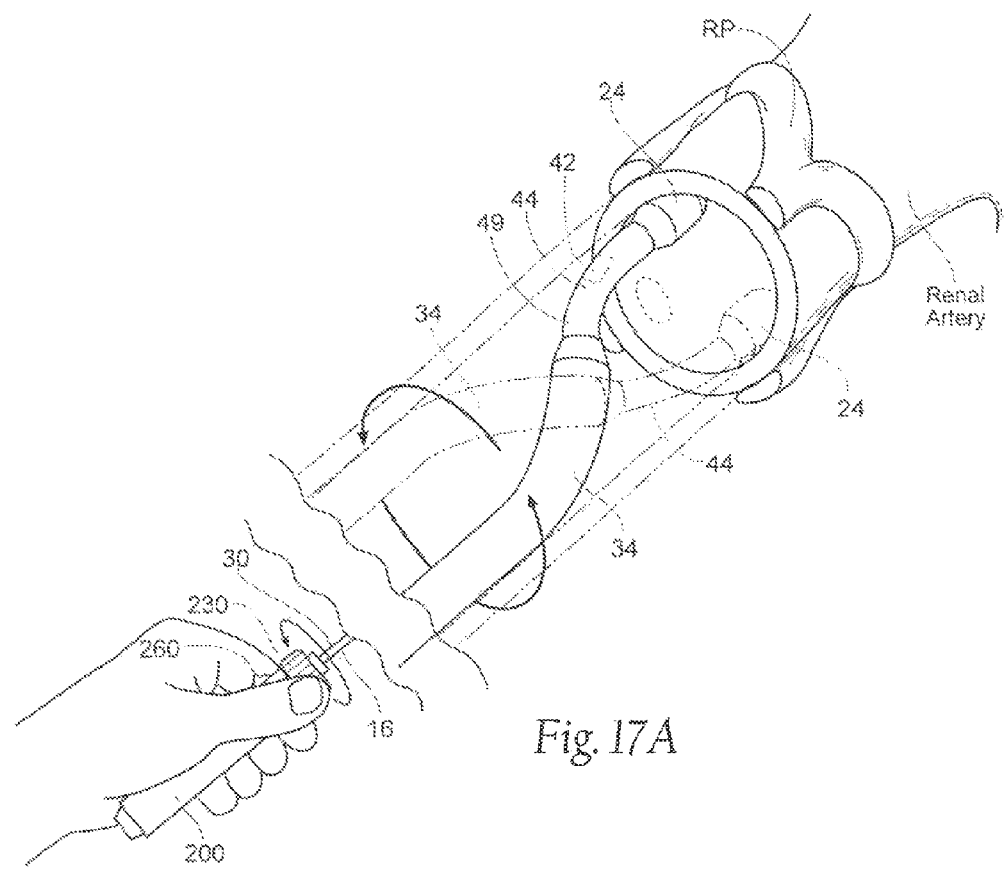
FIGS. 17A and 17B show a representative embodiment of a rotational control mechanism coupled to the handle assembly of the treatment device shown in FIG. 5.

Optionally, force dampening section 44 can include a sensor 42 that indicates an amount of deflection of force dampening section 44 as shown in FIG. 17A. The sensor 42 can be, for example, a piezo-resistive element that is a full or partial length of the force dampening section 44 and can be mounted to a side of the force dampening section. A pair of conductors (not shown) running through the elongated shaft 16 would connect the sensor 42 to an electrical supply and sensing circuit (not shown). When the force dampening section 44 is deflected in response to a force applied to the energy delivery element 24 or a portion of the force dampening section 44 by an inner wall of a renal artery, the sensor 42 will deliver a signal that quantifies the amount of deflection. When the sensor 42 is a piezo-resistive element its resistance will change proportional to its strain. The amount of deflection of force dampening section 44 is an indication of contact force with the inner wall of the renal artery.

5. Rotation Controller

Figure 17B:
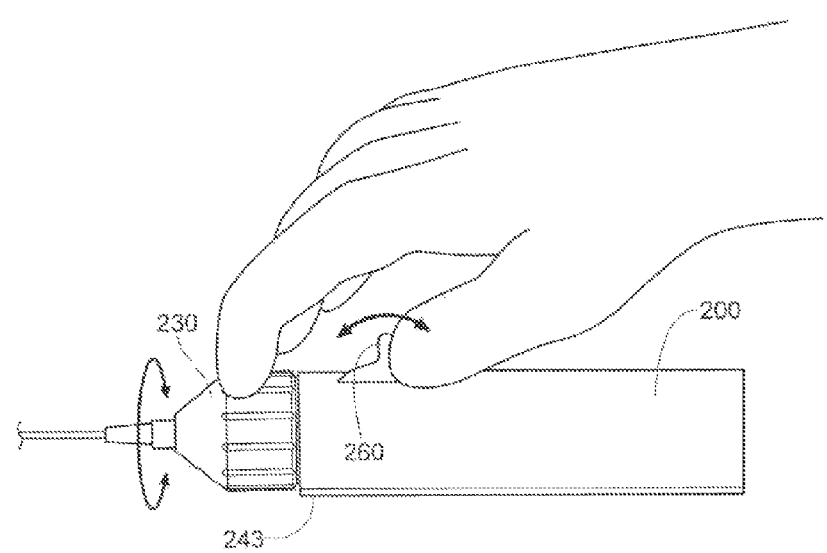
Figure 18B:
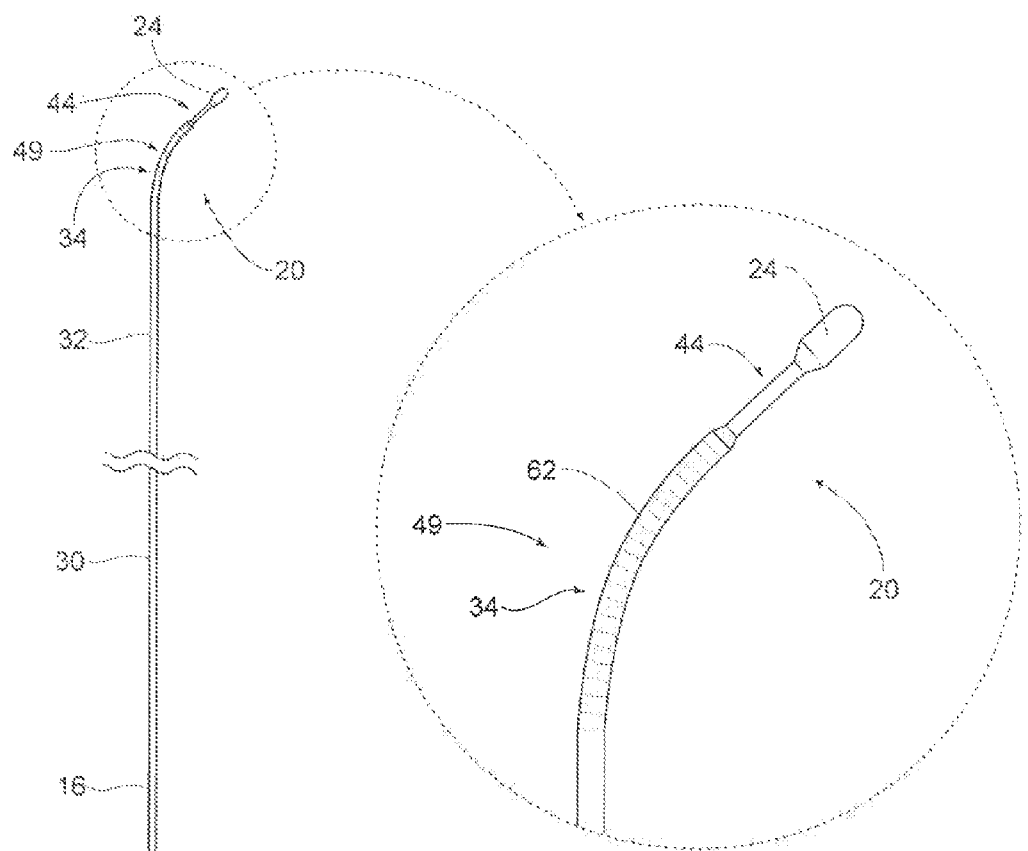
Figure 18A:
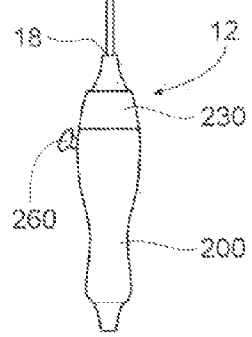

As will be discussed later in greater detail, it is desirable to rotate the device within the renal artery after the energy delivery element is in contact with the vessel wall. However, it may be cumbersome and awkward for a clinical practitioner to rotate the entire handle assembly at the proximal end of the device, particularly given the dimensions of the renal anatomy. In one representative embodiment, as shown in FIGS. 17A and 17B, the proximal end of the shaft 16 is coupled to the handle assembly 200 by a rotator 230.

The proximal end of the force transmitting section 30 is attached to a stationary coupling 88 on the rotator 230. Rotation of the rotator 230 (as FIG. 17A shows) thereby rotates the force transmitting section 30, and, with it, the entire elongated shaft 16, without rotation of the handle assembly 200. As FIG. 17A shows, a caregiver is thereby able to hold the proximal portion of the handle assembly 200 rotationally stationary in one hand and, with the same or different hand, apply a torsional force to the rotator 230 to rotate the elongated shaft 16. This allows the actuator to remain easily accessed for controlled deflection.

Since there are cables and wires running from the handle assembly through the shaft of the device (e.g., control 40, electrical transmission wire and/or sensor/thermocouple wire(s) 29, etc.), it is desirable to limit rotation of the shaft relative to these wires in order to avoid unnecessary entanglement and twisting of these wires. A rotational limiting element can be incorporated into the handle assembly and rotator to address this issue. The rotator 230 and handle assembly can be configured to allow for the optimal number of revolutions for the shaft, given such structural or dimensional constraints (e.g., wires). The components of the handle assembly may be configured, for example to allow for a finite number of revolutions of the shaft (e.g., two) independent of the handle assembly. Limiting rotation of the shaft to the optimal number of revolutions may be achieved by any number of commonly known mechanical features.

As has been described and will be described in greater detail later, by intravascular access, the caregiver can manipulate the handle assembly 200 to locate the distal end region 20 of the elongated shaft 16 within the respective renal artery. The caregiver can then operate the actuator 260 on the handle assembly 200 (see FIGS. 17A and 17B) to deflect the energy delivery element 24 about the deflectable section 34. The caregiver can then operate the rotator 230 on the handle assembly 200 (see FIGS. 17A and 17B) to apply a rotational force along the elongated shaft 16. The rotation of the elongated shaft 16 when the deflectable section 34 is deflected within the respective renal artery rotates the energy delivery element 24 within the respective renal artery, making it easier to achieve contact with the vessel wall and determine whether there is wall contact, particularly in planes where there is poor angiographic visualization.

In an additional aspect of the disclosed technology, the handle assembly 200 may be configured to minimize operator/caregiver handling of the device while it is within the patient. As shown, for example, in FIG. 17B, the handle assembly also comprises one or more surfaces 243 that substantially conform to the surface beneath (e.g., operating table). This surface 243, which is shown to be substantially flat in FIG. 17B, can alternatively be curved, shaped or angled depending on the configuration and/or geometry of the beneath surface. The conforming surface 243 enables the clinical operator to keep the handle assembly 200 stable when the treatment device 12 is within the patient. In order to rotate the device when it is inside the patient, the operator can simply dial the rotator 230 without any need to lift the handle assembly. When the operator desires to retract the device for subsequent treatments, the operator can simply slide the handle assembly along the beneath surface to the next position. Again, this mitigates the risk of injury due to operator error or over handling of the treatment device. Additionally or alternatively, the lower surface can engage the surface underneath using clips, texture, adhesive, etc.

Additional enhancements to the rotation mechanism disclosed herein include providing tactile and/or visual feedback on the rotational fitting so that the operator can exercise greater control and care in rotating the device. The rotator 230 can also be selectively locked to the handle assembly, thereby preventing further rotation, if the operator wishes to hold the treatment device in a particular angular position. Another optional enhancement includes providing distance markers along the shaft/handle assembly to enable the operator to gauge distance when retracting the treatment device.

B. Second Representative Embodiment

Deflectable Section Includes a Force Redirecting Element

FIGS. 18A-19D show representative embodiments of the second embodiment with an elongated shaft 16 that includes a force transmitting section 30, first flexure zone 32, deflectable section 34, force redirecting element 49, energy delivery element 24, and an optional force dampening section 44. In these embodiments, the materials, size, and configuration of the force transmitting section 30, first flexure zone 32, force redirecting element 49 and optional force dampening section 44 are comparable to their respective counterparts described in any of the previous embodiments.

In these embodiments, however, the deflectable section 34 may comprise a third tubular structure 62 with a force redirecting element 49 comprising a pre-formed shape or geometry that, in an unrestrained configuration, is off-axis or deflected from the longitudinal axis of the elongated shaft 16 (see, e.g., FIGS. 18A and 18B), which may facilitate locating of the energy delivery element 24 into contact with a treatment site within a renal artery. The length and diameter of deflectable section 34 may be comparable to those described in any of the previous embodiments of the deflectable section 34. In one embodiment, the pre-formed shape of the third tubular structure 62 may be specified to provide the deflectable section 34 with a desired radius of curvature $RoC_2$ and angle $\alpha 2$ (see FIG. 7C), such as those described previously. In other embodiments, the pre-formed shape can take other geometrical and dimensional forms. The third tubular structure 62 may be fabricated, for example, from a shape memory material, such as a nickel-titanium alloy (i.e., Nitinol) or from spring steel, to provide the pre-formed shape.

When advanced within, and retrieved from, a renal artery via an intravascular path, the deflectable section 34 may be positioned within a guide catheter, such as guide catheter 96, which may substantially straighten or constrain the third tubular structure 62 during such intravascular delivery and retrieval. After advancement of the deflectable section 34 distal of the guide catheter, the third tubular structure 62 may re-assume its off-axis, pre-formed shape, e.g., to bring the energy delivery element 24 into contact with a wall of the renal artery. The deflectable section 34 optionally may be actively deflected (e.g., as described previously via control wire 40 attached to handle actuator 260), in addition to the passive deflection provided by the pre-formed shape of the third tubular structure 62.

1. Active Deflection in the Direction of the Force Redirecting Element

When the deflectable section 34 is configured for both active and passive deflection, the third tubular structure 62 may be configured such that active deflection of the deflectable section is biased in the direction of the third tubular structure's pre-formed shape. This can be achieved by making the third tubular structure 62 compressible in the direction of the structure's pre-formed shape and resilient to compression opposite the structure's pre-formed shape. In such a configuration, active deflection augments or magnifies the passive deflection provided by the third tubular structure's pre-formed shape.

FIG. 18C provides a representative embodiment of a deflectable section 34 that has a pre-formed shape and that is configured for active deflection in the direction of the pre-formed shape. In FIG. 18C, the third tubular structure 62 comprises a laser-cut pattern that includes spine 66 with connecting ribs 68. The spine 66 comprises a pre-formed shape that positions the deflectable section 34 off-axis or deflected from the longitudinal axis of the elongated shaft 16 in an unrestrained configuration. The direction of the pre-formed shape is such that the laser-cut pattern biases active deflection of the third tubular structure 62, in response to pulling on the control wire 40 coupled to the distal end of the third tubular structure 62, toward the direction of the pre-formed shape. The control wire 40 is attached to a distal end of the deflectable section, for example, with solder 130.

2. Active Deflection in the Opposite Direction of the Force Redirecting Element for Bi-Directional Deflection via a Single Control Wire As an alternative to the embodiment of FIG. 18C, when the deflectable section 34 is configured for both active and passive deflection, the third tubular structure 62 may be configured such that active deflection of the deflectable section is biased in about an opposite direction of the third tubular structure's pre-formed shape. This can be achieved by making the third tubular structure 62 compressible in the opposite direction of the structure's pre-formed shape and resilient to compression in the direction of the structure's pre-formed shape. In such a configuration, active deflection reduces or reverses the passive deflection provided by the third tubular structure's pre-formed shape.

FIG. 18D provides a representative embodiment of a deflectable section 34 that has a pre-formed shape and that is configured for active deflection in the opposite direction of the pre-formed shape. In FIG. 18D, the third tubular structure 62 again comprises a laser-cut pattern that includes spine 66 with connecting ribs 68. As in the embodiment of FIG. 18C, the spine 66 comprises a pre-formed shape that positions the deflectable section 34 off-axis or deflected from the longitudinal axis of the elongated shaft 16 in an unrestrained configuration. However, in contrast to the embodiment of FIG. 18C, the direction of the pre-formed shape is such that the laser-cut pattern biases active deflection of the third tubular structure 62, in response to pulling on the control wire 40 coupled to the distal end of the third tubular structure 62, away from the direction of the pre-formed shape.

As seen in FIGS. 18E-18G, when the deflectable section 34 has a pre-formed shape and is configured for active deflection in the opposite direction of the pre-formed shape, the deflectable section desirably may achieve bi-directional bending via a single control wire 40. As seen in FIG. 18E, in the unrestrained configuration of the deflectable section 34 without active deflection (e.g., when the control wire 40 is not being pulled in tension), the deflectable section 34 assumes the pre-formed shape of its third tubular structure 62. As seen in FIG. 18F, tension applied to control wire 40 partially or completely straightens the bend in the deflectable section 34. As seen in FIG. 18G, in some embodiments additional proximal tension (i.e. via pulling/proximal retraction) of control wire 40 may deflect the deflectable section in the opposite direction of its pre-formed shape, thereby providing bi-directional bending of the deflectable section with a single control wire 40.

Optionally, the control wire 40 may be under tension, as in FIG. 18F, during delivery and/or retrieval of the energy delivery element 24 within a renal artery, in order to at least partially straighten the pre-formed shape of the deflectable section 34 during such delivery/retrieval. When positioned within the renal artery, tension may be removed from the control wire 40 to deflect the deflectable section in the direction of its pre-formed shape, as in FIG. 18E, in order to bring the energy delivery element 24 into contact with a wall of the renal artery. Additionally or alternatively, the control wire 40 may be pulled more proximally to deflect the deflectable section in the opposite direction of its pre-formed shape, as in FIG. 18G, in order to bring the energy delivery element 24 into contact with an opposing wall of the renal artery without necessitating rotation of the elongated shaft 16. As discussed previously, the force dampening section 44 desirably accommodates contact with any wall of the renal artery and passively deflects to bring the energy delivery element 24 into at least partial alignment with the contacted wall of the artery, thereby accommodating bi-directional deflection of the deflectable section 34.

3. Active Deflection in any Desired Direction in Combination with the Force Redirecting Element FIGS. 18C-18G illustrate representative embodiments of deflectable section 34 that are configured for both active and passive deflection of the deflectable section, wherein the active deflection is either in the direction of, or opposed to, the direction of passive deflection (i.e., the direction of the force redirecting element's pre-formed shape). However, it should be understood that in other contemplated embodiments active deflection of the deflectable section may be in any plane(s), as desired, and is not limited to active deflection in the direction of pre-formed shape or in the opposite direction of pre-formed shape.

4. Active Deflection Longitudinally Offset from the Force Redirecting Element

In FIGS. 18C-18G, active deflection and passive deflection of the deflectable section occur along a common longitudinal segment. Active and passive deflection alternatively/additionally may be longitudinally spaced or offset from one another. For example, the deflectable section 34 may comprise a more proximal section that is configured for active deflection and a more distal section that has a pre-formed shape, or vice versa. Active deflection may occur in the direction of the pre-formed shape, in the opposite direction of the pre-formed shape, or in any other direction, as desired.

FIG. 19A illustrates a representative embodiment of a deflectable section 34 with a more proximal section configured for active deflection and a more distal section that has a pre-formed shape. The more proximal section of the deflectable section 34 illustratively is configured for active deflection in the opposite direction of the more distal section's pre-formed shape. However, it should be understood that the pre-formed shape alternatively may be directed in the direction of active deflection or in any other direction.

As seen in FIG. 19A, the third tubular structure 62 comprises a laser-cut pattern that includes spine 66 with connecting ribs 68. In contrast to the embodiments of FIGS. 18A-18G, solder 130 connects control wire 40 to the third tubular structure 62 proximal of the deflectable section's distal end, e.g., at the distal end of a more proximal section of the third tubular structure 62 and/or at the proximal end of a more distal section of the third tubular structure. Distal of the attachment of control wire 40 to the third tubular structure 62, spine 66 comprises a force redirecting element 49, which comprises a pre-formed, off-axis shape. The third tubular structure's laser-cut pattern biases active deflection of the third tubular structure 62, in response to pulling on the control wire 40 coupled to the third tubular structure 62 proximal of the spine's pre-formed shape, in the opposite direction of the pre-formed shape.

With reference now to FIGS. 19B-19D, when the deflectable section 34 has a more proximal section configured for active deflection in an opposite direction of a more distal section's pre-formed shape, the deflectable section 34 desirably may promote buckling in the first flexure zone 32 or deflectable section 34 with reduced contact force applied to the vessel wall by the energy delivery element 24 which may provide a more atraumatic navigation. Additionally/alternatively, such a deflectable section may facilitate the establishment of contact and treatment at angularly opposed luminal surfaces of the renal artery without necessitating rotation of elongated shaft 16.

As seen in FIG. 19B, in the unrestrained configuration of the deflectable section 34 without active deflection (e.g., when the control wire 40 is not being pulled in tension), the more distal section of the deflectable section 34 assumes the pre-formed shape of its third tubular structure 62. As discussed previously, when positioned within a renal artery, the first flexure zone 32 may lie along or near a superior wall surface of the renal artery (see, for example, FIG. 14A). As seen in FIG. 19C, when not actively deflected, the pre-formed shape of the more distal section of the deflectable section may urge energy delivery element 24 and optional force dampening section 44 into contact with that superior wall surface. Previously described passive deflection of the optional force dampening section may at least partially align the energy delivery element 24 with the superior wall surface, as shown.

As seen in FIG. 19D, tension applied to control wire 40 deflects the more proximal section of the deflectable section 34 in the opposite direction of the more distal pre-formed shape, e.g., toward an inferior surface of the renal artery. The pre-formed shape may cause the energy delivery element 24 to contact the inferior surface at a lower contact angle (i.e., at an angle less than perpendicular to the surface) than it otherwise would without the pre-formed shape. Previously described passive deflection of the optional force dampening section may at least partially align the energy delivery element 24 with the inferior wall surface, as shown. FIGS. 19C and 19D illustrate establishment of contact and treatment at angularly opposed luminal surfaces of the renal artery without necessitating rotation of elongated shaft 16.

C. Third Representative Embodiment

Deflectable Section Facilitates Controlled, Multi-Directional Deflection

FIGS. 20A-20D show representative embodiments of the third embodiment having an elongated shaft 16 that includes a force transmitting section 30, a first flexure zone 32, a deflectable section 34, a force redirecting element 49, energy delivery element 24 and an optional force dampening section 44 (see FIG. 20A). In these embodiments, the materials, size, and configuration of the force transmitting section 30, first flexure zone 32, and optional force dampening section 44 are comparable to their respective counterparts described in any of the previous embodiments. Furthermore, the length and diameter of deflectable section 34 in the embodiments of FIG. 20 may be comparable to those described in any of the previous embodiments of the deflectable section 34. Also, controlled bending of the deflectable section 34 may provide the deflectable section with a desired radius of curvature $RoC_2$ and angle $\alpha 2$ (see FIG. 7C), such as those described previously.

However, in the third embodiment of the present invention, the deflectable section 34 may facilitate controlled deflection in multiple different directions, e.g., may comprise multiple control wires 40 for controllably deflecting the deflectable section in multiple different directions. Controlled, multi-directional bending of the deflectable section may facilitate placement of energy delivery element 24 into stable contact with a treatment site or with multiple treatment sites within a renal artery. Such control over placement of the energy delivery element may be especially useful in patients with relatively tortuous vessels. For example, if placement of the energy delivery element 24 into contact with a renal arterial treatment site is sub-optimal under controlled bending of the deflectable section in a first direction, the deflectable section may be controllably deflected in a second direction to more optimally place the energy delivery element into contact with the treatment site, or with an alternative or additional treatment site. Furthermore, stable contact and energy delivery may be achievable at multiple treatment sites via controlled multi-directional deflection of the deflectable section.

In some representative embodiments of the third embodiment, the deflectable section may comprise a centrally positioned spine coupled to ribs or surrounded by a coil; the centrally positioned spine may possess a geometry that facilitates controlled, multi-directional bending.

FIGS. 20B-20D provide representative embodiments of the third embodiment with a deflectable section 34 configured for controlled, multi-directional bending having a central spine and multiple control wires.

In the embodiment of FIGS. 20B and 20C, the deflectable section is configured for controlled, bi-directional bending. As seen in the cross-section of FIG. 16B, the third tubular structure 62 of the deflectable section 34 comprises a centrally positioned spine 66 having a substantially flat or ribbon shape (i.e., the spine's width is significantly greater than its thickness) that substantially divides the third tubular structure in half. A central lumen of diameter less than the spine's depth may be formed through the center of the spine 66 for passage of electrical transmission wire(s) and/or sensor/thermocouple wire(s) 29.

Third tubular structure 62 may be fabricated, for example, via Electrical Discharge Machining (EDM), micromachining and/or extrusion, to form a tube with a ribbon having a lumen, wherein the ribbon bisects the tube, as in FIG. 20B. As seen in FIG. 20C, a laser-cut pattern then may remove sections of the tube along its length to form connecting ribs 68a and 68b at spaced intervals along the tube's length that extend on opposing sides of spine 66 about the circumference of the third tubular structure 62. Control wires 40a and 40b are attached to a distal end of the deflectable section 34 with solder 130 on opposing sides of spine 66 and travel along the length of the third tubular structure radially positioned between the spine 66 and the ribs 68.

Alternatively, the deflectable section 34 may comprise a centrally positioned spine 66 that is resilient to compression and is surrounded by a third tubular structure 62. The third tubular structure is compressible and may comprise a laser-cut hypo tube, a hollow coil with a loose pitch, a hollow cable, a braided shaft, etc. The spine may be connected to the third tubular structure 62 along its length, may be connected to the structure at only one or a few locations (e.g., at its distal end), or may float or be friction fit within the coiling third tubular structure.

The geometry of spine 66, in combination with the geometry of ribs 68a and 68b and the distal attachment locations of control wires 40a and 40b, facilitate controlled, bi-directional bending of the deflectable section 34, e.g., by substantially constraining bending of the spine 66 in response to pulling of a wire 40a or 40b to planes perpendicular to the width of the spine. The deflectable section deflects in a first direction in response to pulling on the control wire 40a while the control wire 40b is not under significant tension (see FIG. 20C). The deflectable section deflects in a second, opposing direction in response to pulling on the control wire 40b while the control wire 40a is not under significant tension.

While FIGS. 20B and 20C illustrate a bi-directional bending embodiment of the deflectable section 34, the third tubular structure 62 may be fabricated with a centrally positioned spine that facilitates bending in any number of directions, as desired. FIG. 20D illustrates an embodiment of a deflectable section with a centrally positioned spine that is configured for controlled, quad-directional deflection. As seen in FIG. 20D, the third tubular structure 62 comprises centrally positioned spines 66a and 66b whose widths are angularly offset from one another by about 90° in an alternating pattern along the length of the third tubular structure. A centrally-positioned lumen extends through the ribbon sections along the length of the third tubular structure for passage of electrical transmission wire(s) and/or sensor/thermocouple wire(s) 29. Between each pair of the spinal ribbon sections 66a and 66b, the spine 66 forms a spinal ribbon connector section 66c that connects the pair of spinal ribbon sections.

Third tubular structure 62 thus comprises a series of repeating segments along the length of the structure. Each repeating segment has a first connector section 66c; followed lengthwise by a ribbon section 66a; followed lengthwise by a second connector section 66c; followed lengthwise by a ribbon section 66b that is 90° angularly offset from the width of ribbon section 66a; followed lengthwise by a repeating first connector section 66c; etc. The third tubular structure 62 of FIG. 20D may, for example, be fabricated from a combination of EDM, micromachining and/or extrusion, as well laser cutting.

Control wires 40a, 40b, 40c or 40d are positioned within lumens that extend through each ribbon section 66a and 66b near either end of the width of each ribbon section (i.e., four such lumens in all, in addition to the centrally-positioned lumen for passage of wire 29). Control wires 40a, 40b, 40c, and 40d may be routed through these lumens along the length of the third tubular structure and are attached to a distal end of the deflectable section with solder 130. Pulling on any one of the control wires while the other three control wires are not under significant tension may provide controlled deflection of the deflectable section 34 in the direction of the wire being pulled. In this manner, the deflectable section 34 may be configured for controlled, quad-directional bending in four directions that are about 90° angularly offset or out of phase from one another.

FIGS. 20B and 20C illustrate a deflectable section 34 with a centrally positioned spine 66 configured for bi-directional controlled deflection, while FIG. 20D illustrates a deflectable section 34 with a centrally positioned spine 66 configured for quad-directional controlled deflection. The deflectable section alternatively may comprise a centrally positioned spine 66 configured for deflection in any number of additional directions, as desired. For example, additional ribbon sections may be provided at additional angular offsets and connected by spinal connector sections having additional sides. When combined with appropriate ribs 68 and control wires 40, controlled deflection in any number of directions may be achieved.

D. Fourth Representative Embodiment

Deflectable Section Configured for Deflection at a Joint

Figure 21A:
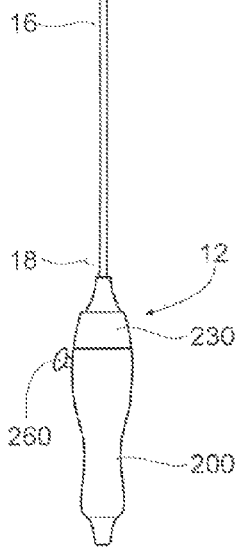
FIGS. 21A to 21C show additional alternative representative embodiments of an elongated shaft for a treatment device like that shown in FIG. 5, showing examples of the different structural, mechanical and functional regions that the elongated shaft can incorporate.
Figure 21B:
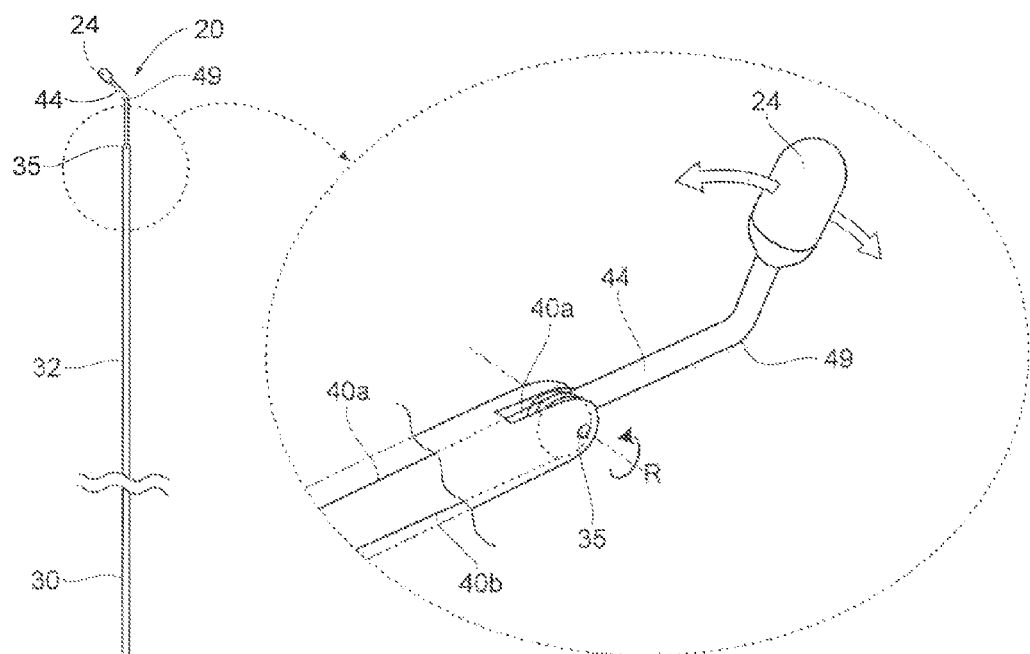
Figure 21C:
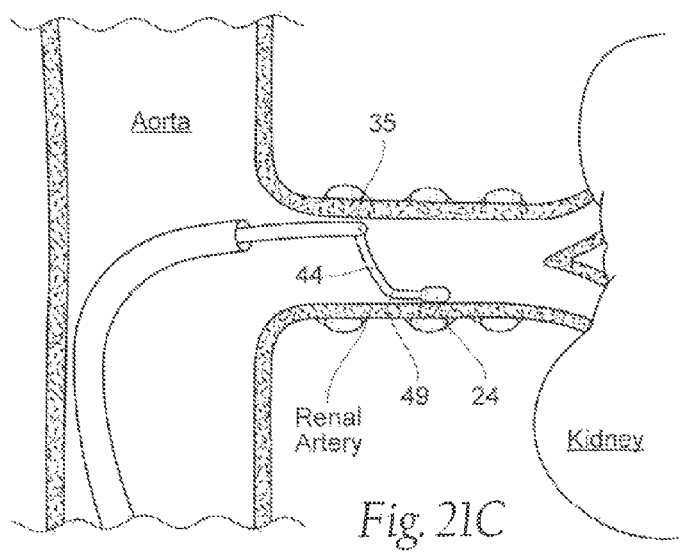

FIGS. 21A-21C show representative embodiments of the fourth embodiment having an elongated shaft 16 that includes a force transmitting section 30, a first flexure zone 32, a deflectable section that comprises a joint 35, and a force dampening section 44 comprising a force redirecting element 49 (see FIG. 21A). In these embodiments, the materials, size, and configuration of the force transmitting section 30, first flexure zone 32, force dampening section 44, and force redirecting element 49 are comparable to their respective counterparts described in any of the previous embodiments.

However, in the fourth embodiment of the present invention, the deflectable section 34 is replaced by one or more joints 35 to facilitate deflection of the force dampening section 44. Joints 35 may provide precise deflection control, as the joints may exhibit consistent deflection dynamics. Furthermore, joints may provide a sharper bend than would be achievable with some of the previously described embodiments of the deflectable section since a joint represents a pivot point as opposed to a Radius of Curvature. Thus, the length of a jointed deflectable section may be less than the length of a previously described biased spine deflectable section. This may facilitate thermal neuromodulation in shorter renal arteries, and/or may facilitate use of a longer force dampening section 44 as shown in FIG. 21C. A longer force dampening section may dissipate vessel contact force over its longer length and resiliently apply pressure to the vessel wall to provide stable electrode contact during pulsatile blood flow and respiratory motion. Also, a longer force dampening section may be easier to visualize with fluoroscopy. The force dampening section 44 may be between about 6 mm and 16 mm long, for example about less than or equal to 9.5 mm, which could be suitable to provide sufficient flexure in renal arteries.

With reference to FIG. 21B, in one representative embodiment of the fourth embodiment, hinge joint 35 connects the first flexure zone 32 to the force dampening section 44. Control wires 40a and 40b are attached to either side of the joint 35 distal to the Axis of Rotation R for rotating the force dampening section 44 about the Axis of Rotation R of the hinge joint. Alternatively, one control wire is attached to a side of a joint 35 distal to the Axis of Rotation R for rotating the force dampening section 44 about the Axis of Rotation R of the hinge joint and a spring rotates the force dampening section 44 back to its undeflected state when tension in the control wire is relieved.

Force dampening section 44 comprises, along its longitudinal length, a force redirecting element 49, which distances the energy delivery element 24 from the axis of the force dampening section 44 at a similar angle and distance as described in earlier embodiments. Since the slenderness ratio (length:diameter) is greater for a longer force dampening section 44, a longer force dampening section 44 is more susceptible to buckling especially when a load applied is distanced from its axis. As the distal assembly 53 is advanced into a renal artery and the energy delivery element 24 contacts a renal artery wall, the load applied to the energy delivery element 24 is distanced from the axis of the force dampening section 44 and could cause the force dampening section 44 to buckle at a load that is lower than a traumatic load. A force redirecting element 49 can be located on the force dampening section 44 longitudinally at about the midpoint. For example, on a 9.5 mm long force dampening section 44 the force redirecting element 49 can be about 4 to 5 mm proximal to the distal end.

E. Fifth Representative Embodiment the Force Redirecting Element is Configured to Facilitate Multi-Directional Access FIGS. 22A-22G show representative embodiments of the fifth embodiment having an elongated shaft 16 that includes a force transmitting section 30, a first flexure zone 32, and a force dampening section 44 comprising a force redirecting element. In these embodiments, the materials, size, and configuration of the force transmitting section 30, first flexure zone 32, force dampening section 44, force redirecting elements 49, and energy delivery element 24 are comparable to their respective counterparts described in any of the previous embodiments.

However, in the fifth representative embodiment the force dampening section 44 and force redirecting element 49 are configured to deflect the energy delivery element 24 in multiple directions so that the energy delivery element 24 can be placed in contact with an inner wall of a renal artery at various locations. In such embodiments, the force redirecting element 49 comprises multiple (i.e., more than one) bends. For example, as shown in FIG. 22D, bends 49' and 49" are spaced apart along the axis of the catheter. The fifth embodiment is configured to be advanced into a renal artery while retracted in a delivery sheath 95. When the distal assembly is retracted in the delivery sheath the force dampening section 44 and force redirecting element 49 flexibly conform to the delivery sheath (see FIG. 22B). When the distal assembly is advanced to a desired depth in a renal artery the delivery sheath is pulled back to expose a first bend 49' of the force redirecting element 49 which elastically deforms to deflect the force dampening section 44 a first angle $\alpha 8$, distancing and energy delivery element 24 from the axis of the elongated tubular body 16 in a first direction (see FIG. 22C). When the delivery sheath is pulled back further to expose a second bend 49" the second bend elastically deforms deflecting the force dampening section 44 a second angle $\alpha 9$, distancing the energy delivery element 24 from the axis of the elongated tubular body 16 in a second direction (see FIG. 22D).

The force redirecting element 49 can be configured with multiple angles $\alpha 8$ and $\alpha 9$ as shown in FIG. 22A such that when deployed in a renal artery an energy delivery element 24 is placed in contact with an inner wall of a renal artery in multiple directions dependant on the portion of the force redirecting element 49 that protrudes from a delivery sheath as shown in FIGS. 22E and 22F. The angles $\alpha 8$ and $\alpha 9$ can be greater than 90° and less than 180° and such that a first angle $\alpha 8$ minus a second angle $\alpha 9$ is greater than 0° and less than 90°, for example first angle $\alpha 8$ can be between about 130° and 150°, for example less than or equal to 140°, and second angle $\alpha 9$ can be between about 90° and 130°, for example less than or equal to about 110°. The length of the force dampening section 44 and position of the force redirecting element 49 are configured so that the energy delivery element 24 is placed in contact with an inner wall of a renal artery with stable contact force. For example, the length from the distal end of an energy delivery element 24, including the force dampening section 44 to the first bend 49' can be about 8 mm to 11 mm (e.g. less than or equal to 9.5 mm); the first angle $\alpha 8$ can be about 130° to 150° (e.g. less than or equal to 140°); the length between the first and second angle can be about 1.25 mm to 3 mm (e.g. less than or equal to 1.5 mm); and the second angle $\alpha 9$ can be about 90° to 130° (e.g. less than or equal to) 110°).

Alternatively, force redirecting element 49 can be configured with a gradual curve such as a helical shape as shown in FIG. 22G such the force dampening section 44 is deflected in multiple three dimensional directions, depending on the proportion of force redirecting element 49 that is protruded from a delivery sheath. The force redirecting element 49 in combination with the force dampening section 44 are configured such that as the force redirecting element 49 is advanced from a delivery sheath in its flexibly conformed retracted state it elastically deforms to place an energy delivery element 24, mounted on a distal end of the force dampening section 44, in contact with an inner wall of a renal artery. For example, the force redirecting element 49 can comprise a helical structure with a helical angle between about 20° and 50° (e.g. less than or equal to 30°); a diameter of about 2 mm to 4 mm (e.g. less than or equal to 3 mm); and about 0.5 to 3 turns (e.g. less than or equal to 1 turn); and the force redirecting element 49 can be positioned about 7 mm to 11 mm (e.g. less than or equal to 9.5 mm) from the distal end of the energy delivery element 24.

F. Sixth Representative Embodiment

The Length of the Force Dampening Section can be Telescopically Adjusted

FIGS. 23A-23D show representative embodiments of the sixth embodiment having an elongated shaft 16 that includes a force transmitting section 30, a first flexure zone 32, a force redirecting element 49, and a force dampening section 44. In these embodiments, the materials, size, and configuration of the force transmitting section 30, first flexure zone 32, force redirecting element 49, force dampening section 44, and energy delivery element 24, are comparable to their respective counterparts described in any of the previous embodiments.

However, in the sixth representative embodiment the force redirecting element 49 is connected to a first flexure zone 32 and the force dampening section 44 comprises an elongated flexible wire or tube that is slidably contained in a lumen 17 passing through the force redirecting element 49 and elongated tubular body 16 such that the force dampening section 44 can be telescopically distanced from the distal opening of the lumen 17 by advancing the proximal end of the force dampening section 44 through the lumen 17. As with previous embodiments the force redirecting element 49 is configured to flexibly conform to the inner lumen of a guide catheter and elastically deflect to a predetermined angle when not constrained by the guide catheter. The force redirecting element 49 comprises an angle as discussed earlier that distances the energy delivery element 24 from the axis of the elongated tubular body 16 such that as the catheter is advanced along an axial trajectory and a force is applied to the energy delivery element 24 by a contacting inner artery wall, the force dampening section 44 and elongated tubular body are persuaded to buckle and the trajectory is modified to flow through an artery. The telescopically adjustable length of the force dampening section 44 can be shortened while the distal assembly 53 is being advanced through a renal artery. When the distal assembly is advanced to a desired distance in a renal artery the force dampening section 44 can be telescopically lengthened to facilitate contact between the energy delivery element 24 and an inner wall of the renal artery.

The force redirecting element 49 can deflect the force dampening section 44 at angle similar to an angle in previous embodiments (such as angle α4 shown in FIG. 7B). For example, the angle of the force redirecting element 49 can be between about 130° and 170° (e.g. less than or equal to 160°). The minimum length of the force dampening section 44 protruding distal from the bend of the force redirecting element 49 can also be similar to the length L4 of a force dampening section 44 in previous embodiments (as shown in FIG. 7A). For example, the minimum protruding length of the force dampening section 44 can be between about 2 mm and 5 mm. The length of the force dampening section 44 protruding from the distal opening of the lumen 17 can be telescopically increased to a maximum of between about 5 mm to 30 mm (e.g. less than or equal to 20 mm). Alternatively, a combination of the angle α4 and length of the telescopically protruding force dampening section 44 can distance an energy delivery element 24 from the axis of the elongated tubular body 16 by a distance of between about 1 mm and 15 mm.

As shown in FIG. 23D force dampening section 44 can further comprise a second force redirecting element 49' that distances the distal tip of the energy delivery element 24 from the axis of the force dampening section 44 such that as the force dampening section 44 is telescopically advanced, a load created by contact with the artery is distanced from the axis of the force dampening section 44 promoting buckling of the force dampening section 44.

Force dampening section 44 can be comprised, for example, of a electrically insulated Nitinol wire and conducting wires that carry energy and sensor signals to and from the energy delivery element 24 and the generator 26 can be held in the space between the electrical insulation and the Nitinol wire. The proximal end of the force dampening section 44 can extend through a lumen to a proximal opening in the lumen of the elongated tubular body where it can be manipulated to telescopically lengthen the distal portion of the force dampening section 44 that protrudes from the distal opening of the lumen 17. Alternatively, the proximal end of the force dampening section 44 can be manipulated by an actuator 260 in a handle 200.

IV. Use of the System

A. Intravascular Delivery, Deflection and Placement of the Treatment Device Any one of the embodiments of the treatment devices 12 described herein can be delivered over a guide wire using conventional over-the-wire techniques. When delivered in this manner (not shown), the elongated shaft 16 includes a passage or lumen accommodating passage of a guide wire.

Alternatively, any one of the treatment devices 12 described herein can be deployed using a conventional guide catheter or pre-curved renal guide catheter 94.

When using a guide catheter 94 (see FIG. 6A), the femoral artery is exposed and cannulated at the base of the femoral triangle, using conventional techniques. In one exemplary approach, a guide wire (not shown) is inserted through the access site and passed using image guidance through the femoral artery, into the iliac artery and aorta, and into either the left or right renal artery. A guide catheter can be passed over the guide wire into the accessed renal artery. The guide wire is then removed. Alternatively, a renal guide catheter (shown in FIG. 24A), which is specifically shaped and configured to access a renal artery, can be used to avoid using a guide wire. Still alternatively, the treatment device can be routed from the femoral artery to the renal artery using angiographic guidance and without the need of a guide catheter.

When a guide catheter is used, at least three delivery approaches can be implemented. In one exemplary approach, one or more of the aforementioned delivery techniques can be used to position a guide catheter within the renal artery just distal to the entrance of the renal artery. The treatment device is then routed via the guide catheter into the renal artery. Once the treatment device is properly positioned within the renal artery, the guide catheter is retracted from the renal artery into the abdominal aorta. In this approach, the guide catheter should be sized and configured to accommodate passage of the treatment device. For example, a 6 French guide catheter can be used.

In a second exemplary approach, a first guide catheter is placed at the entrance of the renal artery (with or without a guide wire). A second guide catheter is passed via the first guide catheter (with or without the assistance of a guide wire) into the renal artery. The treatment device is then routed via the second guide catheter into the renal artery. Once the treatment device is properly positioned within the renal artery the second guide catheter is retracted, leaving the first guide catheter at the entrance to the renal artery. In this approach the first and second guide catheters should be sized and configured to accommodate passage of the second guide catheter within the first guide catheter (i.e., the inner diameter of the first guide catheter should be greater than the outer diameter of the second guide catheter). For example, the first guide catheter could be 8 French in size and the second guide catheter could be 5 French in size.

In a third exemplary approach, and as shown in FIG. 24A, a renal guide catheter 94 is positioned within the abdominal aorta, just proximal to the entrance of the renal artery. As now shown in FIG. 24B, the treatment device 12 as described herein is passed through the guide catheter 94 and into the accessed renal artery. The elongated shaft makes atraumatic passage through the guide catheter 94, in response to forces applied to the force transmitting section 30 through the handle assembly 200. The first flexure zone 32 accommodates significant flexure at the junction of the left/right renal arteries and aorta to gain entry into the respective left or right renal artery through the guide catheter 94 (as FIG. 24B shows).

As FIG. 24C shows, the deflectable section 34 on the distal end portion of the elongated shaft 16 can now be axially translated into the respective renal artery, remotely deflected (illustratively, planar deflection or bending, but alternatively any other previously described deflection may be provided) and/or rotated in a controlled fashion within the respective renal artery to attain proximity to and a desired alignment with an interior wall of the respective renal artery. As FIG. 24C further shows, the optional force dampening section 44 bends to place the thermal energy heating element 24 into contact with tissue on the interior wall (alternatively or additionally, one or more energy delivery elements 24 may positioned along the length of the deflectable section 34 and brought into contact with tissue on the interior wall during remote deflection of the deflectable section).

B. Creation of Thermally Affected Tissue Regions

As previously described (and as FIG. 24B shows), the energy delivery element 24 can be positioned by bending along the first flexure zone 32 at a first desired axial location within the respective renal artery. As FIG. 24C shows, the energy delivery element 24 can be radially positioned by deflection of deflectable section 34 toward the vessel wall. As FIG. 24C also shows, the energy delivery element 24 can be placed into a condition of optimal surface area contact with the vessel wall by further deflection of the force dampening section 44.

Once the energy delivery element 24 is positioned in the desired location by a combination of deflection of the deflectable section 34, deflection of the force dampening section 44 and/or rotation of the catheter, treatment can be administered. Optionally, infusate, such as saline, may be delivered (e.g., may be infused through the energy delivery element) in the vicinity of the treatment site before, during and/or after treatment to provide conductive and/or convective cooling in excess of that provided by blood flow. By applying energy through the energy delivery element 24, a first thermally affected tissue region 98(a) can be formed, as FIG. 24D shows. In the illustrated embodiment, the thermally affected region 98(a) takes the form of a lesion on the vessel wall of the respective renal artery.

After forming the first thermally affected tissue region 98(a), the catheter optionally may be repositioned for another thermal treatment. As described above in greater detail, it is desirable to create multiple focal lesions that are circumferentially spaced along the longitudinal axis of the renal artery. To achieve this result, the catheter optionally may be retracted and, optionally, rotated to position the energy delivery element proximally along the longitudinal axis of the blood vessel. Rotation of the elongated shaft 16 from outside the access site (see FIG. 24E) may circumferentially reposition the energy delivery element 24 about the renal artery. Once the energy delivery element 24 is positioned at a second axial and circumferential location within the renal artery spaced from the first-described axial position, as shown in FIG. 24E (e.g., 98(b)), another focal treatment can be administered treatment (with or without saline infusion). By repeating the manipulative steps just described (as shown in FIGS. 24F through 24K), the caregiver can create several thermally affected tissue regions 98(a), 98(b), 98(c) and 98(d) on the vessel wall that are axially and circumferentially spaced apart, with the first thermally affected tissue region 98(a) being the most distal and the subsequent thermally affected tissue regions being more proximal. FIG. 24I provides a cross-sectional view of the lesions formed in several layers of the treated renal artery. This figure shows that several circumferentially and axially spaced-apart treatments (e.g., 98(a)-98(d)) can provide substantial circumferential coverage and, accordingly, cause a neuromodulatory effect to the renal plexus. Clinical investigation indicates that each lesion will cover approximately 30 percent of the circumferential area surrounding the renal artery. In other embodiments, the circumferential coverage of each lesion can be as much as 60 percent.

In an alternative treatment approach, the treatment device can be administered to create a complex pattern/array of thermally affected tissue regions along the vessel wall of the renal artery. As FIG. 24L shows, this alternative treatment approach provides for multiple circumferential treatments at each axial site (e.g., 98, 99 and 101) along the renal artery. Increasing the density of thermally affected tissue regions along the vessel wall of the renal artery using this approach might increase the probability of thermally-blocking the neural fibers within the renal plexus.

Figure 24G:
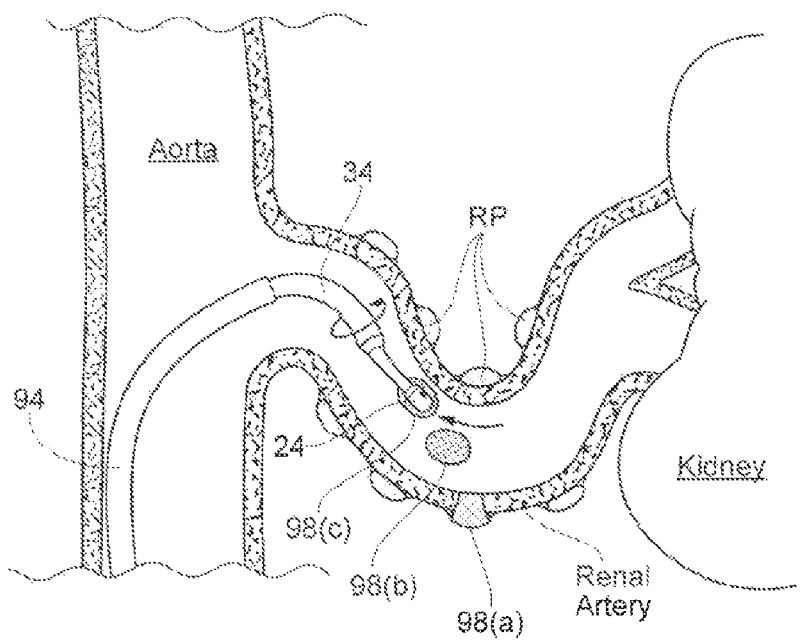
Figure 24H:
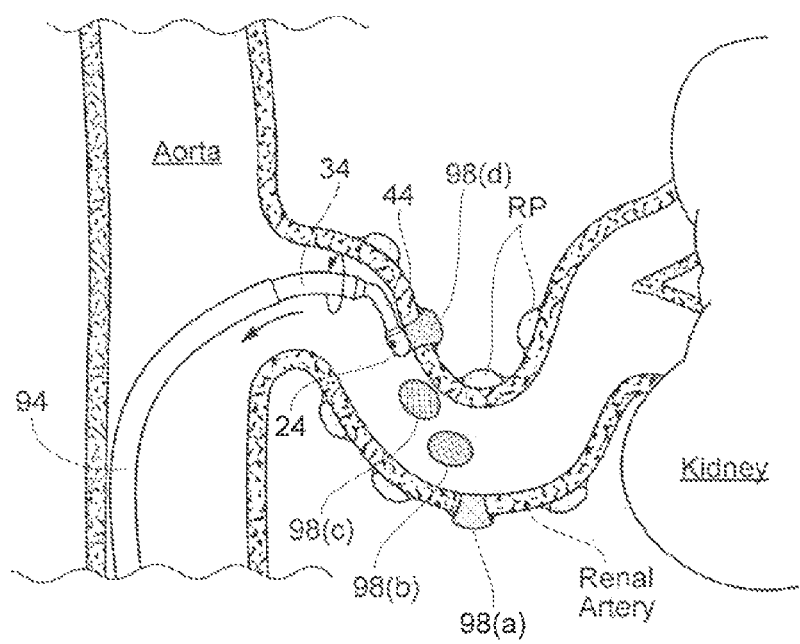
Figure 24I:
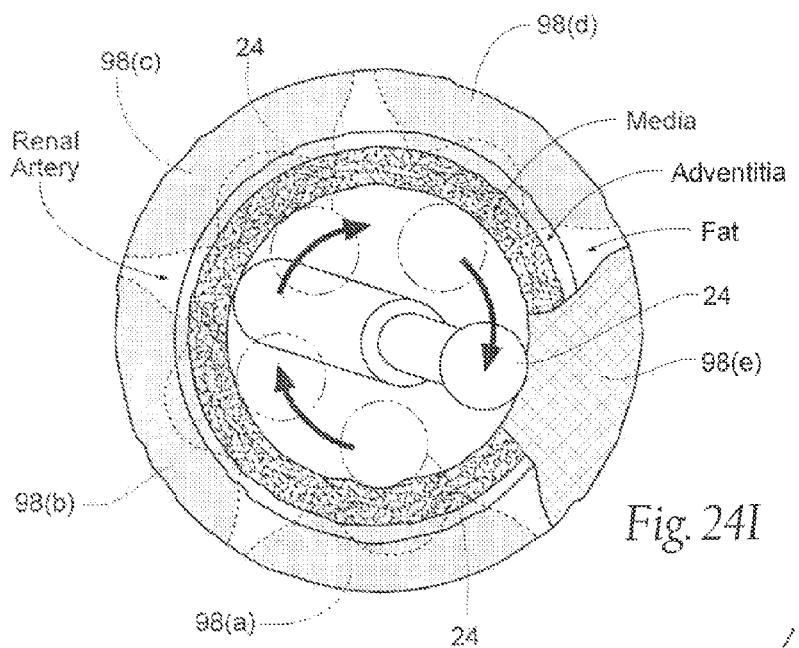
FIGS. 24I to 24K show the circumferential treatment effect resulting from intravascular use of a treatment device, like that shown in FIG. 5.
Figure 24J:
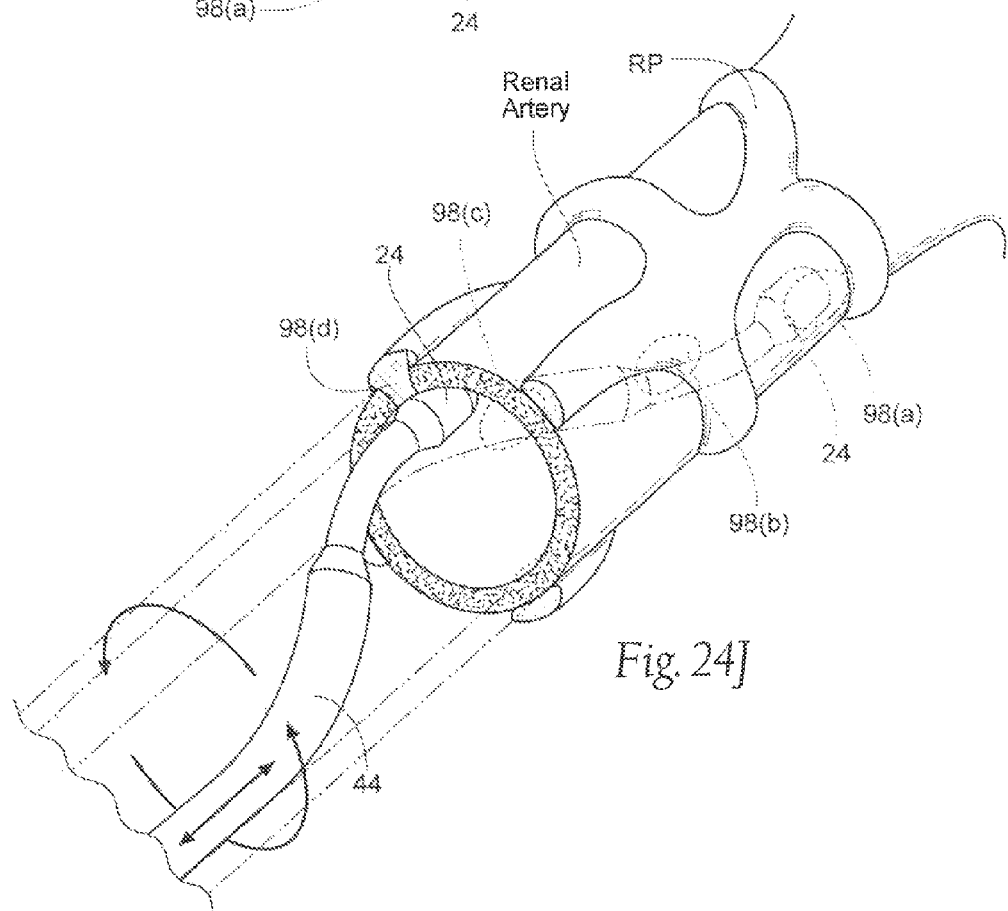
Figure 24K:
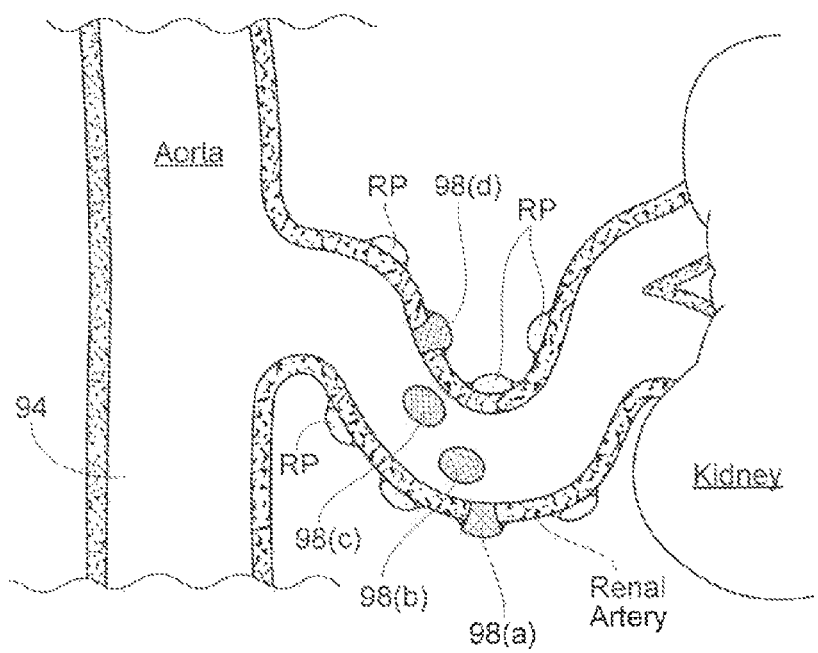
Figure 24L:
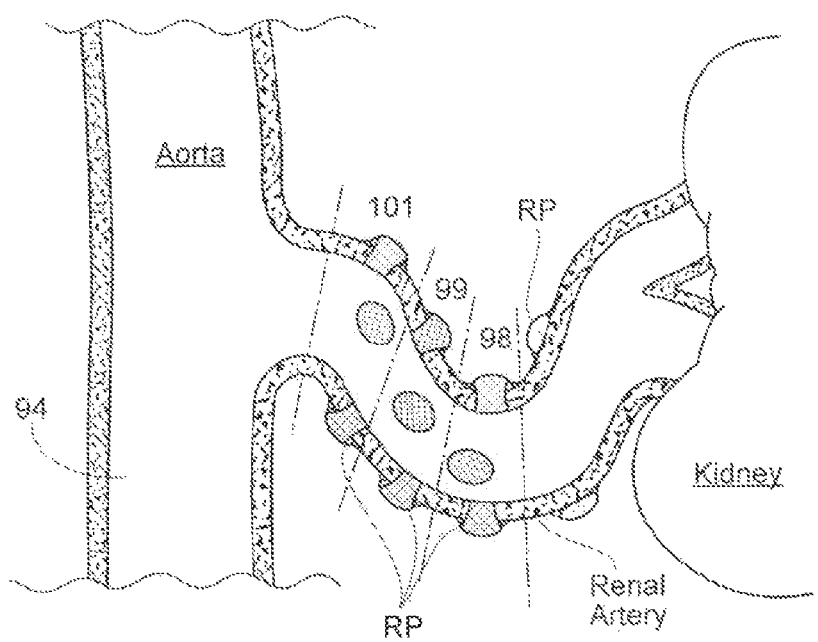
FIG. 24L shows an alternative intravascular treatment approach using a treatment device, like that shown in FIG. 5.

The rotation of the energy delivery element 24 within the renal artery as shown in FIG. 24G may improve the reliability and consistency of the treatment. Since angiographic guidance such as fluoroscopy only provides visualization in two dimensions, it is generally only possible in the anterior/posterior view to obtain visual confirmation of wall contact at the superior (vertex) and inferior (bottom) of the renal artery. For anterior and posterior treatments, it may be desirable to first obtain confirmation of contact at a superior or inferior location and then rotate the catheter such that the energy delivery element travels circumferentially along the vessel wall until the desired treatment location is reached. Physiologic data such as impedance can be concurrently monitored to ensure that wall contact is maintained or optimized during catheter rotation. Alternatively, the C-arm of the fluoroscope can be rotated to achieve a better angle for determining wall contact.

FIG. 24 illustrate multiple longitudinally and circumferentially spaced focal lesions that are created by repositioning energy delivery element 24 through a combination of deflectable section deflection, and elongated shaft rotation and/or translation. In some of the previously described embodiments of the treatment device, such multiple focal lesions may be created with multiple energy delivery elements 24 positioned along the length of the distal end region 20. Additionally or alternatively, in some of the previously described embodiments of the treatment device, such multiple focal lesions may be created by repositioning energy delivery element(s) 24 solely through deflectable section deflection in multiple planes, solely through elongated shaft translation, solely through elongated shaft rotation, or solely through any subset of deflectable section deflection, elongated shaft translation and elongated shaft rotation.

Figure 27A:
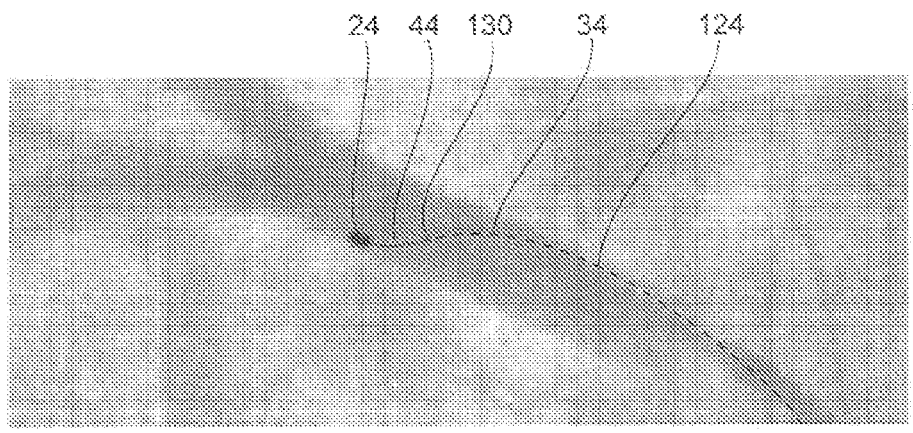
FIGS. 27A to 27C show fluoroscopic images of a treatment device, like that shown in FIG. 5 but without a force redirecting element, in multiple treatment positions within a renal artery of an animal.
Figure 27B:
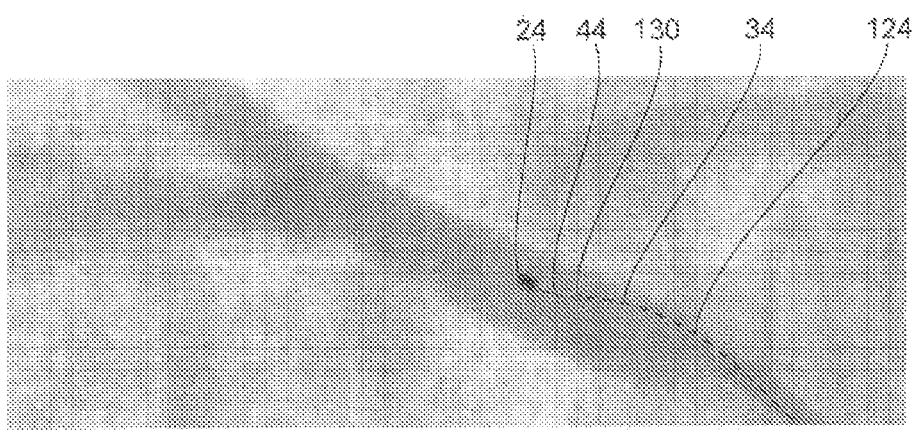
Figure 27C:
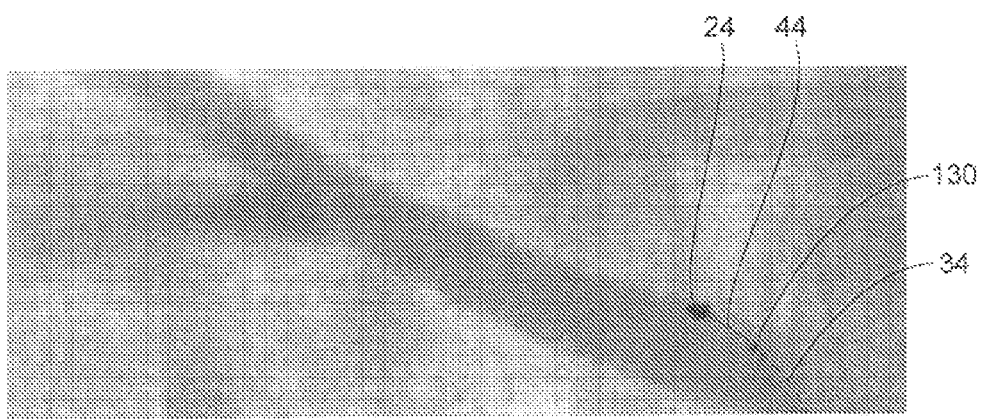
Figure 27D:
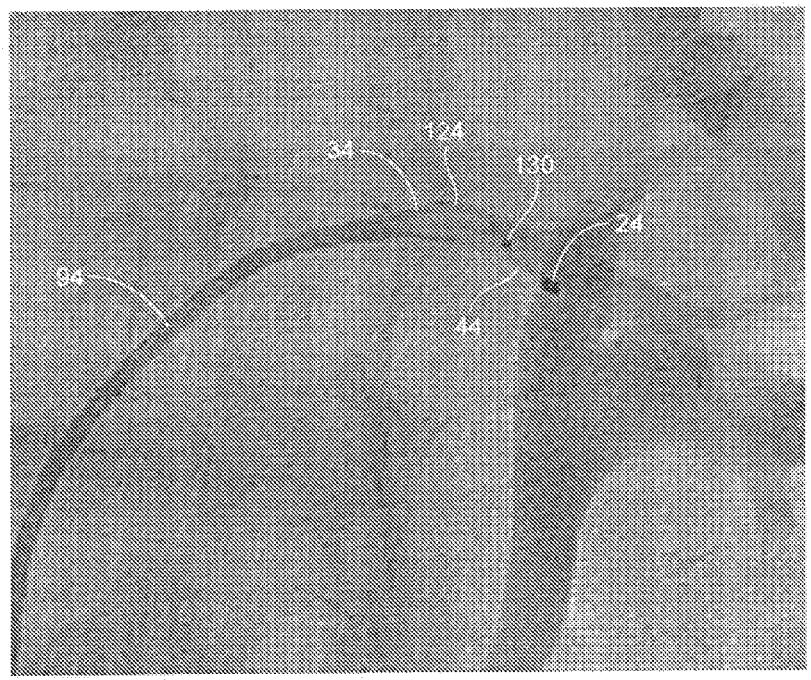
FIGS. 27D and 27E show fluoroscopic images of a treatment device, like that shown in FIG. 5 but without a force redirecting element, in multiple treatment positions within a renal artery during a human study.
Figure 27E:
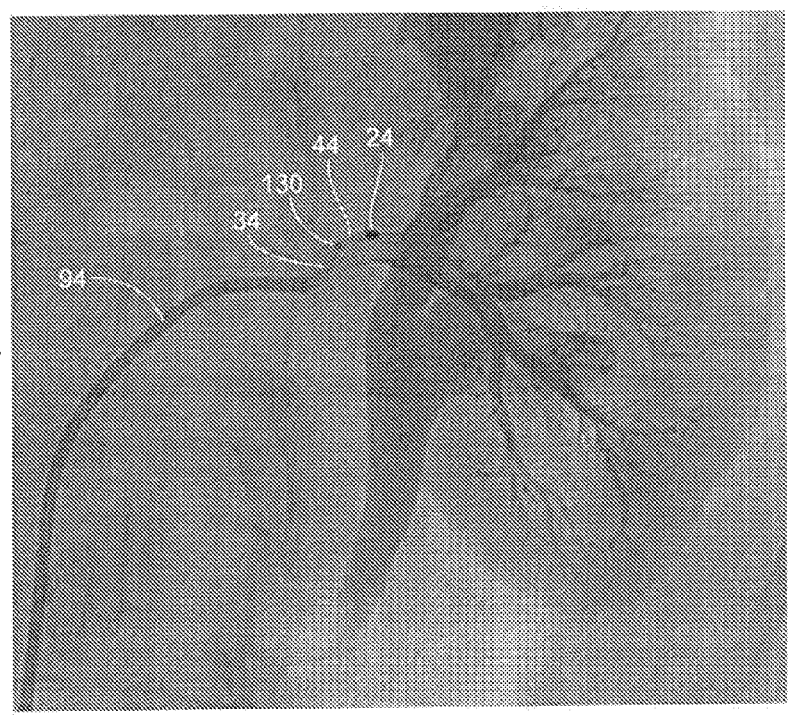

FIGS. 27A to 27C provide fluoroscopic images of a treatment device, similar to the one shown in FIG. 5 but without a force redirecting element 49, within a renal artery during an animal study. FIG. 27A shows positioning of the treatment device and energy delivery element 24 at a distal treatment location. The deflectable section 34 has been deflected to position the energy delivery element 24 in contact with the vessel wall and to cause flexure in the force dampening section 44. FIG. 27A also shows contact region 124 where the apex of the bend of the deflectable section 34 is in contact with the vessel wall in radial or angular opposition to contact between the energy delivery element and vessel wall. FIG. 27B shows the placement of the treatment device at a more proximal treatment location following circumferential rotation and axial retraction. FIG. 27C shows the placement of the treatment device at a proximal treatment location just distal to the junction of the aorta and renal artery. FIGS. 27D and 27E provide analogous fluoroscopic images depicting the treatment device, similar to the one shown in FIG. 5 but without a force redirecting element 49, positioned for treatment within a human renal artery. FIG. 27D shows the treatment device advanced to a distal treatment location similar to that described above with respect to FIG. 27A. FIG. 27E shows the treatment device in a proximal treatment position similar to that described above with respect to FIG. 27C.

Experience using the treatment device of FIGS. 27A to 27E revealed that the treatment device preformed the desired functions of for (i) percutaneous introduction into a femoral or brachial artery through a small-diameter access site; (ii) atraumatic passage through the tortuous intravascular path through an iliac artery, into the aorta, and into a respective left/right renal artery, including (iii) accommodating significant flexure at the junction of the left/right renal arteries and aorta to gain entry into the respective left or right renal artery; (iv) accommodating controlled translation, deflection, and/or rotation within the respective renal artery to attain proximity to and a desired alignment with an interior wall of the respective renal artery; (v) allowing the placement of at least one energy delivery element into contact with tissue on the interior wall in an orientation that optimizes the active surface area of the energy delivery element; and (vi) allowing substantially stable contact force between the at least one energy delivery element and the interior wall during motion of the renal artery with respect to the aorta due to respiration and/or blood flow pulsatility.

However, experience using the treatment device of FIGS. 27A to 27E also revealed that the functions of (iv), (v), and (vi) could be improved by modifying the treatment device to have a force redirecting element as described in the present application, particularly when used in renal arteries with greater degrees of tortuousity.

Since both the energy delivery element 24 and solder 130 at the distal end of the deflectable section 34 can be radiopaque, as shown in FIGS. 27A to 27C, the operator using angiographic visualization can use the image corresponding to the first treatment location to relatively position the treatment device for the second treatment. For example, in renal arteries of average length, it is desirable for the clinical operator to treat at about every 5 mm along the length of the main artery. In embodiments where the length of the force dampening section 44 is 5 mm, the operator can simply retract the device such that the current position of the energy delivery element 24 is longitudinally aligned with the position of the solder 130 in the previous treatment.

In another embodiment, a different type of radiopaque marker can replace solder 130. For example, a band of platinum can be attached to the distal end of the deflectable section to serve as a radiopaque marker.

Since angiographic visualization of the vasculature generally requires contrast agent to be infused into the renal artery, it may be desirable to incorporate within or alongside the treatment device a lumen and/or port for infusing contrast agent into the blood stream. Alternatively, the contrast agent can be delivered into the blood alongside the treatment device within the annular space between the treatment device and the guide catheter through which the device is delivered.

Exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

D. Control of Applied Energy

Figure 25:
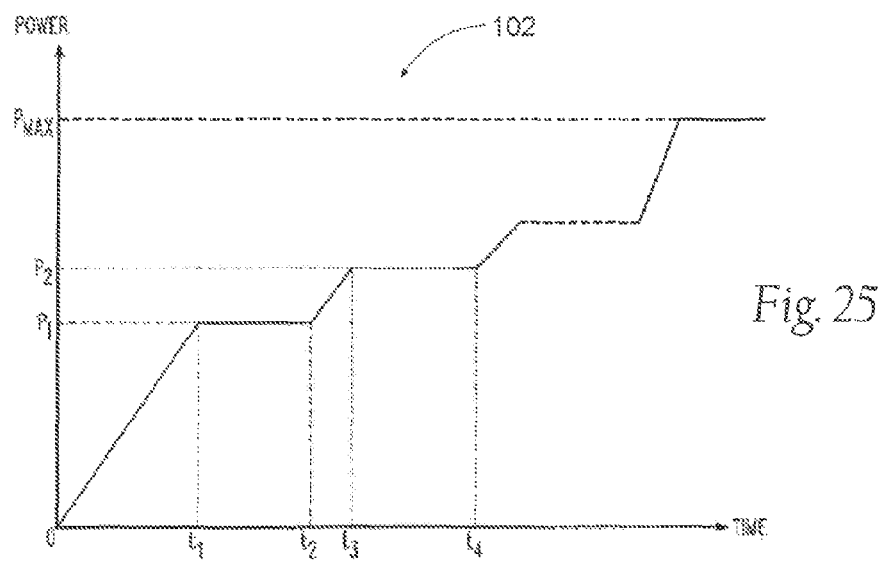
FIG. 25 shows an energy delivery algorithm corresponding to the energy generator of a system, like that shown in FIG. 5.

With the treatments disclosed herein for delivering therapy to target tissue, it may be beneficial for energy to be delivered to the target neural structures in a controlled manner. The controlled delivery of energy will allow the zone of thermal treatment to extend into the renal fascia while reducing undesirable energy delivery or thermal effects to the vessel wall. A controlled delivery of energy may also result in a more consistent, predictable and efficient overall treatment. Accordingly, the generator 26 desirably includes programmed instructions comprising an algorithm 102 (see FIG. 5) for controlling the delivery of power and energy to the thermal heating device. The algorithm 102, a representative embodiment of which is shown in FIG. 25, can be implemented as a conventional computer program for execution by a processor coupled to the generator 26. A caregiver using step-by-step instructions can also implement the algorithm 102 manually.

The operating parameters monitored in accordance with the algorithm may include, for example, temperature, time, impedance, power, flow velocity, volumetric flow rate, blood pressure, heart rate, etc. Discrete values in temperature may be used to trigger changes in power or energy delivery. For example, high values in temperature (e.g. 85 degrees C.) could indicate tissue desiccation in which case the algorithm may decrease or stop the power and energy delivery to prevent undesirable thermal effects to target or non-target tissue. Time additionally or alternatively may be used to prevent undesirable thermal alteration to non-target tissue. For each treatment, a set time (e.g., 2 minutes) is checked to prevent indefinite delivery of power.

Impedance may be used to measure tissue changes. Impedance indicates the electrical property of the treatment site. If a thermal inductive, electric field is applied to the treatment site the impedance will decrease as the tissue cells become less resistive to current flow. If too much energy is applied, tissue desiccation or coagulation may occur near the electrode, which would increase the impedance as the cells lose water retention and/or the electrode surface area decreases (e.g., via the accumulation of coagulum). Thus, an increase in tissue impedance may be indicative or predictive of undesirable thermal alteration to target or non-target tissue.

Additionally or alternatively, power is an effective parameter to monitor in controlling the delivery of therapy. Power is a function of voltage and current. The algorithm may tailor the voltage and/or current to achieve a desired power.

Derivatives of the aforementioned parameters (e.g., rates of change) also may be used to trigger changes in power or energy delivery. For example, the rate of change in temperature could be monitored such that power output is reduced in the event that a sudden rise in temperature is detected. Likewise, the rate of change of impedance could be monitored such that power output is reduced in the event that a sudden rise in impedance is detected.

As seen in FIG. 25, when a caregiver initiates treatment (e.g., via the foot pedal), the algorithm 102 commands the generator 26 to gradually adjust its power output to a first power level $P_1$ (e.g., 5 watts) over a first time period $t_1$ (e.g., 15 seconds). The power increase during the first time period is generally linear. As a result, the generator 26 increases its power output at a generally constant rate of $P_1/t_1$. Alternatively, the power increase can be non-linear (e.g., exponential or parabolic) with a variable rate of increase. Once $P_1$ and $t_1$ are achieved, the algorithm can hold at $P_1$ until a new time $t_2$ for a predetermined period of time $t_2-t_1$ (e.g., 3 seconds). At $t_2$ power is increased by a predetermined increment (e.g., 1 watt) to $P_2$ over a predetermined period of time, $t_3-t_2$ (e.g., 1 second). This power ramp in predetermined increments of about 1 watt over predetermined periods of time can continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In FIG. 25, algorithm 102 illustratively comprises a power-control algorithm. However, it should be understood that algorithm 102 alternatively may comprise a temperature-control algorithm. For example, power may be gradually increased until a desired temperature (or temperatures) is obtained for a desired duration (durations). In another embodiment, a combination power-control and temperature-control algorithm may be provided.

As discussed, the algorithm 102 includes monitoring certain operating parameters (e.g., temperature, time, impedance, power, flow velocity, volumetric flow rate, blood pressure, heart rate, etc.). The operating parameters can be monitored continuously or periodically. The algorithm 102 checks the monitored parameters against predetermined parameter profiles to determine whether the parameters individually or in combination fall within the ranges set by the predetermined parameter profiles. If the monitored parameters fall within the ranges set by the predetermined parameter profiles, then treatment can continue at the commanded power output. If monitored parameters fall outside the ranges set by the predetermined parameter profiles, the algorithm 102 adjusts the commanded power output accordingly. For example, if a target temperature (e.g., 65 degrees C.) is achieved, then power delivery is kept constant until the total treatment time (e.g., 120 seconds) has expired. If a first temperature threshold (e.g., 70 degrees C.) is achieved or exceeded, then power is reduced in predetermined increments (e.g., 0.5 watts, 1.0 watts, etc.) until a target temperature is achieved. If a second power threshold (e.g., 85 degrees C.) is achieved or exceeded, thereby indicating an undesirable condition, then power delivery can be terminated. The system can be equipped with various audible and visual alarms to alert the operator of certain conditions.

The following is a non-exhaustive list of events under which algorithm 102 may adjust and/or terminate/discontinue the commanded power output:

(1) The measured temperature exceeds a maximum temperature threshold (e.g., about 70 degrees to about 85 degrees C.).

(2) The average temperature derived from the measured temperature exceeds an average temperature threshold (e.g., about 65 degrees C.).

(3) The rate of change of the measured temperature exceeds a rate of change threshold.

(4) The temperature rise over a period of time is below a minimum temperature change threshold while the generator 26 has non-zero output. Poor contact between the energy delivery element 24 and the arterial wall can cause such a condition.

(5) A measured impedance exceeds an impedance threshold (e.g., <20 Ohms, or >500 Ohms).

(6) A measured impedance exceeds a relative threshold (e.g., impedance decreases from a starting or baseline value and then rises above this baseline value)

(7) A measured power exceeds a power threshold (e.g., >8 Watts or >10 Watts).

(8) A measured duration of power delivery exceeds a time threshold (e.g., >120 seconds).

Figure 26:
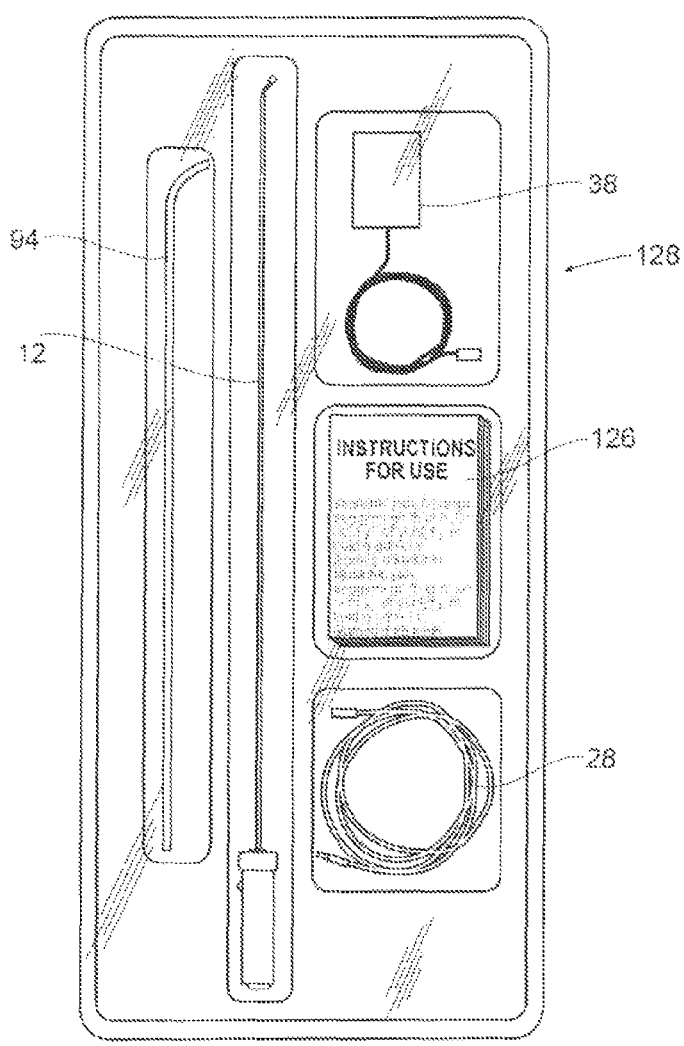
FIG. 26 shows several components of a system and treatment device, like that shown in FIG. 5, packaged within a single kit.

V. Prepackaged Kit for Distribution, Transport and Sale of the Disclosed Apparatuses and Systems As shown in FIG. 26, one or more components of the system 10 shown in FIG. 5 can be packaged together for convenient delivery to and use by the customer/clinical operator. Components suitable for packaging include, the treatment device 12, the cable 28 for connecting the treatment device 12 to the generator 26, the neutral or dispersive electrode 38, and one or more guide catheters 94 (e.g., a renal guide catheter). Cable 28 can also be integrated into the treatment device 12 such that both components are packaged together. Each component may have its own sterile packaging (for components requiring sterilization) or the components may have dedicated sterilized compartments within the kit packaging. This kit may also include step-by-step instructions for use 126 that provide the operator with technical product features and operating instructions for using the system 10 and treatment device 12, including all methods of insertion, delivery, placement and use of the treatment device disclosed herein.

VI. Additional Clinical Uses of the Disclosed Apparatuses, Methods and Systems Although much of the disclosure in this Specification relates to at least partially denervating a kidney of a patient to block afferent and/or efferent neural communication from within a renal blood vessel (e.g., renal artery), the apparatuses, methods and systems described herein may also be used for other intravascular treatments. For example, the aforementioned catheter system, or select aspects of such system, can be placed in other peripheral blood vessels to deliver energy and/or electric fields to achieve a neuromodulatory affect by altering nerves proximate to these other peripheral blood vessels. There are a number of arterial vessels arising from the aorta which travel alongside a rich collection of nerves to target organs. Utilizing the arteries to access and modulate these nerves may have clear therapeutic potential in a number of disease states. Some examples include the nerves encircling the celiac trunk, superior mesenteric artery, and inferior mesenteric artery.

Sympathetic nerves proximate to or encircling the arterial blood vessel known as the celiac trunk may pass through the celiac ganglion and follow branches of the celiac trunk to innervate the stomach, small intestine, abdominal blood vessels, liver, bile ducts, gallbladder, pancreas, adrenal glands, and kidneys. Modulating these nerves either in whole (or in part via selective modulation) may enable treatment of conditions including (but not limited to) diabetes, pancreatitis, obesity, hypertension, obesity related hypertension, hepatitis, hepatorenal syndrome, gastric ulcers, gastric motility disorders, irritable bowel syndrome, and autoimmune disorders such as Crohn's disease.

Sympathetic nerves proximate to or encircling the arterial blood vessel known as the inferior mesenteric artery may pass through the inferior mesenteric ganglion and follow branches of the inferior mesenteric artery to innervate the colon, rectum, bladder, sex organs, and external genitalia. Modulating these nerves either in whole (or in part via selective modulation) may enable treatment of conditions including (but not limited to) GI motility disorders, colitis, urinary retention, hyperactive bladder, incontinence, infertility, polycystic ovarian syndrome, premature ejaculation, erectile dysfunction, dyspareunia, and vaginismus.

While arterial access and treatments have received attention in this Specification, the disclosed apparatuses, methods and systems can also be used to deliver treatment from within a peripheral vein or lymphatic vessel.

VII. Conclusion

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the invention. Where the context permits, singular or plural terms may also include the plural or singular term, respectively. For example, much of the disclosure herein describes an energy delivery element 24 or electrode 46 in the singular. It should be understood that this application does not exclude two or more energy delivery elements or electrodes.

It should also be understood that energy delivery element 24 can be an electrode, radiofrequency electrode, cooled radiofrequency electrode, thermal element, thermal heating element, electrically resistive heating element, cryoablative applicator, microwave antenna, ultrasound transducer, high intensity focused ultrasound transducer, or laser emitter.

Additionally, other terms used herein may be expressed in different and interchangeable ways. For example, a force transmitting section can also be an proximal force transmitting section, elongated tubular shaft; a first flexure zone can also be a flexible tubular structure; a deflectable section can also be an intermediate flexure zone or a second flexure zone or a deflectable tubular body; a control wire can be a flexure control element; a force dampening section can be a third flexure zone or distal flexure zone or passively flexible structure; a force redirecting element can be a pre-shaped geometry.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the invention. Accordingly, the invention is not limited except as by the appended claims.

We claim:

1. A catheter apparatus for thermally modulating renal nerves from within a renal artery of a patient, the catheter apparatus comprising:
    an elongated tubular shaft extending along an axis, the elongated tubular shaft having a proximal end and a distal end;
    a handle proximal to the proximal end of the elongated tubular shaft;
    a flexible tubular structure distal from the distal end of the elongated tubular shaft, the flexible tubular structure adapted to make a transitional bend from the aorta of the patient to the renal artery;
    a deflectable tubular body distal from the flexible tubular structure;
    a flexure control element coupled to the deflectable tubular body;
    a flexure controller carried by the handle and coupled to the flexure control element, the flexure controller adapted to apply a force via the flexure control element to the deflectable tubular body;
    a force dampening section distal from the deflectable tubular body; and
    a single energy delivery element distal from and carried by the force dampening section;
    wherein the deflectable tubular body is adapted for flexure in a predetermined direction upon application of the force from the flexure control element to position the energy delivery element into contact with the renal artery wall;
    wherein the force dampening section comprises a passively flexible structure that is adapted for passive flexure in any plane through the axis in response to a force applied to the energy delivery element upon contact with the renal artery wall, and further wherein the force dampening section is configured to accommodate stable contact between the energy delivery element and the renal artery wall;
    wherein at least one of the deflectable tubular body and the force dampening section comprises a force redirecting element that is adapted to facilitate atraumatic contact between the energy delivery element and the renal artery wall.

2. The catheter apparatus of claim 1 wherein the force redirecting element comprises a pre-shaped geometry incorporated into the deflectable tubular body.

3. The catheter apparatus of claim 2 wherein the pre-shaped geometry of the force redirecting element comprises an angular bend having a preset angle of about 20 to 40 degrees.

4. The catheter apparatus of claim 1 wherein the force redirecting element comprises a pre-shaped geometry that is adapted to facilitate flexure of the passively flexible structure.

5. The catheter apparatus of claim 4 wherein the pre-shaped geometry is configured to reduce the contact force between the energy delivery element and the renal artery wall necessary to cause flexure of the passively flexible structure.

6. The catheter apparatus of claim 1 wherein the passively flexible structure, force redirecting element and energy delivery element comprise a distal assembly that is distal from the deflectable tubular body.

7. The catheter apparatus of claim 6 wherein the passively flexible structure is distal from the force redirecting element.

8. The catheter apparatus of claim 6 wherein the passively flexible structure and the force redirecting element comprise a single element.

9. The catheter apparatus of claim 6 wherein the distal assembly has a length along the axis of the elongated tubular shaft that is no greater than 10 mm.

10. The catheter apparatus of claim 6 wherein the distal assembly has a length along the axis of the elongated tubular shaft that is no greater than 5 mm.

11. The catheter apparatus of claim 1 wherein the deflectable tubular body is configured for a state of maximum flexure, and wherein the state of maximum flexure is achieved when the deflectable tubular body moves the energy delivery element away from the axis of the elongated tubular shaft by a predetermined distance.

12. The catheter apparatus of claim 11 wherein the predetermined distance is about 2 mm to 20 mm.

13. The catheter apparatus of claim 11 wherein the predetermined distance is about 10 mm to 14 mm.

14. The catheter apparatus of claim 11 wherein the force dampening section, force redirecting element and energy delivery element comprise a distal assembly that is distal from the deflectable tubular body, and wherein the distal assembly has a length along the axis of the elongated tubular shaft from about 3 mm to about 6 mm, the deflectable tubular body has a length along the axis of the elongated tubular shaft from about 8 mm to about 15 mm.

15. The catheter apparatus of claim 14 wherein the predetermined distance is about 10 mm to about 14 mm.

16. The catheter apparatus of claim 11 wherein deflectable tubular body in the state of maximum flexure comprises a transitional bend having a radius of curvature no greater than about 25 mm.

17. The catheter apparatus of claim 11 wherein deflectable tubular body in the state of maximum flexure comprises a transitional bend having a radius of curvature no greater than about 15 mm.

18. The catheter apparatus of claim 1 wherein the deflectable tubular body has a length from about 5 mm to about 20 mm.

19. The catheter apparatus of claim 1 wherein the deflectable tubular body has a length of less than or equal to about 12.5 mm.

20. The catheter apparatus of claim 1 wherein the force redirecting element comprises a pre-shaped geometry that is biased in a radial direction that is opposite the predetermined direction of flexure of the deflectable tubular body.

21. The catheter apparatus of claim 1 wherein the force redirecting element comprises a pre-shaped geometry that is biased in a radial direction that is the same as the predetermined direction of flexure of the deflectable tubular body.

22. The catheter apparatus of claim 1 wherein the deflectable tubular body comprises a cutout pattern comprising a spine.

23. The catheter apparatus of claim 22 wherein the spine of the deflectable tubular body comprises a circumferentially positioned spine.

24. The catheter apparatus of claim 22 wherein the spine of the deflectable tubular body comprises a centrally positioned spine.

25. The catheter apparatus of claim 1 wherein the flexible tubular structure is more flexible than the elongated tubular shaft, the deflectable tubular body is more flexible than the flexible tubular structure, and the force dampening section is more flexible than the deflectable tubular body.

26. The catheter apparatus of claim 25 wherein the elongated tubular shaft, the flexible tubular structure, and the deflectable tubular body comprise a single piece tubular structure.

27. The catheter apparatus of claim 26 wherein the increased flexibility of the flexible tubular structure and the deflectable tubular body result from laser cutting of the single piece tubular structure.

28. The catheter apparatus of claim 1 wherein the deflectable tubular body varies between a relaxed configuration and a deflected configuration and wherein the deflectable tubular body in the relaxed configuration is more flexible than the flexible tubular structure and the deflectable tubular body in the deflected configuration is less flexible than the flexible tubular structure.

29. The catheter apparatus of claim 1 wherein the energy delivery element is configured to create a thermal lesion comprising at least 30% circumferential coverage of the renal artery wall.

30. The catheter apparatus of claim 1 wherein the elongated tubular shaft and the energy delivery element are sized and configured for intravascular delivery into the renal artery via a 6 French guide catheter.

31. The catheter apparatus of claim 1 wherein the elongated tubular shaft and the energy delivery element are sized and configured for intravascular delivery into the renal artery via a 5 French guide catheter.

32. The catheter apparatus of claim 1 wherein the deflectable tubular body and force dampening section are configured to apply a stabilizing contact force between the energy delivery element and the renal artery wall sufficient to maintain wall contact during movement of the renal artery caused by respiration of the patient.

33. The catheter apparatus of claim 1, further comprising a sensor adjacent to, on, or within the energy delivery element, the sensor configured to monitor a parameter of at least one of the apparatus and the renal artery wall.

34. The catheter apparatus of claim 33, further comprising a temperature sensor, impedance sensor, optical sensor or micro sensor.

35. The catheter apparatus of claim 33, further comprising a feedback control system configured to alter thermal treatment delivered by the energy delivery element in response to the monitored parameter.

36. The catheter apparatus of claim 35 wherein the feedback control system comprises an algorithm for controlling thermal treatment delivered by the energy delivery element.

37. The catheter apparatus of claim 1 wherein the energy delivery element is configured to apply thermal treatment using at least one of radiofrequency energy, microwave energy, ultrasound energy, laser/light energy, thermal fluid, resistive heating, and cryogenic fluid.

38. The catheter apparatus of claim 1 wherein the energy delivery element comprises an electrode for applying radiofrequency energy to tissue.

39. The catheter apparatus of claim 1 wherein the handle comprises a rotator coupled to the tubular elongated shaft and configured to rotate the tubular elongated shaft about its axis without rotating the handle, and wherein the rotator and handle are adapted to prevent the rotation of the tubular elongated shaft beyond a predetermined number of revolutions.

40. The catheter apparatus of claim 1, wherein the catheter apparatus is a component of a medical treatment kit, and wherein the medical treatment kit further comprises a cable configured to electrically connect the catheter apparatus to an energy source and a dispersive electrode configured to provide a return path for an energy field from the catheter apparatus.

41. The catheter apparatus of claim 1, further comprising instructions for delivering the catheter apparatus into a renal artery of the patient and at least partially denervating a kidney of the patient corresponding to the renal artery to treat the patient for a condition associated with at least one of hypertension, heart failure, kidney disease, chronic renal failure, central sympathetic hyperactivity, insulin resistance diabetes, metabolic disorder, arrhythmia, acute myocardial infarction and cardio-renal syndrome.

42. A catheter apparatus for thermally modulating renal nerves from within a renal artery of a patient, the catheter apparatus comprising:
   an elongated tubular shaft extending along an axis, the elongated tubular shaft having a proximal end and a distal end;
   a handle proximal to the proximal end of the elongated tubular shaft;
   a flexible tubular structure distal from the distal end of the elongated tubular shaft, the flexible tubular structure adapted to make a transitional bend from the aorta of the patient to the renal artery;
   a deflectable tubular body distal from the flexible tubular structure;
   a flexure control element coupled to the deflectable tubular body;
   a flexure controller carried by the handle and coupled to the flexure control element, the flexure controller adapted to apply a force via the flexure control element to the deflectable tubular body; and
   a distal assembly distal from the deflectable tubular body comprising a force dampening section, a force redirecting element and an energy delivery element distal from and carried by the force dampening section, wherein the energy delivery element comprises a single distal tip electrode;
   wherein the deflectable tubular body is adapted for flexure in a predetermined direction upon application of the force from the flexure control element to position the energy delivery element into contact with the renal artery wall;
   wherein the force dampening section comprises a passively flexible structure that is adapted for passive flexure in any plane through the axis in response to a force applied to the energy delivery element upon contact with the renal artery wall, and further wherein the force dampening section is configured to accommodate stable contact between the energy delivery element and the renal artery wall;
   wherein the force redirecting element is adapted to facilitate flexure of the catheter apparatus and atraumatic contact between the energy delivery element and renal artery wall.

43. A catheter apparatus for thermally modulating renal nerves from within a renal artery of a patient, the catheter apparatus comprising:
   an elongated tubular shaft extending along an axis, the elongated tubular shaft having a proximal end and a distal end;
   a handle proximal to the proximal end of the elongated tubular shaft;
   a flexible tubular structure distal from the distal end of the elongated tubular shaft, the flexible tubular structure adapted to make a transitional bend from the aorta of the patient to the renal artery;
   a deflectable tubular body distal from the flexible tubular structure;
   a flexure control element coupled to the deflectable tubular body;
   a flexure controller carried by the handle and coupled to the flexure control element, the flexure controller adapted to apply a force via the flexure control element to the deflectable tubular body; and
   a distal assembly distal from the deflectable tubular body comprising a passively flexible structure, a pre-shaped geometry and a thermal element distal from and carried by the passively flexible structure, wherein the thermal element comprises a single distal tip electrode;
   wherein the deflectable tubular body is adapted for flexure in a predetermined direction upon application of the force from the flexure control element to position the thermal element into contact with the renal artery wall;
   wherein the passively flexible structure is adapted for passive flexure in any plane through the axis in response to a force applied to the thermal element upon contact with the renal artery wall, and further wherein the passively flexible structure is configured to accommodate stable contact between the thermal element and the renal artery wall;
   wherein the pre-shaped geometry is adapted to facilitate flexure of the passively flexible structure and atraumatic contact between the thermal element and renal artery wall.

* * * * *